United States Patent
Carroll et al.

(10) Patent No.: US 11,535,664 B2
(45) Date of Patent: *Dec. 27, 2022

(54) MULTI-VALENT HEPATITIS B VIRUS ANTIGEN BINDING MOLECULES AND USES THEREOF

(71) Applicant: IGM Biosciences, Inc., Mountain View, CA (US)

(72) Inventors: Stephen F. Carroll, Walnut Creek, CA (US); Ramesh Baliga, Redwood City, CA (US); Dean Ng, San Francisco, CA (US); Bruce Keyt, Hillsborough, CA (US)

(73) Assignee: IGM Biosciences, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/795,433

(22) Filed: Feb. 19, 2020

(65) Prior Publication Data

US 2021/0002353 A1    Jan. 7, 2021

Related U.S. Application Data

(63) Continuation of application No. 15/560,905, filed as application No. PCT/US2016/024348 on Mar. 25, 2016, now Pat. No. 10,604,559.

(60) Provisional application No. 62/137,881, filed on Mar. 25, 2015.

(51) Int. Cl.
| | | |
|---|---|---|
| *C07K 16/08* | (2006.01) | |
| *C07K 16/28* | (2006.01) | |
| *A61K 39/395* | (2006.01) | |
| *A61K 39/40* | (2006.01) | |
| *G01N 33/50* | (2006.01) | |
| *G01N 33/569* | (2006.01) | |
| *A61P 1/16* | (2006.01) | |
| *A61P 31/20* | (2006.01) | |
| *A61K 39/00* | (2006.01) | |

(52) U.S. Cl.
CPC ......... *C07K 16/082* (2013.01); *A61K 39/395* (2013.01); *A61K 39/39541* (2013.01); *A61K 39/40* (2013.01); *A61P 1/16* (2018.01); *A61P 31/20* (2018.01); *C07K 16/2809* (2013.01); *G01N 33/502* (2013.01); *G01N 33/56983* (2013.01); *A61K 2039/505* (2013.01); *C07K 2317/24* (2013.01); *C07K 2317/31* (2013.01); *C07K 2317/35* (2013.01); *C07K 2317/56* (2013.01); *C07K 2317/60* (2013.01); *C07K 2317/622* (2013.01); *C07K 2317/734* (2013.01); *C07K 2317/76* (2013.01); *G01N 2333/02* (2013.01); *G01N 2500/04* (2013.01); *G01N 2500/10* (2013.01)

(58) Field of Classification Search
CPC .. A61P 43/00; A61P 9/00; A61P 11/00; C07K 16/468; C07K 2317/569; C07K 2317/622; C07K 14/70503; C07K 2319/30; A61K 38/1774; C12N 2760/10022; C12N 2760/16121; G01N 33/577

See application file for complete search history.

(56) References Cited

U.S. PATENT DOCUMENTS

| | | |
|---|---|---|
| 4,433,059 A | 2/1984 | Chang |
| 5,061,619 A | 10/1991 | Wilson |
| 6,063,905 A | 5/2000 | Capra |
| 7,115,723 B1 | 10/2006 | Hong |
| 8,377,435 B2 | 2/2013 | Bhat |
| 8,420,353 B2 | 4/2013 | Hong |
| 9,261,510 B2 | 2/2016 | Schotz |
| 9,409,976 B2 | 8/2016 | Teng |
| 9,458,241 B2 | 10/2016 | Bhat |
| 9,938,347 B2 | 4/2018 | Wang |
| 9,951,134 B2 | 4/2018 | Keyt |
| 10,351,631 B2 | 7/2019 | Keyt |
| 10,400,038 B2 | 9/2019 | Keyt |
| 10,604,559 B2 | 3/2020 | Carroll |
| 10,618,978 B2 | 4/2020 | Keyt |
| 10,689,449 B2 | 6/2020 | Wang |
| 10,787,520 B2 | 9/2020 | Keyt |
| 10,954,302 B2 | 3/2021 | Keyt |
| 10,975,147 B2 | 4/2021 | Keyt |
| 11,192,941 B2 | 12/2021 | Keyt |
| 11,401,337 B2 | 8/2022 | Baliga |

(Continued)

FOREIGN PATENT DOCUMENTS

| | | |
|---|---|---|
| CN | 1600856 | 3/2005 |
| CN | 102321720 | 1/2012 |
| EP | 0507587 | 10/1992 |
| JP | S6358260 | 3/1988 |
| JP | 2000509269 | 7/2000 |

(Continued)

OTHER PUBLICATIONS

Gupta et al. Journal of Drug Targeting, 2007, vol. 15, issue 10, pp. 701-713.*

(Continued)

*Primary Examiner* — Bao Q Li

(57) ABSTRACT

This disclosure provides a multimeric hepatitis B virus (HBV) protein binding molecule, e.g., a dimeric IgA or a pentameric or hexameric IgM binding molecule, comprising at least two bivalent binding units, or variants or fragments thereof, each comprising at least two antibody heavy chain constant regions or fragments thereof, wherein each heavy chain constant region or fragment thereof is associated with an HBV antigen binding domain. The disclosure also provides compositions comprising the multimeric binding molecules, polynucleotides encoding the multimeric binding molecules, and methods to make and use the multimeric binding molecules.

19 Claims, 7 Drawing Sheets

Specification includes a Sequence Listing.

(56) References Cited

U.S. PATENT DOCUMENTS

| | | |
|---|---|---|
| 2002/0058247 A1 | 5/2002 | Sallberg |
| 2007/0154469 A1 | 7/2007 | Irie |
| 2010/0172899 A1 | 7/2010 | Irie |
| 2014/0121358 A1 | 5/2014 | Hong |
| 2016/0222132 A1 | 8/2016 | Keyt |
| 2016/0326233 A1 | 11/2016 | Mondelli |
| 2016/0368971 A1 | 12/2016 | Keyt |
| 2017/0183409 A1 | 6/2017 | Keyt |
| 2017/0283510 A1 | 10/2017 | Keyt |
| 2017/0320955 A1 | 11/2017 | Wang |
| 2018/0009897 A1 | 1/2018 | Wang |
| 2018/0118814 A1 | 5/2018 | Carroll |
| 2018/0265596 A1 | 9/2018 | Keyt |
| 2019/0002566 A1 | 1/2019 | Keyt |
| 2019/0100597 A1 | 4/2019 | Keyt |
| 2019/0185570 A1 | 6/2019 | Keyt |
| 2019/0330360 A1 | 10/2019 | Wang |
| 2019/0330374 A1 | 10/2019 | Wang |
| 2019/0338031 A1 | 11/2019 | Keyt |
| 2019/0338040 A1 | 11/2019 | Keyt |
| 2019/0338041 A1 | 11/2019 | Baliga |
| 2020/0190190 A1 | 6/2020 | Keyt |
| 2020/0239572 A1 | 7/2020 | Baliga |
| 2020/0255546 A1 | 8/2020 | Keyt |
| 2020/0377577 A1 | 12/2020 | Keyt |
| 2021/0032357 A1 | 2/2021 | Keyt |
| 2021/0087273 A1 | 3/2021 | Baliga |
| 2021/0147567 A1 | 5/2021 | Baliga |
| 2021/0163600 A1 | 6/2021 | Keyt |
| 2021/0380701 A1 | 12/2021 | Baliga |
| 2021/0388098 A1 | 12/2021 | Keyt |
| 2022/0106398 A1 | 4/2022 | Baliga |
| 2022/0106399 A1 | 4/2022 | Baliga |
| 2022/0169751 A1 | 6/2022 | Wang |
| 2022/0177595 A1 | 6/2022 | Wang |
| 2022/0340676 A1 | 10/2022 | Baliga |

FOREIGN PATENT DOCUMENTS

| | | |
|---|---|---|
| WO | 1995021189 | 8/1995 |
| WO | 1997040164 | 10/1997 |
| WO | 2003080672 | 10/2003 |
| WO | 2004110143 | 12/2004 |
| WO | 2006052641 | 5/2006 |
| WO | 2011045079 | 4/2011 |
| WO | 2013049254 | 4/2013 |
| WO | 2013120012 | 8/2013 |
| WO | 2014022592 | 2/2014 |
| WO | 2014048910 | 4/2014 |
| WO | 2015053887 A1 | 4/2015 |
| WO | 2015120474 | 8/2015 |
| WO | 2015153912 | 10/2015 |
| WO | 2016118641 | 7/2016 |
| WO | 2016141303 | 9/2016 |
| WO | 2016168758 | 10/2016 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |
| WO | 2021030688 | 2/2021 |
| WO | 2021034646 | 2/2021 |
| WO | 2021041250 | 3/2021 |
| WO | 2021055765 | 3/2021 |
| WO | 2021141902 | 7/2021 |
| WO | 2021216756 | 10/2021 |
| WO | 2021231639 | 11/2021 |
| WO | 2022026475 | 2/2022 |
| WO | 2022109023 | 5/2022 |

OTHER PUBLICATIONS

Leong et al. DNA cell Biol. 2014, vol. 33 (12), pp. 823-829.*
Bharathkar et al. eLife published on Oct. 2020, pp. 1-22.*
Woof et al. Mucosal Immunology, published on Nov. 2011, vol. 4, No. 6, pp. 590-597.*
Azuma et al., "Robust Expansion of Human Hepatocytes in Fah−/−/Rag2−/−/Il2rg−/− Mice", Nature Biotechnology, Aug. 2007, pp. 903-910, vol. 25, Issue 8.
Bility et al., "Hepatitis B Virus Infection and Immunopathogenesis in a Humanized Mouse Model: Induction of Human-Specific Liver Fibrosis and M2-Like Macrophages", PLOS Pathogens, Mar. 2014, e1004032, pp. 1-14, vol. 10, Issue 3.
Bissig et al., "Repopulation of Adult and Neonatal Mice with Human Hepatocytes: A Chimeric Animal Model", Proceedings of the National Academy of Sciences, Dec. 18, 2007, pp. 20507-20511, vol. 104, No. 51.
Cerino et al., "A Human Monoclonal Antibody Against Hepatitis B Surface Antigen with Potent Neutralizing Activity", PLOS One, Apr. 29, 2015, pp. 1-10, vol. 10, No. 4.
Chai et al., "Properties of Subviral Particles of Hepatitis B Virus", Journal of Virology, Aug. 2008, pp. 7812-7817, vol. 82, No. 16.
Chen et al., "A Function of the Hepatitis B Virus Precore Protein is to Regulate the Immune Response to the Core Antigen", Proceedings of the National Academy of Sciences, Oct. 12, 2004, pp. 14913-14918, vol. 101, No. 41.
Dandri et al., "Repopulation of Mouse Liver with Human Hepatocytes and In Vivo Infection with Hepatitis B Virus", Hepatology, Apr. 2001, pp. 981-988, vol. 33, No. 4.
Dryden et al., "Native Hepatitis B Virions and Capsids Visualized by Electron Cry microscopy", Molecular Cell, Jun. 23, 2006, pp. 843-850, vol. 22.
Gripon et al., "Myristylation of the Hepatitis B Virus Large Surface Protein is Essential for Viral Infectivity", Virology Nov. 1995, pp. 292-299, vol. 213, Issue 2.
Heermann et al., "Large Surface Proteins of Hepatitis B Virus Containing the Pre-s Sequence", Journal of Virology, Nov. 1984, pp. 396-402, vol. 52, No. 2.
Hensel, F., et al., 2013, "Early development of PAT-SM6 for the treatment of melanoma", Melanoma Research, vol. 23: 264-275.
Hong et al,"In Vivo Neutralization of Hepatitis B Virus Infection by an Anti-preS1 Humanized Antibody in Chimpanzees", Virology, Jan. 5, 2004, pp. 134-141, vol. 318, Issue 1.
Horn, M., et al., 2010, "Preclinical In Vitro and In Vivo Characterization of the Fully Human Monoclonal IgM Antibody KBPA101 Specific for Pseudomonas aeruginosa Serotype IATS-011", Antimicrobial Agents and Chemotherapy, vol. 54(6): 2338-2344.
Ilan et al., "The Hepatitis B Virus-Trimera Mouse: A Model for Human HBV Infection and Evaluation of Anti-HBV Therapeutic Agents", Hepatology, Feb. 1999, pp. 553-562, vol. 29, Issue 2.
International Search Report and Written Opinion dated Jul. 28, 2016 issued in PCT Patent Application No. PCT/US2016/024348.
Kaetzel et al., "The Polymeric Immunoglobulin Receptor (Secretory Component) Mediates Transport of Immune Complexes Across Epithelial Cells: A Local Defense Function for IgA", Proceedings of the National Academy of Sciences, Oct. 1991, pp. 8796-8800, vol. 88.
Kaplan et al., "DNA Polymerase Associated with Human Hepatitis B Antigen", Journal of Virology, Nov. 1973, )p. 995-1005, vol. 12, No. 5.
Kew, "Hepatitis B Virus X Protein in the Pathogenesis of Hepatitis B Virus-Induced Hepatitis B Virus-Induced Hepatocellular Carcinoma" Journal of Gastroenterology and Hepatology, Jan. 2011, pp. 144-152, vol. 26, Issue Supplement 1.

(56) References Cited

OTHER PUBLICATIONS

Kim et al., "Enhanced Humanization and Affinity Maturation of Neutralizing Anti-Hepatitis B Virus preS1 Antibody Based on Antigen-Antibody Complex Structure", Federation of European Biochemical Societies Letters, Jan. 16, 2015, pp. 193-200, vol. 589 Issue 2.
Kosaka et al., "A Novel TK-NOG Based Humanized Mouse Model for the Study of HBV and HCV Infections", Biochemical and Biophysical Research Communications, Nov. 8, 2013, pp. 230-235, vol. 441, No. 1.
Kramvis et al., "Hepatitis B Virus Genotypes", Vaccine, Mar. 31, 2005, pp. 2409-2423, vol. 23, Issue 19.
Le Seyec et al., "Infection Process of the Hepatitis B Virus Depends on the Presence of a Defined Sequence in the Pre-S1 Domain", Journal of Virology, Mar. 1999, pp. 2052-2057, vol. 73, No. 5.
Maeng et al., "Fine Mapping of Virus-Neutralizing Epitopes on Hepatitis B Virus PreS1", Virology, Apr. 25, 2000, )p. 9-16, vol. 270, Issue 1.
Magnius et al., "Subtypes, Genotypes, and Molecular Epidemiology of the Hepatitis B Virus as Reflected by Sequence Variability of the S-Gene", Intervirology, 1995, pp. 24-34, vol. 38, No. 1-2.
Ng et al., "Hepatitis B Virus X Gene and Hepatocarcinogenesis", Journal of Gastroenterology, Aug. 2011, pp. 974-990, vol. 46, Issue 8.
Omar, D., et al., 2014, "IGM-55.5, a novel monoclonal human recombinant IgM antibody with potent activity against B cell leukemia and lymphoma", Abstract No. 645, AACR Annual Meeting, 2014, Apr. 5-9, San Diego, CA.
Park et al., "Hepatitis B Virus-Neutralizing Anti-Pre-S1 Human Antibody Fragments from Large Naive Antibody Phage Library", Antiviral Research, Dec. 2005, pp. 109-115, vol. 68, Issue 3.
Petit et al., "A Monoclonal Antibody Specific for the Hepatocyte Receptor Binding Site on Hepatitis B Virus", Molecular Immunology, Jun. 1989, pp. 531-537, vol. 26, Issue 6.
Pizarro et al., "Structural and Functional Characterization of a Monoclonal Antibody Specific for the preS1 Region of Hepatitis B Virus", Ferderation of European Biochemical Societies Letters, Dec. 14, 2001, pp. 463-468, vol. 509, Issue 3.
Rindisbacher et al., "Production of Human Secretory Component with Dimeric IgA Binding Capacity Using Viral Expression Systems", The Journal of Biological Chemistry, Jun. 9, 1995, pp. 14220-14228, vol. 270, No. 23.
Seifer et al., "In Vitro Tumorigenicity of Hepatitis B Virus DNA and HBx Protein", Journal of Hepatology, 1991, pp. 361-S65,vol. 13, Supp.4.
Short et al., "Structure of Hepatitis B Surface Antigen from Subviral Tubes Determined by Electron Cryomicroscopy", Journal of Molecular Biology, Jul. 3, 2009, pp. 135-141, vol. 390.
Shouval, "Hepatitis B Vaccines", Journal of Hepatology, 2003, pp. 70-76, vol. 39, Supplemental 1.
Sørensen, V., et al., (2000), "Structural requirements for incorporation of J chain into human IgM and IgA.", Int. Immunol. 12, 19-27.
Tang et al., "Molecular Functions and Biological Roles of Hepatitis B Virus X Protein", Cancer Science, Oct. 2006, pp. 977-983, vol. 97, No. 10.
Tesfaye et al., "Chimeric Mouse Model for the Infection of Hepatitis B and C Viruses", PLOS One, Oct. 2013, pp. 1-14, vol. 8, Issue 10.
Walsh et al,"Targeting the hepatitis B virus precore antigen with a novel IgNAR single variable domain intrabody", Virology, Jan. 15, 2011, pp. 132-141, vol. 411.
Xu et al., "Hepatitis B Virus-Induced Hepatocellular Carcinoma", Cancer Letters, Apr. 10, 2014, pp. 216-222, vol. 345, Issue 2.
Castro, C., et al., (2014), "Putting J chain back on the map: how might its expression define plasma cell development?", The Journal of Immunology, 193: 3248-3255.
Czajkowsky D., et al., (2009), "The human IgM pentamer is a mushroom-shaped molecule with a flexural bias," PNAS, 106(35): 14960-14965.
Duramad, O., et al., (2014), "IGM-55.5, a novel monoclonal human recombinant IgM antibody with potent activity against B cell leukemia and lymphoma", IGM Biosciences, Inc.—Research and Development SRI International—Cancer Pharmacology, Stanford—Department of Obstetrics and Gynecology, Abstract No. 645, AACR Annual Meeting, Apr. 5-9, 2014, San Diego CA.
Hexham, JM., et al., (1999), "A Human Immunoglobulin (Ig) A Cα3 Domain Motif Directs Polymeric Ig Receptor-mediated Secretion", J. Exp Med, 189(4): 747-751.
Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.
Woof, JM., et al., (2011), ,"Structure and Function Relationships in IgA", Mucosal Immunology, vol. 4(6): pp. 590-597.
U.S. Appl. No. 17/996,760, Specification, Claims, Abstract and Drawings as filed Oct. 20, 2022 with U.S. Patent Office.
U.S. Appl. No. 18/052,388, Specification, Claims, Abstract and Drawings as filed Nov. 3, 2022 with U.S. Patent Office.
U.S. Appl. No. 17/998,307, Specification, Claims, Abstract and Drawings as filed Nov. 9, 2022 with U.S. Patent Office.
U.S. Appl. No. 18/054,776, Specification, Claims, Abstract and Drawings as filed Nov. 11, 2022 with U.S. Patent Office.
U.S. Appl. No. 18/055,340, Specification, Claims, Abstract and Drawings as filed Nov. 14, 2022 with U.S. Patent Office.

* cited by examiner

Adapted from Chi 2007 & Glebe 2005

Hu = HBV24 mu or kappa
Ch = Chimeric HBV24 mu or kappa
K1 = HBV24K1 kappa mutant
M2 = HBV24M2 mu mutant
+ = IgM positive control 1 Native markers
2 HBV23G anti-S hIgG1
3 HBV23MJ anti-S-hIgM+J FIG. 2C  Expression & Assembly of 5a19 IgM
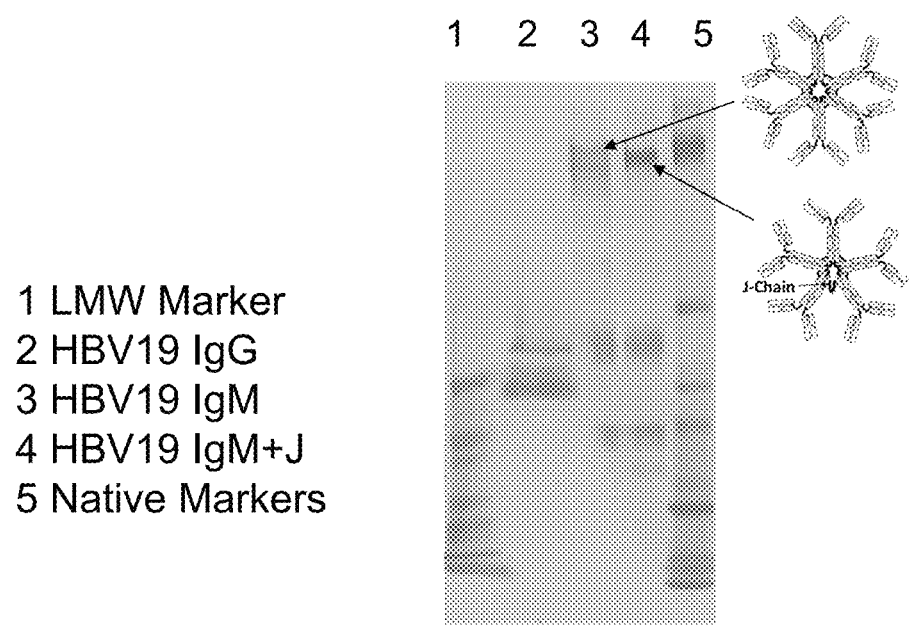
1 LMW Marker
2 HBV19 IgG
3 HBV19 IgM
4 HBV19 IgM+J
5 Native Markers

MULTI-VALENT HEPATITIS B VIRUS ANTIGEN BINDING MOLECULES AND USES THEREOF

CROSS REFERENCE TO RELATED APPLICATION

This application is a continuation of U.S. patent application Ser. No. 15/560,905, filed Sep. 22, 2017, which is a U.S. National Stage entry of PCT Patent Application No. PCT/US2016/024348, filed on Mar. 25, 2016, which claims priority benefit of the filing date of U.S. Provisional Application No. 62/137,881 filed Mar. 25, 2015, the disclosures of which applications are incorporated herein by reference in their entireties.

REFERENCE TO SEQUENCE LISTING SUBMITTED ELECTRONICALLY

This instant application contains a Sequence Listing which has been submitted electronically in ASCII format and is hereby incorporated by reference in its entirety. Said ASCII copy, created on Sep. 27, 2017, is named 5792-169946_SL.txt and is 146986 bytes in size.

BACKGROUND

Hepatitis B virus (HBV) belongs to the class of double stranded DNA viruses and is presently known to include four major serotypes (adr, adw, ayr, and ayw) and eight major genotypes (A though H). The serotypes are based on variations in envelope protein sequences while the eight genotypes are distinctly distributed across the world in specific geographical areas. Genotypic differences have been linked to disease severity and effectiveness of response to treatment (see Kramvis et al., *Vaccine*, 23(19):2409-23, 2005, and Magnius et al., *Intervirology*, 38(1-2):24-34, 1995).

The HBV genome is comprised of circular DNA that is partially double stranded. That is, there are portions of the genome that are single stranded. The longer portion of the HBV genome is 3020 to 3320 nucleotides in length, while the shorter portion is 1700 to 2800 nucleotides in length. The longer portion of the HBV genome is linked to the viral DNA polymerase.

HBV-infected cells can produce, in addition to infectious virus particles, spherical and filamentous non-infectious particles lacking a core. These non-infectious particles can outnumber infectious particles in an HBV-infected individual by as much as 1,000 to 100,000 fold (see Chai et al. *J. Virol.* 82:7812-7817, 2005).

There are five viral proteins produced by HBV, including the following:
 1. Envelope protein (also known as surface antigen, HBsAg, encoded by the S gene);
 2. Polymerase (pol, encoded by the P gene);
 3. Hepatitis B X-protein (HBxAg, X-antigen, encoded by the X gene);
 4. Nucleocapsid or core antigen (HBcAg, encoded by the C gene); and
 5. Precore (HBeAg, encoded by the core and Pre-C genes).

The HBsAg is produced in three sizes from the three independent start codons in the HBV genome. The Small, Medium and Large versions of this gene product are a combination of one or more of the three designated domains: (i) S alone (S), (ii) pre-S2 and S (M), or (iii) pre-S1 and pre-S2 and S (L) (FIG. 1A). Infectious particles most often possess all three versions of this antigen, and can enter hepatocytes via the interaction between pre-S1 protein (FIG. 1B) and the NTCP receptor (sodium taurocholate co-transporting polypeptide, or liver bile acid transporter, encoded by the SLC10A1 gene). Thus, the pre-S1 antigen is associated with infection and is preferentially expressed in infectious viral particles. (Hong et al., *Virology*, 318:134-141, 2004; Park et al., *Antiviral Res.*, 68:109-115, 2005).

HBeAg is the precore protein and is secreted. The precore protein has been shown to play an immune regulatory role. HBeAg has been found to regulate the immune response to the core antigen. (Chen et al., *Proc. Natl. Acad. Sci. USA*, 101:14913-14918, 2004).

While the functions of the capsid, polymerase and surface antigen proteins seem clear, the function of the "X" gene has yet to be fully elucidated, though it is known to play a role in the development of hepatocellular carcinoma (HCC). (Tang et al., *Cancer Sci.*, 97:977-983, 2006, Ng et al., *J. Gastroent.*, 46:974-990, 2011, and Kew, Michael C., *J. Gastro. Hepat.*, 26 Suppl. 1:144-152, 2011).

The hepatitis B virus is believed to have infected more than 2 billion people around the world. There are believed to be 350 to 400 million chronically or persistently infected individuals worldwide and HBV or complications from HBV infection results in 780,000 deaths per year worldwide. HBV is fifty to one hundred times more infectious than the human immunodeficiency virus (HIV). HBV is transmitted by exposure to infectious blood or body fluids. Symptoms of infection commonly include loss of appetite, fatigue, a low fever, jaundice, aches in muscles and joints, nausea and vomiting, yellow skin and dark urine. Some individuals are not able to completely clear the virus from their system, resulting in a chronic infection that can result in liver damage and cirrhosis. About 15 to 40% of chronic HBV patients develop liver cirrhosis and/or HCC. (Xu et al., *Canc. Lett.*, 345:216-222, 2014). The HBV viral genome persists in the genome of the host and can be reactivated after being cleared, leading to new HBV symptoms. The rate of liver cancer is much higher in those who have an HBV infection.

Both clearance and pathogenesis of the virus are mediated by the adaptive, or acquired, immune response. This includes both a humoral (antibody-mediated) immunity component and cell-mediated immune component. In particular, infection triggers response of virus-specific cytotoxic T lymphocytes (CTL), which produce most of the observed injury to liver tissue in chronic infections.

Many preventive strategies have been developed to combat HBV infection. Vaccines have been developed based on recombinant surface antigen of the virus. (See, WO 2014/0489101 and Shouval, D., *J. Hepatol.* 39 (Suppl. 1):70-76, 2003). In addition, an HBV immunoglobulin (HBIG) has been developed from human sera from high titer individuals. HBIG is typically provided to infants of HBV infected mothers to prevent transmission to the child. If HBIG is administered within 24 hours of known exposure, HBV infection can be prevented. HBIG is also commonly administered to HBV infected liver transplant patients to prevent re-infection of the new tissue.

Chronically infected individuals are candidates for therapy. However, there is presently no approved treatment known to clear chronic HBV infection. Available therapies can block further infection by precluding the virus from replicating. Various monoclonal antibodies and combination therapies have been investigated for the purpose of treating and/or curing HBV infection, including chronic HBV infection, but none have been commercialized.

The treatment options for chronic infection, e.g., interferon and lamivudine, are only modestly effective and are known to cause severe side effects. Despite efforts directed toward the development of therapies for treatment or prevention of HBV infection, there remains a continuing need to develop new therapies targeting HBV infection, e.g., chronic HBV infection.

SUMMARY

Disclosed are various embodiments of multimeric binding molecules that possess specificity for binding one or more hepatitis B antigens. This disclosure provides a multimeric binding molecule that includes at least two bivalent binding units, or variants or fragments thereof; where each binding unit includes at least two antibody heavy chain constant regions or fragments thereof, each associated with an antigen binding domain; where at least one antigen binding domain specifically binds to a hepatitis B virus (HBV) antigen expressed on the surface of infectious viral particles, on the surface if HBV infected cells, or a combination thereof, and where the binding molecule is more potent than a reference single bivalent binding unit that includes the same antigen binding domain that specifically binds to the HBV antigen. In certain aspects, the reference single bivalent binding unit is an IgG antibody.

In certain aspects, the binding molecule can be a dimeric binding molecule including two bivalent IgA binding units or fragments thereof and a J-chain or fragment or variant thereof, where each binding unit includes two IgA heavy chain constant regions or fragments thereof each associated with an antigen-binding domain. In certain aspects, the dimeric binding molecule can further include a secretory component, or fragment or variant thereof. In certain aspects, the IgA heavy chain constant regions or fragments thereof each include a Cα2 domain or a Cα3-tp domain, and can further include a Cα1 domain. In certain aspects, the IgA heavy chain constant region is a human IgA constant region. In certain aspects, each binding unit of a dimeric binding molecule provided herein can include two IgA heavy chains each including a VH situated amino terminal to the IgA constant region or fragment thereof, and two immunoglobulin light chains each including a VL situated amino terminal to an immunoglobulin light chain constant region.

In certain aspects the binding molecule can be a pentameric or a hexameric binding molecule including five or six bivalent IgM binding units, respectively, where each binding unit includes two IgM heavy chain constant regions or fragments thereof each associated with an antigen binding domain. In certain aspects the IgM heavy chain constant regions or fragments thereof each include a Cµ3 domain and a Cµ4-tp domain, and can further include a Cµ2 domain, a Cµ1 domain, or any combination thereof. In certain aspects a pentameric binding molecule is provided that further includes a J-chain, or fragment thereof, or variant thereof. In certain aspects at least one heavy chain constant region of a hexameric or pentameric binding molecule as provided herein is a human IgM constant region. In certain aspects each binding unit of a hexameric or pentameric binding molecule as provided herein includes two heavy chains each including a VH situated amino terminal to the constant region or fragment thereof, and two immunoglobulin light chains each including a VL situated amino terminal to an immunoglobulin light chain constant region.

In certain aspects, at least one binding unit of a dimeric, pentameric, or hexameric binding molecule, e.g., an IgM antibody provided herein includes two antigen binding domains that specifically bind to a hepatitis B virus (HBV) antigen expressed on the surface of infectious viral particles, on the surface of HBV-infected cells, or a combination thereof, and the two heavy chains within the binding unit are identical. In certain aspects, the two light chains within the binding unit are identical. In certain aspects, the light chain constant regions of the binding unit are human lambda constant regions or human kappa constant regions. In certain aspects the binding molecule includes at least three, at least four, at least five, at least six, at least seven, at least eight, at least nine, at least ten, at least eleven, or at least twelve antigen binding domains that specifically bind to a hepatitis B virus (HBV) antigen expressed on the surface of infectious viral particles, on the surface of HBV-infected cells, or a combination thereof. In certain aspects at least two, at least three, at least four, at least five, at least six, at least seven, at least eight, at least nine, at least ten, at least eleven or at least twelve of the binding domains are identical.

Where the binding molecule is pentameric, the binding molecule can further include a J-chain, or fragment thereof, or functional fragment thereof, or a functional variant thereof. In certain aspects, the J-chain or fragment thereof includes the amino acid sequence SEQ ID NO: 54 or a functional fragment thereof. In certain aspects, the J-chain or fragment thereof can further include a heterologous polypeptide. The heterologous polypeptide can be directly or indirectly fused to the J-chain or fragment thereof. In certain aspects the heterologous polypeptide can be indirectly fused to the J-chain or fragment thereof via a peptide linker. In certain aspects the peptide linker can include, e.g., at least 5 amino acids, but no more than 25 amino acids. In certain aspects the peptide linker consists of GGGGSGGGGSGGGGS (SEQ ID NO: 72). The heterologous polypeptide can be fused to or near the N-terminus of the J-chain or fragment thereof, the C-terminus of the J-chain or fragment thereof, or to both the N-terminus and C-terminus of the J-chain or fragment thereof. In certain aspects the heterologous polypeptide can include a binding domain, e.g., an antibody or antigen-binding fragment thereof. The antigen-binding fragment can be, for example, an Fab fragment, an Fab' fragment, an F(ab)$_2$ fragment, an Fd fragment, an Fv fragment, a single-chain Fv (scFv) fragment, a disulfide-linked Fv (sdFv) fragment, or any combination thereof. In certain aspects the heterologous polypeptide can specifically bind to CD3ε. For example in certain aspects the modified J-chain can include the amino acid sequence SEQ ID NO: 68 (V15J) or SEQ ID NO: 71 (J15V). Moreover in certain aspects, these particular modified J-chains can further include a signal peptide, where the modified J-chain then includes the amino acid sequence SEQ ID NO: 67 (V15J) or SEQ ID NO: 70 (J15V).

In certain aspects, the HBV antigen bound by a dimeric, pentameric, or hexameric binding molecule, e.g., an IgM antibody as provided herein is expressed on the surface of infectious viral particles, on the surface of HBV infected cells, or a combination thereof in higher density than the HBV antigen is expressed on non-infectious sub-viral particles. In certain aspects, the HBV antigen is a hepatitis B surface antigen (HBsAg), a precore antigen, a core antigen, an X-antigen, or any combination thereof. In certain aspects where the binding molecule binds to an HBsAg, it can include an S region (S), a pre-S2 and S region, or pre-S1, Pre-S2 and S regions, or fragments thereof.

In certain aspects, at least one antigen binding domain of a dimeric, pentameric, or hexameric binding molecule, e.g., an IgM antibody as provided herein includes the HCDR1, HCDR2, and HCDR3 regions, or the HCDR1, HCDR2, and HCDR3 regions containing one or two single amino acid substitutions, and the LCDR1, LCDR2, and LCDR3 regions, or the LCDR1, LCDR2, and LCDR3 regions containing one or two single amino acid substitutions, as contained in the VH and VL amino acid sequences SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively.

In certain aspects, at least one antigen binding domain of a dimeric, pentameric, or hexameric binding molecule, e.g., an IgM antibody as provided herein includes the HCDR1, HCDR2, and HCDR3 regions, or the HCDR1, HCDR2, and HCDR3 regions containing one or two single amino acid substitutions, of the VH amino acid sequence SEQ ID NO: 12 or SEQ ID NO: 13.

In certain aspects, at least one antigen binding domain of a dimeric, pentameric, or hexameric binding molecule, e.g., an IgM antibody as provided herein includes an antibody heavy chain variable region (VH) and an antibody light chain variable region (VL), where the VH and VL include, respectively, amino acid sequences that are at least 80%, at least 85%, at least 90%, at least 95% or 100% identical to SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76.

In certain aspects, at least one antigen binding domain of a dimeric, pentameric, or hexameric binding molecule, e.g., an IgM antibody as provided herein includes an antibody VH, where the VH includes an amino acid sequence at least 80%, at least 85%, at least 90%, at least 95% or 100% identical to SEQ ID NO: 12 or SEQ ID NO: 13.

In certain aspects the binding molecule as provided herein is a hexameric or pentameric IgM antibody or fragment thereof that includes an IgM heavy chain including the amino acid sequence SEQ ID NO: 58 and a light chain including the amino acid sequence SEQ ID NO: 59. In certain aspects the binding molecule as provided herein is a hexameric or pentameric IgM antibody or fragment thereof that includes an IgM heavy chain including the amino acid sequence SEQ ID NO: 63 and a light chain including the amino acid sequence SEQ ID NO: 59.

In certain aspects, a dimeric, pentameric, or hexameric binding molecule, e.g., an IgM antibody as provided herein can be more potent in virus neutralization, killing of infected cells, enhancing viral clearance, controlling HBV proliferation, latency, or maintenance in chronically-infected cells, than a reference single binding unit that includes the same HBV-binding antigen binding domains.

The disclosure further provides an isolated IgM antibody or fragment thereof that includes a J-chain, or functional fragment or variant thereof, and five binding units, each including two heavy chains and two light chains, where each heavy chain or fragment thereof that includes a human Mu constant region or fragment thereof, and the heavy chain variable region amino acid sequence SEQ ID NO: 62, and wherein each light chain can include a human kappa constant region and the light chain variable region amino acid sequence SEQ ID NO: 6; wherein the antibody or fragment thereof can assemble into a pentameric IgM antibody that can specifically bind to the pre-S1 region of HBV surface antigen. In certain aspects, the heavy chain of the IgM antibody or fragment thereof includes the amino acid sequence SEQ ID NO: 63, and the light chain of the IgM antibody or fragment thereof includes the amino acid sequence SEQ ID NO: 59. In certain aspects, the J-chain or fragment thereof includes the amino acid sequence SEQ ID NO: 54 or a functional fragment thereof. In certain aspects, the J-chain or fragment thereof can further include a heterologous polypeptide. The heterologous polypeptide can be directly or indirectly fused to the J-chain or fragment thereof. In certain aspects the heterologous polypeptide can be indirectly fused to the J-chain or fragment thereof via a peptide linker. In certain aspects the peptide linker can include, e.g., at least 5 amino acids, but no more than 25 amino acids. In certain aspects the peptide linker consists of GGGGSGGGGSGGGGS (SEQ ID NO: 72). The heterologous polypeptide can be fused to or near the N-terminus of the J-chain or fragment thereof, the C-terminus of the J-chain or fragment thereof, or to both the N-terminus and C-terminus of the J-chain or fragment thereof. In certain aspects the heterologous polypeptide can include a binding domain, e.g., an antibody or antigen-binding fragment thereof. The antigen-binding fragment can be, for example, an Fab fragment, an Fab' fragment, an F(ab)$_2$ fragment, an Fd fragment, an Fv fragment, a single-chain Fv (scFv) fragment, a disulfide-linked Fv (sdFv) fragment, or any combination thereof. In certain aspects the heterologous polypeptide can specifically bind to CD3c. For example in certain aspects the modified J-chain can include the amino acid sequence SEQ ID NO: 68 (V15J) or SEQ ID NO: 71 (J15V). Moreover in certain aspects, these particular modified J-chains can further include a signal peptide, where the modified J-chain then includes the amino acid sequence SEQ ID NO: 67 (V15J) or SEQ ID NO: 70 (J15V).

The disclosure further provides a composition that includes the dimeric, pentameric or hexameric binding molecule as provided herein or the isolated IgM antibody as provided herein.

This disclosure also provides a polynucleotide that includes a nucleic acid sequence that encodes a polypeptide subunit of the dimeric, pentameric, or hexameric binding molecule, e.g., the IgM antibody as provided herein, where the polypeptide subunit includes the IgM heavy chain constant region and at least the antibody VH portion of an antibody binding domain that specifically binds to a hepatitis B virus (HBV) antigen expressed on the surface of infectious viral particles, on the surface if HBV infected cells, or a combination thereof. In certain aspects, the polypeptide subunit includes a human IgA or IgM constant region or fragment thereof fused to the C-terminal end of a VH that includes: the HCDR1, HCDR2, and HCDR3 domains, or the HCDR1, HCDR2, and HCDR3 domains containing one or two single amino acid substitutions in one or more HCDRs, of the VH amino acid sequence SEQ ID NO: 1, SEQ ID NO: 2, SEQ ID NO: 4, SEQ ID NO: 5, SEQ ID NO: 7, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 26, SEQ ID NO: 30, SEQ ID NO: 32, SEQ ID NO: 34, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 62, SEQ ID NO: 73, or SEQ ID NO: 75; or an amino acid sequence at least 80%, at least 85%, at least 90%, at least 95% or 100% identical to SEQ ID NO: 1, SEQ ID NO: 2, SEQ ID NO: 4, SEQ ID NO: 5, SEQ ID NO: 7, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 26, SEQ ID NO: 30, SEQ ID NO: 32, SEQ ID NO: 34, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 62, SEQ ID NO: 73, or SEQ ID NO: 75.

This disclosure also provides a polynucleotide that includes a nucleic acid sequence that encodes a polypeptide subunit of the dimeric, pentameric, or hexameric binding molecule, e.g., an IgM antibody as provided herein, where the polypeptide subunit includes the antibody VL portion of an antibody binding domain that specifically binds to a hepatitis B virus (HBV) antigen expressed on the surface of infectious viral particles, on the surface of HBV-infected cells, or a combination thereof. In certain aspects the polypeptide subunit can include a human antibody light chain constant region or fragment thereof fused to the C-terminal end of a VL that includes the LCDR1, LCDR2, and LCDR3 domains, or the LCDR1, LCDR2, and LCDR3 domains containing one or two single amino acid substitutions in one or more LCDRs, of the VL amino acid sequence SEQ ID NO: 3, SEQ ID NO: 6, SEQ ID NO: 8, SEQ ID NO: 9, SEQ ID NO: 11, SEQ ID NO: 15, SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 74, or SEQ ID NO: 76; or an amino acid sequence at least 80%, at least 85%, at least 90%, at least 95% or 100% identical to SEQ ID NO: 3, SEQ ID NO: 6, SEQ ID NO: 8, SEQ ID NO: 9, SEQ ID NO: 11, SEQ ID NO: 15, SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 74, or SEQ ID NO: 76.

The disclosure further provides a composition that includes a polynucleotide that encodes a heavy chain and a polynucleotide that encodes a light chain. The polynucleotides that are included in the composition can be contained on a single vector, or can be situated on separate vectors. In certain aspects the composition can further include a polynucleotide that includes a nucleic acid sequence encoding a J-chain, or fragment thereof, or variant thereof, which can be on an entirely separate vector or on the same vector or vectors as either the heavy chain encoding polynucleotide and/or the light chain encoding polynucleotide.

The one, two, or more vectors described above are also provided by the disclosure.

In an additional aspect, the disclosure provides a host cell that includes the provided polynucleotide, the provided composition, or the provided vector or vectors, where the host cell can express a dimeric, pentameric, or hexameric binding molecule as provided herein, e.g., the isolated IgM antibody provided herein, or a subunit thereof. The disclosure also provides a method of producing a dimeric, pentameric, or hexameric binding molecule as provided herein, e.g., the isolated IgM antibody as provided herein, where the method includes culturing the provided host cell, and recovering the binding molecule.

The disclosure further provides a method of controlling hepatitis B virus (HBV) proliferation, latency, or maintenance in chronically-infected cells, e.g., controlling viral attachment, infectivity, replication, latency, egress, etc., where the method includes contacting a mixture of HBV and HBV-susceptible cells with the dimeric, pentameric, or hexameric binding molecule as provided herein, e.g., the isolated IgM antibody provided herein, where HBV replication is controlled at a greater potency than an IgG antibody including at least one antigen binding domain in common with the binding molecule.

The disclosure further provides a method of treating a disease or condition caused by or exacerbated by hepatitis B virus (HBV) infection in a patient, where the method includes administering to a patient infected with HBV or susceptible to HBV infection the dimeric, pentameric, or hexameric binding molecule as provided herein, e.g., the isolated IgM antibody provided herein. In certain aspects, the binding molecule can be more potent than a reference single binding unit antibody, e.g., an IgG antibody that includes at least one antigen binding domain that specifically binds to the same HBV antigen as the binding molecule or IgM antibody. In certain aspects the disease or condition can be, e.g., acute hepatitis, chronic hepatitis, liver inflammation, cirrhosis of the liver, liver failure, hepatocellular carcinoma (HCC), or any combination thereof. In certain aspects, the patient can exhibit one or more HBV disease symptoms such as, but not limited to increased viral load, virus shedding, abdominal pain, dark urine, fever, joint pain, loss of appetite, nausea and vomiting, weakness and fatigue, jaundice, or a combination thereof.

The disclosure further provides a method for identifying a binding molecule that binds to the surface of infectious virus particles, the surface of virus-infected cells, or a combination thereof with greater affinity, greater avidity, or a combination thereof, than to non-infectious virus particles, where the method includes: (a) contacting a test binding molecule with an infectious viral particle and measuring the affinity or avidity of the test binding molecule for binding to the infectious viral particle; (b) contacting the test binding molecule with a non-infectious version of the virus particle and measuring the affinity or avidity of the test binding molecule for binding to the non-infectious particle; (c) comparing the results of steps (a) and (b); and (d) identifying test compounds in which the affinity or avidity measured in step (a) is higher than the affinity or avidity measured in step (b).

In another aspect, the disclosure provides a method for identifying a binding molecule that binds to the surface of a cell infected with a virus of interest with greater affinity, greater avidity, or a combination thereof, than to a cell not infected with virus, where the method includes: (a) contacting a test binding molecule with a virus-infected cell and measuring the affinity or avidity of the test binding molecule for binding to the virus-infected cell; (b) contacting the test binding molecule with a cell not infected with virus and measuring the affinity or avidity of the test binding molecule for binding to the non-infected cell, where the non-infected cell is identical to the virus-infected cell except that it is not infected; (c) comparing the results of steps (a) and (b); and (d) identifying test compounds in which the affinity or avidity measured in step (a) is higher than the affinity or avidity measured in step (b).

In another aspect the disclosure provides a method for identifying a binding molecule that binds to the surface of infectious hepatitis B virus (HBV) viral particles, the surface of HBV-infected cells, or a combination thereof with greater affinity, greater avidity, or a combination thereof, than to HBV subviral particles, where the method includes: (a) contacting a test binding molecule with an HBV viral particle and measuring the affinity or avidity of the test binding molecule for binding to an HBV viral particle; (b) contacting the test binding molecule with an HBV subviral particle and measuring the affinity or avidity of the test binding molecule for binding to an HBV subviral particle; (c) comparing the results of steps (a) and (b); and (d) identifying test compounds in which the affinity or avidity measured in step (a) is higher than the affinity or avidity measured in step (b).

In another aspect the disclosure provides a method for identifying a binding molecule that binds to the surface of a cell infected with hepatitis B virus (HBV) with greater affinity, greater avidity, or a combination thereof, than to a cell not infected with HBV, where the method includes: (a) contacting a test binding molecule with an HBV-infected cell and measuring the affinity or avidity of the test binding molecule for binding to the HBV-infected cell; (b) contacting the test binding molecule with a cell not infected with HBV and measuring the affinity or avidity of the test binding molecule for binding to a cell not infected with HBV, where the non-infected cell is identical to the HBV-infected cell except that it is not infected; (c) comparing the results of steps (a) and (b); and (d) identifying test compounds in which the affinity or avidity measured in step (a) is higher than the affinity or avidity measured in step (b). In certain aspects the HBV-infected cell is a human cell. In certain aspects the test binding molecule is the dimeric, pentameric, or hexameric binding molecule, e.g., an IgM antibody provided herein.

BRIEF DESCRIPTION OF THE FIGURES

FIG. 2C: SDS polyacrylamide gel showing expression products from HBV19 IgG and IgM constructs.

DETAILED DESCRIPTION

Definitions

Figure 1A:
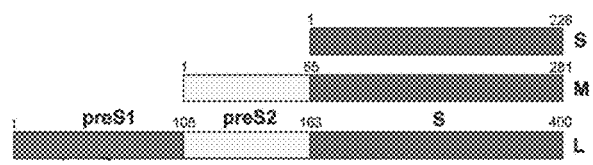
FIG. 1A: linear structure of the HBV surface protein.

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides that retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies provided herein do not abrogate the binding of the polypeptide or antibody containing the amino acid sequence, to the antigen to which the binding molecule binds. Methods of identifying nucleotide and amino acid conservative substitutions that do not eliminate antigen-binding are well-known in the art (see, e.g., Brummell et al., *Biochem.* 32:1180-1 187 (1993); Kobayashi et al., *Protein Eng.* 12(10):879-884 (1999); and Burks et al., *Proc. Natl. Acad. Sci. USA* 94: 412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, that has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions that encode secretory or signal peptides, which direct the secretion of a polypeptide encoded by a polynucleotide as disclosed herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

Disclosed herein are certain binding molecules, or antigen-binding fragments, variants, or derivatives thereof. Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

The terms "binding domain" and "antigen binding domain" are used interchangeably herein and refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain."

Other antigen binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable region of a heavy chain (for camelid species) or at least the variable region of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and can include a J-chain and/or a secretory component, or an IgM antibody that includes ten or twelve complete heavy chains and ten or twelve complete light chains and can include a J-chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$ or $\alpha1$-$\alpha2$)). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody or antigen-binding fragment thereof that corresponds to a standard immunoglobulin structure, i.e., two heavy chains or fragments thereof and two light chains or fragments thereof, or two heavy chains or fragments thereof derived, e.g., from a camelid or condricthoid antibody. In certain aspects, e.g., where the binding molecule is a single binding unit IgG antibody or antigen-binding fragment thereof, the terms "binding molecule" and "binding unit" are equivalent. In other aspects, e.g., where the binding molecule is an IgA dimer, an IgM pentamer, or an IgM hexamer, the binding molecule is "multimeric" and comprises two or more "binding units." Two in the case of an IgA dimer, or five or six in the case of an IgM pentamer or hexamer, respectively. A binding unit need not include full-length antibody heavy and light chains, but will typically be bivalent, i.e., will include two "antigen binding domains," as defined below. Certain binding molecules provided in this disclosure are pentameric or hexameric, and include five or six bivalent binding units that include IgM constant regions or fragments thereof.

As used herein, a binding molecule comprising two or more binding units, e.g., two, five, or six binding units, can be referred to as "multimeric." The term "multimeric" means possessing more than one unit. Thus, for example, a "multimeric binding molecule" will possess more than one binding unit. A multimeric binding molecule could possess as many as two, three four, five or even six or more binding units.

The term "native sequence J-chain" or "native J-chain" as used herein refers to J-chain of native sequence IgM or IgA antibodies of any animal species, including mature human J-chain, the amino acid sequence of which is presented as SEQ ID NO: 54.

The term "modified J-chain" is used herein to refer to variants of native sequence J-chain polypeptides comprising a heterologous moiety, e.g., a heterologous polypeptide, e.g., an extraneous binding domain introduced into the native sequence. The introduction can be achieved by any means, including direct or indirect fusion of the heterologous polypeptide or other moiety or by attachment through a peptide or chemical linker. The term "modified human J-chain" encompasses, without limitation, a native sequence human J-chain of the amino acid sequence of SEQ ID NO: 54 or functional fragment thereof modified by the introduction of a heterologous moiety, e.g., a heterologous polypeptide, e.g., an extraneous binding domain. In certain aspects the heterologous moiety does not interfere with efficient polymerization of IgM into a pentamer or IgA into a dimer and binding of such polymers to a target. Exemplary modified J-chains can be found, e.g., in PCT Publication No. WO 2015/153912, which is incorporated herein by reference in its entirety.

The terms "valency," "bivalent," "multivalent" and grammatical equivalents, refer to the number of antigen binding domains in given binding molecule or binding unit. As such, the terms "bivalent", "tetravalent", and "hexavalent" in reference to a given binding molecule denote the presence of two antigen binding domains, four antigen binding domains, and six antigen binding domains, respectively. In a typical IgM-derived binding molecule, each binding unit is bivalent, whereas the binding molecule itself can have 10 or 12 valencies. A bivalent or multivalent binding molecule can be monospecific, i.e., all of the antigen binding domains are the same, or can be bispecific or multispecific, e.g., where two or more antigen binding domains are different, e.g., bind to different epitopes on the same antigen, or bind to entirely different antigens.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three dimensional structural characteristics, and or specific charge characteristics. An epitope is a region of a target that is bound by an antibody.

"Multispecific binding molecules or antibodies" or "bispecific binding molecules or antibodies" refer to binding molecules, antibodies, or antigen-binding fragments thereof that have the ability to specifically bind to two or more different epitopes on the same or different target(s). "Monospecific" refers to the ability to bind only one epitope.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Antibody light and heavy chains are divided into regions of structural and functional homology. The terms "constant" and "variable" are used functionally. In this regard, it will be appreciated that the variable regions (which can be called "variable domains" interchangeably herein) of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or aminoterminus of the antibody. The N-terminal portion is a variable region and at the C-terminal portion is a constant region; the CH3 (or CH4 in the case of IgM) and CL domains are at the carboxy-terminus of the heavy and light chain, respectively.

A "full length IgM antibody heavy chain" is a polypeptide that includes, in N-terminal to C-terminal direction, an antibody heavy chain variable region (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4), which can also include a tailpiece.

A "full length IgA antibody heavy chain" is a polypeptide that includes, in N-terminal to C-terminal direction, an antibody heavy chain variable region (VH), an antibody constant heavy chain constant domain 1 (CA1 or Cα1), an antibody heavy chain constant domain 2 (CA2 or Cα2), an antibody heavy chain constant domain 3 (CA3 or Cα3), and a tailpiece. The structure of monomeric and secretory IgA is described, e.g., in Woof, J M and Russell, MW, *Mucosal Immunology* 4:590-597 (2011).

As indicated above, a variable region, i.e., the "antigen binding domain," allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. More specifically, the antigen binding site is defined by three CDRs on each of the VH and VL chains. Certain antibodies form larger structures. For example, IgA can form a molecule that includes two H2L2 units and a J-chain, all covalently connected via disulfide bonds, and IgM can form a pentameric or hexameric molecule that includes five or six H2L2 units and, in some embodiments, a J-chain covalently connected via disulfide bonds. In certain embodiments, polymeric IgA and IgM molecules can also contain a secretory component that can also be covalently connected via disulfide bonds.

The six "complementarity determining regions" or "CDRs" present in an antibody antigen binding domain are short, non-contiguous sequences of amino acids that are specifically positioned to form the antigen binding domain as the antibody assumes its three dimensional configuration in an aqueous environment. The remainder of the amino acids in the antigen binding domain, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids that encompass the CDRs as defined by each of the above cited references are set forth below in Table 1 as a comparison. The exact amino acid numbers that encompass a particular CDR will vary depending on the sequence and size of the CDR. Those skilled in the art can routinely determine that amino acids comprise a particular CDR given the variable region amino acid sequence of the antibody.

TABLE 1

CDR Definitions*

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Immunoglobulin variable domains can also be analyzed, e.g., using the IMGT information system (www://imgt.cines.fr/) (IMGT®/V-Quest) to identify variable region segments, including CDRs. (See, e.g., Brochet et al., *Nucl. Acids Res.*, 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule. Also contemplated are immunoglobulin new antigen receptor (IgNAR) isotypes that are bivalent and comprise a single chain that includes an IgNAR variable domain (VNAR). (See, Walsh et al., *Viral.*, 411: 132-141, 2011).

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5\times10^{-2}$ sec$^{-1}$, $10^{-2}$ sec$^{-1}$, $5\times10^{-3}$ sec$^{-1}$, $10^{-3}$ sec$^{-1}$, $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^3$ M$^{-1}$ sec$^{-1}$, $5\times10^3$M$^{-1}$ sec$^{-1}$, $10^4$ M$^{-1}$ sec$^{-1}$, $5\times10^4$ M$^{-1}$ sec$^{-1}$, $10^5$ M$^{-1}$ sec$^{-1}$, $5\times10^5$ M$^{-1}$ sec$^{-1}$, $10^6$M$^{-1}$ sec$^{-1}$, or $5\times10^6$M$^{-1}$ sec$^{-1}$ or $10^7$M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of its binding affinity to an antigen. For example, a binding molecule can bind to an antigen with a dissociation constant or K$_D$ no greater than $5\times10^{-2}$ M, $10^{-2}$ M, $5\times10^{-3}$M, $10^{-3}$M, $5\times10^{-4}$M, $10^{-4}$M, $5\times10^{-5}$M, $10^{-5}$M, $5\times10'$M, $10'$M, $5\times10^{-7}$M, $10^{-7}$M, $5\times10^{-8}$M, $10^{-8}$M, $5\times10^{-9}$M, $10^{-9}$M, $5\times10^{-10}$ M, $10^{-10}$ M, $5\times10^{-11}$ M, $10^{-11}$ M, $5\times10^{-12}$ M, $10^{-12}$ M, $5\times10^{-13}$M, $10^{-13}$M, $5\times10^{-14}$M, $10^{-14}$ M, $5\times10^{-15}$M, or $10^{-15}$M.

Antibody fragments including single-chain antibodies or other antigen binding domains can exist alone or in combination with one or more of the following: hinge region, CH1, CH2, CH3, or CH4 domains, J-chain, or secretory component. Also included are antigen-binding fragments that can include any combination of variable region(s) with one or more of a hinge region, CH1, CH2, CH3, or CH4 domains, a J-chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" or "heavy chain domain" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, in addition to a VH domain, a CH1 domain; CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J-chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

The heavy chain subunits of a binding molecule, e.g., an antibody or fragment thereof, can include domains derived from different immunoglobulin molecules. For example, a heavy chain subunit of a polypeptide can include a CH1 domain derived from an IgG1 molecule and a hinge region derived from an IgG3 molecule. In another example, a heavy chain subunit can include a hinge region derived, in part, from an IgG1 molecule and, in part, from an IgG3 molecule. In another example, a heavy chain subunit can comprise a chimeric hinge derived, in part, from an IgG1 molecule and, in part, from an IgG4 molecule.

As used herein, the term "light chain subunit" or "light chain domain" includes amino acid sequences derived from an immunoglobulin light chain. The light chain subunit includes at least one of a VL or CL (e.g., Cκ or Cλ) domain.

Binding molecules, e.g., antibodies or antigen binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH region" or "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of a typical IgG heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat E A et al., op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain in IgG, IgA, and IgD heavy chains. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group. In certain IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody", or "bispecific antibody" refer to an antibody that has antigen binding domains that are specific for two or more different epitopes within a single antibody molecule (or "binding unit"). Other binding molecules in addition to the canonical antibody structure can be constructed with two different binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody. Thus, a bispecific binding molecule that is multimeric could potentially possess several different antigen binding domains, each with a different specificity. For instance, an IgM binding molecule would be considered multimeric, containing five or six binding units, and each binding unit possessing possibly two antigen binding domains. In such an IgM binding molecule, there could be as many as two, three, four, five, six, seven, eight, nine, ten, eleven, or even twelve different specificities, since each antigen binding domain can bind a different, distinguishable epitope.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide.

A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain. For example in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a binding molecule such as an antibody, comprising one or more antigen binding domains. Such binding molecules, e.g., antibodies, can be used, e.g., for a diagnostic procedures and/or for treatment or prevention of a disease.

As used herein, hepatitis B surface antigen, or "HBsAg" refers to the surface glycoprotein of HBV. HBsAg produced in three sizes from the three independent start codons in the HBV genome. The Small, Medium and Large versions of this gene product are a combination of one or more of the three designated domains: (i) S alone (S), (ii) pre-S2 and S (M), or (iii) pre-S1 and pre-S2 and S (L) (FIG. 1A). HBsAg varies amongst serotypes and strains, but an exemplary "L" version of HBsAg comprises the following amino acid sequence:

(SEQ ID NO: 79)
<u>MGGWSSKPRKGMGTNLSVPNPLGFFPDHQLDPAFGANSNNPDW</u>

<u>DFNPIKDHWPAANQVGVGAFGPGLTPPHGGILGWSPQAQGILTTV</u>

<u>STIPPPASTNRQSGRQPTPISPPLRDSHPQAM</u><u>QWNSTAFHQALQDP</u>

<u>RVRGLYFPAGGSSSGTVNPAPNIASHISSISARTGDPVTN</u>MENITSG

FLGPLLVLQAGFFLLTRILTIPQSLDSWWTSLNFLGGSPVCLGQNS

QSPTSNHSPTSCPPICPGYRWMCLRRFIIPLFILLLCLIPLLVLLDYQ

GMLPVCPLIPGSTTTSTGPCKTCTTPAQGNSMFPSCCCTKPTDGNC

TCIPIPSSWAFAKYLWEWASVRFSWLSLLVPFVQWFVGLSPTVWL

SAIWMMWYWGPSLYSIVSPFIPLLPIFFCLWVYI.

The preS1 region is underlined, and the preS2 region is double-underlined. The precursor HBsAg, including the signal peptide, is presented below:

)SEQ ID NO: 78)
MEWSWVFLFFLSVTTGVHSMGGWSSKPRKGMGTNLSVPNPLGFF

PDHQLDPAFGANSNNPDWDFNPIKDHWPAANQVGVGAFGPGLTP

PHGGILGWSPQAQGILTTVSTIPPPASTNRQSGRQPTPISPPLRDSHP

QAMQWNSTAFHQALQDPRVRGLYFPAGGSSSGTVNPAPNIASHIS

SISARTGDPVTNMENITSGFLGPLLVLQAGFFLLTRILTIPQSLDSW

WTSLNFLGGSPVCLGQNSQSPTSNHSPTSCPPICPGYRWMCLRRFI

-continued
```
IFLFILLLCLIFLLVLLDYQGMLPVCPLIPGSTTTSTGPCKTCTTPAQ

GNSMFPSCCCTKPTDGNCTCIPIPSSWAFAKYLWEWASVRFSWLS

LLVPFVQWFVGLSPTVWLSAIWMMWYWGPSLYSIVSPFIPLLPIFF

CLWVYI.
```

As used herein the "PreS1 region" of the HBsAg refers to the 108-amino acid N-terminus of the HBsAg, comprising an amino acid sequence at least 70%, at least 75%, at least 80%, at least 85%, at least 90%, at least 95%, or 100% identical to the amino acid sequence:

```
                                          (SEQ ID NO: 60)
MGGWSSKPRQGMGTNLSVPNPLGFFPDHQLDPAFGANSNNPDWDFNPNK

DQWPEANQVGAGAFGPGFTPPHGGLLGWSPQAQGILTTVPAAPPPASTN

RQSGRQPTPISPPLRDSHPQA.
```

Figure 1B:
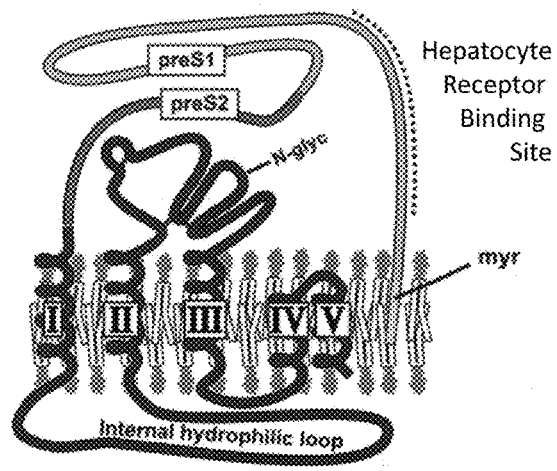
FIG. 1B: conformation of the HBV surface protein in a membrane.

SEQ ID NO: 60 is derived from the ad serotype of HBV, but this region of HBsAg is conserved across HBV serotypes. Neutralizing monoclonal antibodies have been shown to bind to the region spanning amino acids 20-47 (underlined). For example, antibodies related to the murine antibody KR127 (see, e.g., U.S. Pat. Nos. 7,115,723, 8,420,353, Hong et al., Virol., 318:131-141, 2004, and Kim, J. H., et al. FEBS Letters 589:193-200 (2015)) bind to an epitope within amino acids 37-47 of SEQ ID NO: 60. Monoclonal antibody 2D028 (WO 2011/045079A1) binds to an epitope within amino acids 38 to 47 of SEQ ID NO: 60. Another Pre-S1 antibody, F35.25 (Petit, et al., Mol Immunol. 1989 June; 26(6):531-7) binds to an epitope within amino acids 32-53 of SEQ ID NO: 60). Another Pre-S1 antibody, 5a19 (Pizarro, et al., FEBS Letters 509:463-468 (2001)) binds to an epitope within amino acids 37-43 of the ay serotype of pre-S1 (NTANPDW, SEQ ID NO: 77). The pre-S1 region is involved in hepatocyte receptor binding (FIG. 1A and FIG. 1B).

As used herein, the hepatitis B X protein or X antigen (HBxAg) refers the 154 amino acid X protein produced by hepatitis B virus. HBxAg comprises an amino acid sequence at least 70%, at least 75%, at least 80%, at least 85%, at least 90%, at least 95%, or 100% identical to the amino acid sequence:

```
                                          (SEQ ID NO: 61)
MAARVCCQLDPARDVLCLRPVGAESRGRPVSGPFGTLPSPSSSAVPADH

GAHLSLRGLPVCAFSSAGPCALRFTSARRMETTVNAHQVLPKVLHKRTL

GLSAMSTTDLEAYFKDCLFKDWEELGEEIRLKVFVLGGCRHKLVCSPAP

CNFFTSA.
```

The protein can be involved in the development of hepatocellular carcinoma (HCC) (Seifer, M., et al., J Hepatology; 13 (suppl. 4): S61-S65). Antibodies to HBxAg have been shown to reduce tumor size and improve survival in mice with HCC tumors (Li et al. Zhonghua Yi Xue Za Zhi. 1996 April; 76(4):271-4).

IgM Binding Molecules

IgM is the first immunoglobulin produced by B cells in response to stimulation by antigen, and is present at around 1.5 mg/ml in serum with a half-life of 5 days. IgM is typically multimeric, e.g., a pentameric or hexameric molecule. Thus, IgM molecules are "multimeric" binding molecules. Each of the five, or six, IgM binding units includes two light and two heavy chains. While IgG contains three heavy chain constant domains (CH1, CH2 and CH3), as explained above, the heavy (0 chain of IgM additionally contains a fourth constant domain (CH4), that includes a C-terminal "tailpiece." The human IgM constant region typically comprises the amino acid sequence SEQ ID NO: 53. The human Cµ1 region ranges from about amino acid 5 to about amino acid 102 of SEQ ID NO: 53; the human Cµ2 region ranges from about amino acid 114 to about amino acid 205 of SEQ ID NO: 53, the human Cµ3 region ranges from about amino acid 224 to about amino acid 319 of SEQ ID NO: 53, the Cµ4 region ranges from about amino acid 329 to about amino acid 430 of SEQ ID NO: 53, and the tailpiece ranges from about amino acid 431 to about amino acid 453 of SEQ ID NO: 53. The amino acid sequence of the human IgM constant region (SEQ ID NO: 53) is provided below:

```
GSASAPTLFPLVSCENSPSDTSSVAVGCLAQDFLPDSITLSWKYKNNSD

ISSTRGFPSVLRGGKYAATSQVLLPSKDVMQGTDEHVVCKVQHPNGNKE

KNVPLPVIAELPPKVSVFVPPRDGFFGNPRKSKLICQATGFSPRQIQVS

WLREGKQVGSGVTTDQVQAEAKESGPTTYKVTSTLTIKESDWLGQSMFT

CRVDHRGLTFQQNASSMCVPDQDTAIRVFAIPPSFASIFLTKSTKLTCL

VTDLTTYDSVTISWTRQNGEAVKTHTNISESHPNATFSAVGEASICEDD

WNSGERFTCTVTHTDLPSPLKQTISRPKGVALHRPDVYLLPPAREQLNL

RESATITCLVTGFSPADVFVQWMQRGQPLSPEKYVTSAPMPEPQAPGRY

FAHSILTVSEEEWNTGETYTCVAHEALPNRVTERTVDKSTGKPTLYNVS

LVMSDTAGTCY
```

An IgM binding molecule can comprise five binding units (each an "IgM binding unit") that can form a complex with an additional small polypeptide chain (the J-chain) to form a pentameric IgM binding molecule. The human J-chain comprises the amino acid sequence SEQ ID NO: 54. Without the J-chain, IgM binding units typically assemble into a hexameric IgM binding molecule. While not wishing to be bound by theory, the assembly of IgM binding units into a hexameric or pentameric binding molecule is thought to involve the Cµ3 and Cµ4 domains. Accordingly, a hexameric or pentameric IgM binding molecule provided in this disclosure typically includes IgM constant regions that include at least the Cµ3 and Cµ4 domains. The amino acid sequence of the human J-chain (SEQ ID NO: 54) is provided below:

```
MKNHLLFWGVLAVFIKAVHVKAQEDERIVLVDNKCKCARITSRIIRSSE

DPNEDIVERNIRIIVPLNNRENISDPTSPLRTRFVYHLSDLCKKCDPTE

VELDNQIVTATQSNICDEDSATETCYTYDRNKCYTAVVPLVYGGETKMV

ETALTPDACYPD
```

An IgM heavy chain constant region can additionally include a Cµ2 domain or a fragment thereof, a Cµ1 domain or a fragment thereof, and/or other IgM heavy chain domains. In certain aspects, a binding molecule as provided herein can include a complete IgM heavy (µ) chain constant domain, e.g., SEQ ID NO: 53, or a variant, derivative, or analog thereof.

Pentameric or Hexameric IgM HBV Binding Molecules

This disclosure provides a pentameric or hexameric HBV binding molecule, i.e., a binding molecule possessing five or six "binding units" as defined herein, which can specifically bind to an HBV antigen, e.g., HBsAg, e.g., the pre-S1 region of HBsAg. A binding molecule as provided herein can possess improved binding characteristics or biological activity as compared to a binding molecule composed of a single binding unit, e.g., an IgG antibody. In other words, the pentameric or hexameric IgM binding molecule provided herein can in some embodiments enhance viral clearance, and be more potent, e.g., as compared with a reference single binding unit comprising just two HBV-specific antigen binding domains. The term "improved binding characteristics" is further clarified as follows. The pentameric or hexameric IgM binding molecule provided herein, when administered to an individual in need thereof, can exhibit an activity that is empirically determined to be stronger, more potent, or require less binding molecule by mass or molar equivalents, to (i) neutralize, e.g., reduce the infectivity of an infectious HBV virion, (ii) reduce the number of HBV-infected cells (including HCC cells, latently infected cells, and chronically infected cells), (iii) prevent HBV infection, (iv) enhance viral clearance, e.g., through enhanced killing of infected cells, and/or (v) improve the signs and symptoms of HBV infection, as compared with an single, i.e. non-multimeric, binding molecule comprising just one binding unit that possesses antigen binding domains identical in sequence to those of the pentameric or hexameric IgM binding molecule provided herein.

A binding molecule as provided herein can likewise possess distinctive characteristics compared to multivalent binding molecules composed of synthetic or chimeric structures. For example, use of human IgM constant regions can afford reduced immunogenicity and thus increased safety relative to a binding molecule containing chimeric constant regions or synthetic structures. Moreover, an IgM-based binding molecule can consistently form hexameric or pentameric oligomers resulting in a more homogeneous expression product. Superior complement fixation can also be an advantageous effector function of IgM-based binding molecules.

The reference single binding unit referred to above can be an IgG binding unit. The reference IgG binding unit can be of any isotype, such as IgG1, IgG2, IgG3, or IgG4, etc. The reference binding unit is typically from the same animal. Thus if the multimeric binding molecule is human, the reference single binding unit would also be human, but not necessarily human. That is, the reference single binding unit can be a humanized antibody of the IgG type. Conversely, if the multimeric binding molecule is a rabbit binding molecule, the reference single binding unit would also be a rabbit binding unit. Further, if the multimeric binding molecule is comprised of one or more binding unit fragments, then the reference single binding unit would also be an equivalent single binding unit fragment. In other words, the reference single binding unit is otherwise identical in sequence and structure to the binding units contained in the multimeric binding molecule except that the reference single binding unit is an equivalent single binding unit.

In certain aspects, the disclosure provides a pentameric or hexameric binding molecule comprising five or six binding units, respectively, where each binding unit includes two IgM heavy chain constant regions or fragments thereof. In certain aspects, the two IgM heavy chain constant regions are human heavy chain constant regions. In some embodiments, the antigen binding domains in the IgM binding molecule are human in origin, or humanized, or a combination thereof.

Where the multimeric binding molecule provided herein is pentameric, the binding molecule can further comprise a J-chain, or functional fragment thereof, or variant thereof. Where the pentameric IgM binding molecule contains a J-chain, the J-chain can be of the same species as the IgM binding molecule. That is, if the pentameric IgM binding molecule is human, the J-chain can also be human. In certain aspects, the J-chain is a modified J-chain comprising a heterologous moiety or one or more heterologous moieties, e.g., a heterologous polypeptide sequence, e.g., an extraneous binding domain introduced into the native sequence. In certain aspects the extraneous binding domain specifically binds to CD3, e.g., CD3ε. In certain aspects the mature modified J-chain comprises V15J (SEQ ID NO: 68) or J15V (SEQ ID NO: 71).

An IgM heavy chain constant region can include one or more of a Cμ1 domain, a Cμ2 domain, a Cμ3 domain, and/or a Cμ4 domain, provided that the constant region can serve a desired function in the binding molecule, e.g., associate with second IgM constant region to form an antigen binding domain, or associate with other binding units to form a hexamer or a pentamer. In certain aspects the two IgM heavy chain constant regions or fragments thereof within an individual binding unit each comprise a Cμ3 domain or fragment thereof, a Cμ4 domain or fragment thereof, a tailpiece (TP) or fragment thereof, or any combination of a Cμ3 domain a Cμ domain, and a TP or fragment thereof. In certain aspects the two IgM heavy chain constant regions or fragments thereof within an individual binding unit each further comprise a Cμ2 domain or fragment thereof, a Cμ1 domain or fragment thereof, or a Cμ1 domain or fragment thereof and a Cμ2 domain or fragment thereof.

In certain aspects each of the two IgM heavy chain constant regions in a binding unit is associated with an antigen binding domain, for example an Fv portion of an antibody, e.g., a VH and a VL of a human or murine antibody. In certain aspects, at least one antigen binding domain of a binding molecule as provided herein is a cross-reactive HBV antigen binding domain, e.g., an antigen binding domain that can specifically bind to two, three, four, or more HBV subtypes. In other embodiments, an IgM binding molecule as provided herein can comprise binding units wherein each binding unit possesses a different and distinguishable specificity. Thus, a pentameric IgM binding molecule could possess as many as five different specificities and thereby bind to every different HBV subtype presently known. Further, because each binding unit of a pentameric IgM binding molecule possesses two antigen binding domains, and because each of these two antigen binding domains can independently bind a different antigen or different epitope on the same antigen, a pentameric IgM binding molecule can bind as many as two, three, four, five, six, seven, eight, nine or even ten different antigens or epitopes, across different HBV subtypes. Likewise, a hexameric IgM binding molecule can comprise binding units wherein each binding unit possesses a different and distinguishable specificity. Thus, a hexameric IgM binding molecule could possess as many as twelve different specificities and thereby bind to every different HBV subtype presently known. Further, because each binding unit of a hexameric IgM binding molecule possess two antigen binding domains, and because each of these two antigen binding domains can independently bind a different antigen or different epitope on the same antigen, a hexameric IgM binding molecule as disclosed herein can bind as many as two, three, four, five, six, seven, eight, nine, ten, eleven or even twelve different antigens or epitopes, across different HBV subtypes.

In certain aspects, at least one antigen binding domain binds to the S region, the pre-S2 region, and/or the pre-S1 region of the HBV virion surface envelope protein (HBsAg), or the HBV X protein. In certain embodiments, at least one antigen binding domain specifically binds to the pre-S1 region. In some aspects the multimeric binding molecule binds to an HBV antigen that comprises pre-S1, pre-S2 and S. In some embodiments the HBV antigen is pre-S1 and pre-S2, or pre-S1 and S, or pre-S2 and S. The binding unit that binds to the pre-S1 antigen can possess one or more different specificities for the pre-S1 antigen. That is, at least one binding unit of a multimeric binding molecule provided herein is specific for pre-S1 protein of the HBV envelope protein and because each binding unit can possess as many as two antigen binding domains, each antigen binding domain can bind to different and distinguishable epitopes on the pre-S1 protein. In other embodiments, when the multimeric binding molecule comprises more than one binding unit, each binding unit can independently be specific for a different HBV antigen. Thus, in a multimeric binding molecule comprising at least two binding units, one binding unit can possess specificity for pre-S1 antigen, another binding unit can possess specificity for S antigen, etc. Alternatively, all of the binding units can possess identical specificity for pre-S1, for example. Thus, just as each binding unit can be comprised of different antigen binding domains, a multimeric binding molecule can possess one or more specificities for different HBV antigens. In some aspects, all binding units of a multimeric binding molecule possess specificity for pre-S1 antigen.

HBV antigen targets for the binding units of multimeric binding molecule provided herein can be expressed on the surface of an infectious HBV virion, on the surface of HBV-infected cells, or a combination thereof in higher density than the HBV antigen is expressed on non-infectious sub-viral particles. For instance, it is known that pre-S1 is expressed in higher density, i.e. in greater number, on infectious HBV virion particles than on non-infectious, spherical and filamentous, HBV virion particles. (Hong et al., *Virology*, 318:134-141, 2004; Heerman et al., *J. Virol.*, 52(2):396-402, 1984; and Park et al., *Antiviral Res.*, 68:109-115, 2005). In certain embodiments, at least three, at least four, at least five, at least six, at least seven, at least eight, at least nine, at least ten, at least eleven, or at least twelve antigen binding domains of the binding units of a multimeric binding molecule as provided herein can specifically bind to a hepatitis B virus (HBV) antigen expressed on the surface of infectious viral particles, on the surface of HBV infected cells, or a combination thereof. While not wishing to be bound by theory, multimeric binding molecules possessing specificity for an HBV antigen that is more highly expressed in infectious HBV virions can be more effective, possess higher activity, be more potent or require fewer molecules to achieve the desired activity of enhancing viral clearance, e.g., through killing of infected cells, suppressing infectivity, e.g., through virus neutralization, and/or suppressing growth or maintenance of the HBV virus in an infected individual, e.g., an acutely, chronically, or latently infected individual, than a reference single binding unit, as discussed above.

Alternatively, the HBV antigen can be any one or more of the HBV proteins including envelope proteins (S, M and/or L), precore antigen (e.g., HBeAg), core antigen (e.g., HBcAg), and X-antigen (e.g., HBx). Further, a multimeric binding molecule as provided herein can possess binding units, each of which independently possess specificity for any one or more of these HBV antigens. Thus, a single multimeric binding molecule can, for example, possess specificity for one or more of the HBV antigens including envelope proteins (S, M and/or L), precore antigen, core antigen and X-antigen.

IgA Binding Molecules

IgA plays a critical role in mucosal immunity, and comprises about 15% of total immunoglobulin produced. IgA is a monomeric or dimeric molecule. A dimeric binding molecule as provided herein can possess binding characteristics or biological activity that can be distinguished from a binding molecule comprising five or six binding units, e.g., a hexameric or pentameric IgM antibody. For example, a dimeric binding molecule would be smaller, and could achieve better tissue penetration. IgA binding molecules can be manufactured by expression in vitro to include two IgA monomers and a J-chain. IgA molecules can then be administered to an individual, e.g., through intravenous infusion, and IgA molecules that migrate to mucous membranes or mucosal tissue can bind to and form a complex with a secretory component produced by epithelial cells, forming sIgA. Oligomeric sIgA is translocated across epithelial cells where ultimately sIgA is delivered to the mucosal surface. (Kaetzel et al., *Proc. Natl. Acad. Sci. USA* 88(19):8796-8800). Therefore, delivery of IgA to the blood stream can provide targeting of mucosal tissues.

An IgA binding unit includes two light and two heavy chains. IgA contains three heavy chain constant domains (Cα1, Cα2 and Cα3), and includes a C-terminal "tailpiece." Human IgA has two subtypes, IgA1 and IgA2. The human IgA1 constant region typically comprises the amino acid sequence SEQ ID NO: 55:

```
ASPTSPKVFPLSLCSTQPDGNVVIACLVQGFFPQEPLSVTWSESGQGVT

ARNFPPSQDASGDLYTTSSQLTLPATQCLAGKSVTCHVKHYTNPSQDVT

VPCPVPSTPPTPSPSTPPTPSPSCCHPRLSLHRPALEDLLLGSEANLTC

TLTGLRDASGVTFTWIPSSGKSAVQGPPERDLCGCYSVSSVLPGCAEPW

NHGKTFTCTAAYPESKTPLTAILSKSGNTFRPEVHLLPPPSEELALNEL

VTLTCLARGFSPKDVLVRWLQGSQELPREKYLTWASRQEPSQGTTTFAV

ISILRVAAEDWKKGDTFSCMVGHEALPLAFTQKTIDRLAGKPTHVNVSV

VMAEVDGTCY
```

The human Cα1 region ranges from about amino acid 6 to about amino acid 98 of SEQ ID NO: 55; the human Cα2 region ranges from about amino acid 125 to about amino acid 220 of SEQ ID NO: 55, the human Cα3 region ranges from about amino acid 228 to about amino acid 330 of SEQ ID NO: 55, and the tailpiece ranges from about amino acid 331 to about amino acid 352 of SEQ ID NO: 55. The human IgA2 constant region typically comprises the amino acid sequence SEQ ID NO: 56:

```
ASPTSPKVFPLSLDSTPQDGNVVVACLVQGFFPQEPLSVTWSESGQNVT

ARNFPPSQDASGDLYTTSSQLTLPATQCPDGKSVTCHVKHYTNPSQDVT

VPCPVPPPPPCCHPRLSLHRPALEDLLLGSEANLTCTLTGLRDASGATF

TWTPSSGKSAVQGPPERDLCGCYSVSSVLPGCAQPWNHGETFTCTAAHP

ELKTPLTANITKSGNTFRPEVHLLPPPSEELALNELVTLTCLARGFSPK

DVLVRWLQGSQELPREKYLTWASRQEPSQGTTTFAVTSILRVAAEDWKK

GDTFSCMVGHEALPLAFTQKTIDRMAGKPTHVNVSVVMAEVDGTCY
```

The human Cα1 region ranges from about amino acid 6 to about amino acid 98 of SEQ ID NO: 56; the human Cα2 region ranges from about amino acid 112 to about amino acid 207 of SEQ ID NO: 56, the human Cα3 region ranges from about amino acid 215 to about amino acid 317 of SEQ ID NO: 56, and the tailpiece ranges from about amino acid 318 to about amino acid 340 of SEQ ID NO: 56.

Two IgA binding units can form a complex with two additional polypeptide chains, the J-chain (SEQ ID NO: 54) and the secretory component (SEQ ID NO: 57) to form a secretory IgA (sIgA) antibody. While not wishing to be bound by theory, the assembly of IgA binding units into a dimeric sIgA binding molecule is thought to involve the Cα3 and tailpiece domains. Accordingly, a dimeric IgA binding molecule provided in this disclosure typically includes IgA constant regions that include at least the Cα3 and tailpiece domains. The amino acid sequence of the secretory component (SEQ ID NO: 57) is provided below:

KSPIFGPEEVNSVEGNSVSITCYYPPTSVNRHTRKYWCRQGARGGCITL

ISSEGYVSSKYAGRANLTNFPENGTFVVNIAQLSQDDSGRYKCGLGINS

RGLSFDVSLEVSQGPGLLNDTKVYTVDLGRTVTINCPFKTENAQKRKSL

YKQIGLYPVLVIDSSGYVNPNYTGRIRLDIQGTGQLLFSVVINQLRLSD

AGQYLCQAGDDSNSNKKNADLQVLKPEPELVYEDLRGSVTFHCALGPEV

ANVAKFLCRQSSGENCDVVVNTLGKRAPAFEGRILLNPQDKDGSFSVVI

TGLRKEDAGRYLCGAHSDGQLQEGSPIQAWQLFVNEESTIPRSPTVVKG

VAGGSVAVLCPYNRKESKSIKYWCLWEGAQNGRCPLLVDSEGWVKAQYE

GRLSLLEEPGNGTFTVILNQLTSRDAGFYWCLTNGDTLWRTTVEIKIIE

GEPNLKVPGNVTAVLGETLKVPCHFPCKFSSYEKYWCKWNNTGCQALPS

QDEGPSKAFVNCDENSRLVSLTLNLVTRADEGWYWCGVKQGHFYGETAA

VYVAVEERKAAGSRDVSLAKADAAPDEKVLDSGFREIENKAIQDPR

An IgA heavy chain constant region can additionally include a Cα2 domain or a fragment thereof, a Cα1 domain or a fragment thereof, and/or other IgA heavy chain domains. In certain aspects, a binding molecule as provided herein can include a complete IgA heavy (α) chain constant domain, e.g., SEQ ID NO: 55 or SEQ ID NO: 56, or a fragment thereof.

Dimeric HBV Binding Molecules

This disclosure provides a multimeric binding molecule, e.g., a multimeric binding molecule comprising two or more IgA molecules, where each IgA molecule can comprise one or two "binding units" as defined herein, that can specifically bind to an HBV antigen, e.g., HBsAg, e.g., the pre-S1 region of HBsAg. As explained above in the context of IgM multimeric binding molecules, an IgA multimeric binding molecule as provided herein can possess improved binding characteristics or biological activity as compared to a binding molecule composed of a reference single binding unit, e.g., a single binding unit IgG antibody. In other words, the IgA binding molecule provided herein can in some embodiments enhance viral clearance, and/or be more potent in, e.g., enhancing viral clearance, e.g., through killing of infected cells, suppressing infectivity, e.g., through virus neutralization, and/or suppressing growth or maintenance of the HBV virus in an infected individual, e.g., an acutely, chronically, or latently infected individual, as compared with a reference single binding unit comprising just two HBV-specific antigen binding domains. The term "improved binding characteristics" can be further clarified as follows. The IgA binding molecule provided herein, when administered to an individual in need thereof, can exhibit an activity that is empirically determined to be stronger, more potent, or require less binding molecule by mass or molar equivalents, to enhance viral clearance, reduce the infectivity of an infectious HBV virion, and/or reduce the growth of an infectious HBV virion in an infected individual, as compared with an single, i.e. non-multimeric, binding molecule comprising just one binding unit that possesses antigen binding domains identical in sequence to those of the IgA binding molecule provided herein.

The reference single binding unit referred to above can be an IgG binding unit. The reference IgG binding unit can be of any isotype, such as IgG1, IgG2, IgG3, or IgG4, etc. The reference binding unit is typically from the same animal. Thus if the multimeric binding molecule is human, the reference single binding unit would also be human, but not necessarily human. That is, the reference single binding unit can be a humanized antibody of the IgG type. Conversely, if the multimeric binding molecule is a rabbit binding molecule, the reference single binding unit would also be a rabbit binding unit. Further, if the multimeric binding molecule is comprised of one or more binding unit fragments, then the reference single binding unit would also be an equivalent single binding unit fragment. In other words, the reference single binding unit is otherwise identical in sequence and structure to the binding units contained in the multimeric binding molecule except that the reference single binding unit is an equivalent single binding unit.

In certain aspects, the disclosure provides a multimeric binding molecule comprising two bivalent binding units, where each binding unit includes two IgA heavy chain constant regions or fragments thereof. In certain aspects, the two IgA heavy chain constant regions are human heavy chain constant regions. The IgA binding units can be human, or humanized, binding units, or a combination thereof. Alternatively, the IgM binding units can be of mixed species in a single IgM binding molecule.

A multimeric, e.g., dimeric IgA binding molecule as provided herein can further comprise a J-chain, or functional fragment thereof, or variant thereof. In certain aspects, the J-chain is a modified J-chain comprising a heterologous moiety or one or more heterologous moieties, e.g., a heterologous polypeptide sequence, e.g., an extraneous binding domain introduced into the native sequence. In certain aspects the extraneous binding domain specifically binds to CD3, e.g., CD3ε. In certain aspects the mature modified J-chain comprises V15J (SEQ ID NO: 68) or J15V (SEQ ID NO: 71). A multimeric IgA binding molecule as provided herein can further comprise a secretory component, or fragment thereof, or variant thereof.

An IgA heavy chain constant region can include one or more of a Cα1 domain, a Cα2 domain, and/or a Cα3 domain, provided that the constant region can serve a desired function in the binding molecule, e.g., associate with second IgA constant region to form an antigen binding domain, or associate with another IgA binding unit to form a dimeric binding molecule. In certain aspects the two IgA heavy chain constant regions or fragments thereof within an individual binding unit each comprise a Cα3 domain or fragment thereof, a tailpiece (TP) or fragment thereof, or any combination of a Cα3 domain, a TP, or fragment thereof. In certain aspects the two IgA heavy chain constant regions or fragments thereof within an individual binding unit each further comprise a Cα2 domain or fragment thereof, a Cα1 domain or fragment thereof, or a Cα1 domain or fragment thereof and a Cα2 domain or fragment thereof.

In certain aspects each of the two IgA heavy chain constant regions in a given antigen binding domain is associated with an antigen binding domain, for example an Fv portion of an antibody, e.g., a VH and a VL of a human or murine antibody. In certain aspects, at least one antigen binding domain of a binding molecule as provided herein is a cross-reactive HBV antigen binding domain, e.g., an antigen binding domain that can specifically bind to two, three, four, or more HBV subtypes. In certain aspects at least one antigen binding domain binds to the pre-S1 or X antigen of the HBV virion.

In other embodiments, an IgA binding molecule as provided herein can comprise binding units wherein each binding unit can possess two antigen binding domains, each with a different and distinguishable specificity. Thus, a dimeric IgA binding molecule could possess as many as four different specificities.

In certain aspects at least one antigen binding domain binds to the S region, the pre-S2 region, and/or the pre-S1 region of the HBV virion envelope protein (HBsAg). In certain embodiments, at least one antigen binding domain specifically binds to the pre-S1 protein. In some aspects the multimeric binding molecule binds to an HBV antigen that comprises pre-S1, pre-S2 and S. In some embodiments the HBV antigen is pre-S1 and pre-S2, or pre-S1 and S, or pre-S2 and S. The binding unit that binds to the pre-S1 antigen can possess one or more different specificities for the pre-S1 antigen. That is, at least one binding unit of a multimeric binding molecule as provided herein is specific for pre-S1 protein of the HBV envelope protein and because each binding unit can possess as many as two antigen binding domains, each antigen binding domain can bind to different and distinguishable epitopes on the pre-S1 protein. In other embodiments, when the multimeric binding molecule comprises more than one binding unit, each binding unit can independent be specific for a different HBV antigen. Thus, in a multimeric binding molecule comprising at least two bivalent binding units, one binding unit can possess specificity for pre-S1 antigen; another binding unit can possess specificity for S antigen, etc. Alternatively, all of the binding units can possess identical specificity for pre-S1, for example. Thus, just as each binding unit can be comprised of different antigen binding domains, a multimeric binding molecule can possess one or more specificities for different HBV antigens. In an aspect of the disclosure, all binding units of the multimeric binding molecule possess specificity for pre-S1 antigen. In certain aspects at least one antigen binding domain binds to the HBV X antigen (HBxAg).

The HBV antigen for which a binding unit of a provided multimeric binding molecule possesses specificity can be expressed on the surface of an infectious HBV virion, on the surface of HBV-infected cells, or a combination thereof in higher density than the HBV antigen is expressed on non-infectious sub-viral particles. For instance, it is known that pre-S1 is expressed in higher density, i.e. in greater number, on infectious HBV virion particles than on non-infectious, spherical and filamentous, HBV virion particles. (Hong et al., *Virology*, 318:134-141, 2004; Park et al., *Antiviral Res.*, 68:109-115, 2005). In certain embodiments, at least two, at least three, or at least four antigen binding domains of a multimeric binding molecule provided herein specifically bind to a hepatitis B virus (HBV) antigen expressed on the surface of infectious viral particles, on the surface if HBV infected cells, or a combination thereof. When expressed on the surface of infected cells, the higher-density HBV antigen can be found in the context of MEW molecules expressed on the surface of infected cells. While not wishing to be bound by theory, multimeric binding molecules possessing specificity for an HBV antigen that is more highly expressed in infectious HBV virions can be more effective, possess higher activity, be more potent or require less molecules to achieve the desired activity of enhancing viral clearance, suppressing infectivity, and/or suppressing growth of the HBV virus in an infected individual, than a reference single binding unit, as discussed above.

Alternatively, the HBV antigen can be any one or more of the HBV proteins including HBsAg envelope proteins (S, M and/or L), precore antigen (e.g., HBeAg), core antigen (e.g., HBcAg) and X-antigen (e.g., HBx). Further, a multimeric binding molecule as provided herein can possess binding units that each independently possesses specificity for any one or more of these HBV antigens. Thus, a single multimeric binding molecule can, for example, possess specificity for one or more of the HBV antigens including envelope proteins (S, M and/or L), precore antigen, core antigen and X-antigen.

Modified J-Chains

In certain aspects HBV binding molecules provided herein can be bispecific, incorporating a modified J-chain. As provided herein and in PCT Publication No. WO 2015/153912, a modified J-chain can comprise a heterologous moiety, e.g., a heterologous polypeptide, e.g., an extraneous binding domain, which can include, for example, a polypeptide binding domain capable of specifically binding to a target. The binding domain can be, for example, an antibody or antigen-binding fragment thereof, an antibody-drug conjugate or antigen-binding fragment thereof, or an antibody-like molecule. A polypeptide binding domain can be introduced into a J-chain by appropriately selecting the location and type of addition (e.g. direct or indirect fusion, chemical tethering, etc.).

In certain aspects, the binding domain can be an antibody or an antigen-binding fragment of an antibody, including monospecific, bispecific, and multi-specific antibodies and antibody fragments. The antibody fragment can be, without limitation, a Fab fragment, a Fab' fragment, a F(ab')$_2$ fragment, an scFv, (scFv)$_2$ fragment, single-chain antibody molecules, minibodies, or multispecific antibodies formed from antibody fragments. In certain aspects, the antibody fragment is a scFv.

In other aspects, the binding domain can be an antibody-like molecule, for example, a human domain antibody (dAb), Dual-Affinity Re-Targeting (DART) molecule, a diabody, a di-diabody, dual-variable domain antibody, a Stacked Variable Domain antibody, a Small Modular Immuno Pharmaceutical (SMIP), a Surrobody, a strand-exchange engineered domain (SEED)-body, or TandAb.

The binding domain can be introduced into the native J-chain sequence at any location that allows the binding of the binding domain to its binding target without interfering with the binding of the recipient IgM or IgA molecule to its binding target or binding targets or the ability of the J-chain to effectively incorporate into an IgA dimer or an IgM pentamer. In certain aspects the binding domain can be inserted at or near the C-terminus, at or near the mature N-terminus (i.e., amino acid number 23 of SEQ ID NO: 54 following cleavage of the signal peptide) or at an internal location that, based on the three-dimensional structure of the J-chain is accessible. In certain aspects, the binding domain can be introduced into the native sequence J-chain without about 10 residues from the C-terminus or without about 10 amino acid residues from the mature N-terminus, of the human J-chain of SEQ ID NO: 54. In another aspect, the binding domain can be introduced into the native sequence human J-chain of SEQ ID NO: 54 in between cysteine residues 114 and 123 of SEQ ID NO: 54, or at an equivalent location of another native sequence J-chain. In a further aspect, the binding domain can be introduced into a native sequence J-chain, such as a J-chain of SEQ ID NO: 54, at or near a glycosylation site. In certain aspects, the binding domain can be introduced into the native sequence human J-chain of SEQ ID NO: 54 within about 10 amino acid residues from the C-terminus.

Introduction can be accomplished by direct or indirect fusion, i.e. by the combination of the J-chain and binding domain in one polypeptide chain by in-frame combination of their coding nucleotide sequences, with or without a peptide linker. The peptide linker (indirect fusion), if used, can be about 1 to 50, or about 1 to 40, or about 1 to 30, or about 1 to 20, or about 1 to 10, or about 1 to 5, or about 10 to 20 amino acids in length, and can be present at one or both ends of the binding domain to be introduced into the J-chain sequence. In certain aspects, the peptide linker is about 1 to 5, about 10 to 20, or about 10 to 15 amino acids long. In certain aspects the peptide linker is 15 amino acids long. In certain aspects the peptide linker is (GGGGS)$_3$ (SEQ ID NO: 72).

It is also possible to introduce more than one heterologous polypeptide, e.g., more than one binding domain, into a J-chain.

The modified J-chain can be produced by well-known techniques of recombinant DNA technology, by expressing a nucleic acid encoding the modified J-chain in a suitable prokaryotic or eukaryotic host organism.

The modified J-chain can also be co-expressed with the heavy and light chains of the recipient IgM or IgA binding molecules as described elsewhere herein. The recipient binding molecule, prior to the modified J-chain incorporation, can be monospecific, bispecific or multi-specific, e.g., a monospecific, bispecific, or multispecific IgA or IgM antibody. Bispecific and multi-specific IgM and IgA binding molecules, including antibodies, are described, for example, in U.S. Application Ser. Nos. 61/874,277 and 61/937,984, the entire contents of which are hereby expressly incorporated by reference.

In certain aspects, an anti-HBV IgM or IgA binding molecule as described herein can include a modified J-chain with binding specificity for an immune effector cell, such as a T-cell, NK-cell, a macrophage, or a neutrophil. In certain aspects the effector cell is a T-cell and the binding target is CD3 (discussed below). By activating and redirecting effector cells, e.g. effector T-cells (T-cell dependent killing or TDCC), to infected cells expressing HBV antigens, e.g., HBsAg, on their surface, a bispecific anti-HBV×anti-CD3 IgM or IgA binding molecule as provided herein can produce an enhanced immune response against the target, the response comprising, e.g., complement-mediated cytotoxicity, antibody dependent cellular cytotoxicity (ADCC), TDCC, and/or NK-cell mediated killing, thereby further increasing potency and efficacy. In certain aspects, a bispecific anti-HBV×anti-CD3 IgM or IgA binding molecule as provided herein comprising a modified J-chain can be used for the treatment of a disease or condition caused by, or exacerbated by infection with hepatitis B virus.

In the case of T-cells, cluster of differentiation 3 (CD3) is a multimeric protein complex, known historically as the T3 complex, and is composed of four distinct polypeptide chains (ε, γ, δ, ζ) that assemble and function as three pairs of dimers (εγ, εδ, ζζ). The CD3 complex serves as a T-cell co-receptor that associates non-covalently with the T-cell receptor (TCR). Components of this CD3 complex, especially CD3ε, can be targets for a modified J-chain of a bispecific IgM or IgA binding molecule provided herein.

In certain aspects, a bispecific anti-HBV×anti-CD3 IgM or IgA binding molecule binds to HBV-infected cells or HBV virus particles via the antibody binding domains, while the J-chain is modified to bind to CD3ε.

In certain aspects the anti-CD3ε binding domain of a modified J-chain provided herein is a scFv. The anti CD3ε scFv can be fused at or near the N-terminus of the J-chain, or at or near the C-terminus of the J-chain either directly or indirectly with a synthetic linker introduced in between the scFv and the J-chain sequences, e.g., a (GGGGS)$_3$ linker (SEQ ID NO: 72). In certain aspects the scFv comprises the VH and VL regions of visilizumab (Nuvion). In certain aspects the modified J-chain comprises a scFv comprising the VH of visilizumab, a (GGGGS)$_3$ linker, and the VL of visilizumab.

In certain aspects the modified J-chain comprises a scFv of visilizumab fused to the N-terminus of the human J-chain through a 15-amino acid (GGGGS)$_3$ linker, a modified J-chain referred to herein as V15J. V15J can further include a signal peptide to facilitate transport and assembly into an IgM or IgA binding molecules. The mature V15J protein is presented as SEQ ID NO: 68, the precursor version, comprising a 19-amino acid-immunoglobulin heavy chain signal peptide is presented as SEQ ID NO: 67. In certain aspects the modified J-chain comprises a scFv of visilizumab fused to the C-terminus of the human J-chain through a 15-amino acid (GGGGS)$_3$ linker, a modified J-chain referred to herein as J15V. J15V can further include a signal peptide to facilitate transport and assembly into an IgM or IgA binding molecules. The mature J15V protein is presented as SEQ ID NO: 71, the precursor version, comprising the 22-amino acid-human J-chain signal peptide is presented as SEQ ID NO: 70. In certain aspects, other signal peptides can be used. Selection and inclusion of suitable signal peptides to facilitate expression, secretion, and incorporation of a modified J-chain into an anti-HBV IgM or IgA binding molecule as provided herein is well within the capabilities of a person of ordinary skill in the art.

Engineered HBV Antigen Binding Domains

In certain aspects an HBV antigen binding domain as provided herein can include as many as six immunoglobulin complementarity determining regions HCDR1, HCDR2, HCDR3, LCDR1, LCDR2, and LCDR3, wherein at least one, at least two, at least three, at least four, at least five, or at least six CDRs are related to, or in some embodiments identical to, the corresponding CDRs of the HBV mAbs set forth in Table 2 below. In certain aspects an HBV antigen binding domain as provided herein can include as many as six immunoglobulin complementarity determining regions HCDR1, HCDR2, HCDR3, LCDR1, LCDR2, and LCDR3, wherein at least one, at least two, at least three, at least four, at least five, or at least six CDRs are related to, or in some embodiments identical to, the corresponding CDRs of the HBV mAbs KR127, disclosed in U.S. Pat. No. 7,115,723. The KR127 antibody and its derivatives are specific for an HBsAg pre-S1 epitope. In certain aspects an HBV antigen binding domain as provided herein can be a humanized version of KR127, e.g., KR127I, where the VH and VL regions comprise the amino acid sequences SEQ ID NOs 1 and 3, respectively, KR127III, where the VH and VL regions comprise the amino acid sequences SEQ ID NOs 1 and 3, respectively, both as disclosed in U.S. Pat. No. 7,115,723. In another aspect, an HBV antigen binding domain as provided herein can be a humanized, affinity matured version of KR127 as provided in U.S. Pat. No. 8,420,353 (VH and VL SEQ ID NOs: 5 and 6, respectively), in Hong et al., Virol., 318:131-141, 2004 (VH and VL SEQ ID NOs 4 and 3, respectively), or in Kim, J. H., et al. FEBS Letters 589:193-20, 2015 (VH and VL SEQ ID NOs 47 and 48, respectively.

Methods for genetically engineering cloned variable regions into immunoglobulin domains, and expressing and purifying such constructs are published and within the capability of one of skill in the art. (See, for instance, Wu et al., *MAbs,* 1:339-47, 2009, and Wu et al., *Nat. Biotechnol.,* 25:1290-7, 2007).

Table 2 provides the VH and VL amino acid sequences of exemplary, non-limiting HBV binding domains that can be used in a multimeric binding molecule as provided herein, as well as the identified epitopes to which binding domain binds. These sequences, or variants, fragments, or derivatives thereof, can be engineered into a standard pentameric or hexameric IgM or an IgA structure.

TABLE 2

VH and VL Amino Acid Sequences for Monoclonal Antibodies Specific for HBV

| Source | Target | VH SEQ ID NO | VH | VL SEQ ID NO | VL |
|---|---|---|---|---|---|
| U.S. Pat. No. 7,115,723 | Pre-S1 | 1 | QVQLVQSGAEVVKPGASVKVSCKASG YAFSSSWMNWVRQAPGQGLEWIGRIYP GDGDTNYAQKFQGKATLTADKSTSTA YMELSSLRSEDTAVYFCAREYDEAYW GQGTLVTVSS | 3 | DILMTQTPLSLSVTPGQPASISCKSSQSLLYS NGKTYLNWLLQKPGQSPKRLIYLVSKLDSG VPDRFSGSGSGTDFTLKISRVEAEDVGVYYC VQGTHPQTFGGGTKVEIKR |
| U.S. Pat. No. 7,115,723 | Pre-S1 | 2 | QVQLVQSGAEVVKPGASVKVSCKASG YTFTSSWMNWVRQAPGQGLEWMGRIY PGDGDTNYAQKFQGRVTMTADKSTST VYMELSSLRSEDTAVYYCAREYDEAY WGQGTLVTVSS | 3 | DILMTQTPLSLSVTPGQPASISCKSSQSLLYS NGKTYLNWLLQKPGQSPKRLIYLVSKLDSG VPDRFSGSGSGTDFTLKISRVEAEDVGVYYC VQGTHPQTFGGGTKVEIKR |
| Hong et al., Viral., 318:131-141,2004 | Pre-S1 | 4 | QVQLVQSGPELAKVGASVKVSCKASG YAFSSSWMNWVRQAPGQGLEWIGRIYP GDGDTNYAQKFQGKATLTADKSTSTA YMELSSLRSEDTAVYFCAREYDEAYW GQGTLVTVSS | 3 | DILMTQTPLSLSVTPGQPASISCKSSQSLLYS NGKTYLNWLLQKPGQSPKRLIYLVSKLDSG VPDRFSGSGSGTDFTLKISRVEAEDVGVYYC VQGTHPQTFGGGTKVEIKR |
| U.S. Pat. No. 8,420,353 | Pre-S1 | 5 | QVQLVQSGAEVKAPGASVKVSCKASG YTFTSAWMNWVRQAPGQGLEWMGRI YPSGGSTSYAQKFQGRVTMTADKSTST VYMELSSLRSEDTAVYYCAREYRVAR WGQGTLVTVSA | 6 | DIVMTQTPLSLSVTPGQPASISCKSSQSLLYS NGKTYLNWLLQKPGQPPQRLIYLVSNRDSG VPDRFSGSGSGTDFTLKISRVEAEDVGVYYC VQGTHPQTFGGGTKVEIK |
| WO 2011/045079A1 | Pre-S1 | 7 | EVQLVESGGDLVKPGGSLRLSCAASGL TFSNAWMNWVRQAPGKGLEWVGRIKS KSDGGTTDYAAPVEGRFSISRDDSKDTL YLQMNSLKTEDTAVYYCASRLVAEGG FDSWGQGTLVTVSS | 8 | DIVMTQSPDSLAVSLGERATINCKSSQSVLY SSNNRNYLAWYQQKPGQPPKLLIYWASTR DSGVPDRFSGSGSGTDFTLTISSLQAEDVAV YYCQQYYNTPYSFGQGTKLEIK |
| WO 2011/045079A1 | Pre-S1 | 7 | EVQLVESGGDLVKPGGSLRLSCAASGL TFSNAWMNWVRQAPGKGLEWVGRIKS KSDGGTTDYAAPVEGRFSISRDDSKDTL YLQMNSLKTEDTAVYYCASRLVAEGG FDSWGQGTLVTVSS | 9 | DIVMTQSPDSLAVSLGERATINCKSSQSVLY SSNNKNYLAWYQQKPGQPPKLLIYWASTRE SGVPDRFSGSGSGTDFTLTISSLQAEDVAVY YCQQYYSTPYSFGQGTKLEIK |
| U.S. Reissue No. RE39586 | HBsAg | 10 | QVQLVESGGGVVRPGRSLRLSCAASGF AFSDYSINWVRQAPGKGLEWVAIISYD GRITYYRDSVKGRFTISRDDSKNTLYLQ MNSLRITEDTAVYYCARQYYDFWSGSS VGRNYDGMDVWGLGTTVTVSS | 11 | DIVMTQSPLSLSVTPGEPASISCRSSQSLLHR SGNNYLDWYLQKPGHSPQLLIYVGSNRASG VPDRFSGSGSGTEYTLKISRVEAEDVGVYY CMQALQTPRITFGQGTKLEIK |

TABLE 2-continued

VH and VL Amino Acid Sequences for Monoclonal Antibodies Specific for HBV

| Source | Target | VH SEQ ID NO | VH | VL SEQ ID NO | VL |
|---|---|---|---|---|---|
| Walsh et al., Viral., 411:132-141 (2011) | HBeAg | 12 | AWVDQTPRTATKETGESLTINCVLRDT SCAFSSTGWYRTKLGSTNEQSISTGGRY VETVNKTSKSISLRISDLRVEDSGTYKC QVYFTPVWDGSCFGILGRTKKGAGTAL TVK | | |
| Walsh et al., Viral., 411:132-141 (2011) | HBeAg | 13 | AWVDQTPRTATKETGESLTINCVLRDT SCAFSGTGWYRTKLGSTNEQSISIGGRY VETVSKGSKSISLRISDLRVEDSGTYKC QVYFTPVWDGSCFGILGRTKKGAGTAL TVK | | |
| WO2014048910A1 | HBsAg | 14 | EVQLVESGGGLVQPGGSLRVSCEVSGF TFSNNMMEWVRQAPGKGPVWVSRIST DGMSTSYAEFVKGRFTISRDNARNTLY LQMNSLRDEDTAVYYCVRGSTYYFGS GSLNFWGQGTTVTVSS | 15 | QSALTQPRSVSGSPGQSVTISCTGTNSDIGN YDYVSWYQQHPGKAPRLIIYDVSERPSGVP NRFSGSKSGNTASLTISGLQAEDESDYFCSS YAGTFYVVFGGGTKLTVL |
| WO2014010890A1 | HBsAg | 16 | QVKLLESGGGLVKPGGSLRLSCSASGFS LTKYKMTWVRQAPGKGLEWVSSISTS RDIDYADSVKGRFTISRDNAKNSLFLQ MSSLRVDDTAVYYCTRDGWLMGWDV RSNYYINALDVWGQGTTVTVSS | 21 | ELVMTQSPSSLSASVGDRVTITCRASQGIYN SIAWYQQKPGKAPKLLLYSTSTLLSGVPSRF SGSGSGTDYTLTITNLQPEDFATYYCQQYFV TPETFGQGTKVEIKR |
| WO2014010890A1 | HBsAg | 17 | EVQLVESGGGLVKPGGSLRLSCSASGFS LTKYKMTWVRQAPGKGLEWVSSISSTS RDIDYADSVKGRFTISRDNAKNSLFLQ MSSLRVDDTAVYYCTRDGWLMGWDV RSNYYINALDVWGQGTTVTVSS | 22 | DIVVTQSPSSLSASVGDRVTITCRASQGIYNS IAWYQQKPGKLLLYSTSTLLSGVPSRFS GSGSGTDYTLTITNLQPEDFATYYCQQYFVT PETFGQGTKLEIKR |
| WO2014010890A1 | HBsAg | 18 | QVQLVQSGGEVKKPGALMKVSCKASG YIFTSYGISWVRQAPQGLEWIGWINTY SGHTNYARKFRGRVTMTWDTSTSTAY MELSSLRSDDTAVYYCARVPTWGIDY WGQGTLVTVSS | 23 | QAGLTQPPSVSVAPGKTARITCGGDNIGRKS VHWYQQKTGQAPVLVVYEDNKRPSGIPERF SGSNSGNTATLTISGTQAMDEADYYCQAW DSSTVVFGGGTKLTVLG |
| WO2014010890A1 | HBsAg | 19 | QVQLVQSGGEVKKPGALMKVSCKASG YIFTSYGISWVRQAPGQGLEWINTY SGHTNYARKFRGRVTMTWDTSTSTAY MELSSLRSDDTAVYYCARVPTWGIDY WGQGTLVTVSS | 24 | EIVLTQSPPSLSASVGDRVTITCQASQDINNN VNWFQQEPGKAPRLLIYDASNLQTGVPSRF SGSGSGTEFTLTISSLQPEDFATYYCQQTSV YPLTFGGGTKVDIKR |
| WO2014010890A1 | HBsAg | 20 | QVQLVQSGGEVKKPGALMKVSCKASG YIFTSYGISWVRQAPGQGLEWIGWINTY SGHTNYARKFRGRVTMTWDTSTSTAY MELSSLRSDDTAVYYCARVPTWGIDY WGQGTLVTVSS | 25 | DIVMTQTPLSLPVTPGEPASISCRSSQSLLHS NGYNYLDWYLQKPGQSPQLLIYLGSKRASG VPDRFSGSGSGTDFTLQISRVEAEDVGVYYC MQSTQFPPYIFGQGTKLEIKR |

TABLE 2-continued

VH and VL Amino Acid Sequences for Monoclonal Antibodies Specific for HBV

| Source | Target | VH SEQ ID NO | VH | VL SEQ ID NO | VL |
|---|---|---|---|---|---|
| U.S. Pat. No. 8,840,895 | HBsAg | 26 | QVQLVQSGGEVKKPGALMKVSCKASG YIFTSYGISWVRQAPGQGLEWIGWINTY SGHTNYARKFRGRVTMTWDTSTSTAY MELSSLRSDDTAVYYCARVPTWGIDY WGQGTLVTVSS | 27 | QAGLTQPPSVSVAPGKTARITCGGDNIGRKS VHWYQQKTGQAPVLVVYEDNKRPSGIPERF SGSNSGNTATLTISGTQAMDEADYYCQAW DSSTVVFGGGTKLTVLG |
| U.S. Pat. No. 8,840,895 | HBsAg | 26 | QVQLVQSGGEVKKPGALMKVSCKASG YIFTSYGISWVRQAPGQGLEWIGWINTY SGHTNYARKFRGRVTMTWDTSTSTAY MELSSLRSDDTAVYYCARVPTWGIDY WGQGTLVTVSS | 28 | EIVLTQSPPSLSASVGDRVTITCQASQDINNN VNWFQQEPGKAPRLLIYDASNLQTGVPSRF SGSGSGTEFFLTISSLQPEDFATYYCQQTSV YPLTFGGGTKVDIKR |
| U.S. Pat. No. 8,840,895 | HBsAg | 26 | QVQLVQSGGEVKKPGALMKVSCKASG YIFTSYGISWVRQAPGQGLEWIGWINTY SGHTNYARKFRGRVTMTWDTSTSTAY MELSSLRSDDTAVYYCARVPTWGIDY WGQGTLVTVSS | 29 | DIVMTQTPLSLPVTPGEPASISCRSSQSLLHS NGYNYLDWYLQKPGQSPQLLIYLGSKRASG VPDRFSGSGSGTDFTLQISRVEAEDVGVYYC MQSTQPPYTFPGQGTKLEIKR |
| U.S. Pat. No. 8,580,256 | HBsAg | 30 | QVQLVESGGGVVQPGGSLRLSCAPSGF VFRSYGMHWVRQTPGKGLEWVSLIWH DGSNRFYADSVKGRFTISRDNSKNTLYL QMNSLRAEDTAMYFCARERLIAAPAAF DLWGQGTLVTVLG | 31 | SYVLTQPPSVSVAPGKTARISCGGNNIGTKN VHWYQQKPGQAPVLVVYADSDRPSGIPERF SGSNSGNTATLTISRVEVGDEADYYCQVWD SVSYHVVFGGGTTLTVLG |
| U.S. Pat. No. 8,580,256 | HBsAg | 32 | QVQLVESGGGVRPGRSLRLSCAASGF AFSDYISINWVRQAPGKGLEWVAIISYD GRITYRDSVKGRFTISRDDSKNTLYLQ MNSLRTEDTAVYYCARQYYDFWSGSS VGRNYDGMDVWGLGTTVTVSS | 33 | DIVMTQSPLSLSVTPGEPASISCRSSQSLLHR SGNNYLDWYLQKPGHSPQLLIYVGSNRASG VPDRFSGSGSGTEYTLKISRVEAEDVGVYY CMQALQTPRTFGQGTKLEIK |
| U.S. Pat. No. 7,435,414 | HBsAg | 34 | QVQLKQSGPGLVKPSQTLSLITCTVSGFS LSTYGVQWVRQPPGKGLEWLGVIWSG GNTDYNAAFISRVTISKDTSKNQVSLKL SSVTAADTAVYYCARARYFDWGAGT TVTVSS | 35 | QAVVTQEPSLITVSPGGTVTLTCRSSTGAITT NNFANWFQQKPGQAFRGLIGDTNNRVPGV PARFSGSLLGNKAALTITGAQPEDEAEYYC ALWYNNWVFGGGTKLTVLG |
| U.S. Pat. No. 7,435,414 | HBsAg | 34 | QVQLKQSGPGLVKPSQTLSLITCTVSGFS LSTYGVQWVRQPPGKGLEWLGVIWSG GNTDYNAAFISRVTISKDTSKNQVSLKL SSVTAADTAVYYCARARYFDWGAGT TVTVSS | 36 | QAVVTQEPSLITVSPGGTVTLTCRSSTGAITT NNFANWFQQKPGQAFRGLIGDTNNRVPGV PARFSGSLIGDKAALTITGAQPEDEAEYYCA LWYNNVFGGGTKLTVLG |
| U.S. Reissue Pat. No. RE40831 | HBsAg | 37 | QVQLVESGGGVVQPGGSLRLSCAPSGF VFRSYGMHWVRQTPGKGLEWVSLIWH DGSNRFYADSVKGRFTISRDNSKNTLYL QMNSLRAEDTAMYFCARERLIAAPAAF DLWGQGTLVTVSS | 38 | SYVLTQPPSVSVAPGKTARISCGGNNIGTKN VHWYQQKPGQAPVLVVYADSDRPSGIPERF SGSNSGNTATLTISRVEVGDEADYYCQVWD SVSYHVVFGGGTTLTVLG |

TABLE 2-continued

VH and VL Amino Acid Sequences for Monoclonal Antibodies Specific for HBV

| Source | Target | VH SEQ ID NO | VH | VL SEQ ID NO | VL |
|---|---|---|---|---|---|
| U.S. Pat. No. 5,565,354 | HBsAg | 39 | MEFGLSWVFLVALLRGVQCQVQLVES GGGVVQPGRSLRLSCAASGFTFSRYGM HWVRQAPGKGLEWVAVISYDGSNKW YADSVKGRFTISRDNSKNTLFLQMHSL RAADTGVYYCAKDQLYFGSQSPGHYW VQGTLVTVSS | 40 | QSQLTQPPSVSVAPGQTARITCGGDNIGSKS VNWFQQKPGQAPVLVVYDDNERPSGISERF SGSNSGNTATLTISRVEAGDEADYCQVWD SSSDHVVFGGGTKLITVL |
| U.S. Pat. No. 5,565,354 | HBsAg | 41 | MEFGLSWVFLVAILEGVQCEVQLVESG GGLVQPGGSLRLSCAASGFTFSRYDMY WVRQATCKGLEWVSAIGPTGDTYYAD SVKGRFTISRENAKNSLYLTMNGLRAG DTAVYYCARDLELWGQGTLVTVSS | 42 | MDTRVPAQLLGLLMLWVPGSSGDVVTQS PLSLPVTLGQPASISCRSSLSLVDSDGNTYLN WFLQRPGQSPPRLIYQLSRDSGVPDRFSGS GSGTDFTLKISRVEAEDVGVYYCMQGTHW PITFGQGTRLEIKR |
| U.S. Pat. No. 5,565,354 | HBsAg | 43 | MKHLWFLLLVAVPRWVSQVQLQES GPGLVKAAETLSLTCTVSRGSFSDYFW NWFRQPAGKRLEWLGRVYTSGSVDYN PSLKSRVTVSVDTSKKQFSLRLSSVTVA DTAVYYCARGLSGFDYWGQGALVTVS P | 44 | MRPVAQLLGLLLLWFPGSRCDIQMTQSPSS VSASVGDRVTVTCRASQGISSWLAWYQQK PGKAPKLIHAAASSLQSGVPSRFIGSGSGTDF TLTITSLQAEDFATYYCQQADSLPFTFGGGT KVDFKR |
| U.S. Pat. No. 5,565,354 | HBsAg | 45 | MGSTAILGLLLAVLQGVCAEVQLVQSG AEVKKPGESLRISCKGSGYSFTSYWISW VRQMPGKGLEWMGRLDPSASSAIFSPS LQGHVTISVDKSMRTAYVQWRSLKAS DTAMYCARHVREKSMVQGVIIKDAF DIWGQGTMVTVSS | 46 | QSQLTQPASVSVSPGQTASITCSGDRLGDEF ASWYQQKPGQSPILVIFEDNKRPSGIPERFSG SNSGNTATLTISGTQAMDEADYCLAWASS LWVFGGGTKLTVL |
| Kim, J.H., et al. FEBS Letters 589:193-200 (2015) | Pre-S1 | 47 | QVQLQQSGAEVKKPGASVKVSCKASG YTFTSSWMNWVRQAPGQGLEWMGRIY PGDGDTSYAQKFQGRVTMTADKSTSTV YMELSSLRSEDTAVYYCAREYAEAYW GQGTLVTVSS | 48 | DIVMTQTPLSLSVTPGQPASISCKSSQSLLYS NGKTYLNWLLQKPGQPPQRLIYLVSNRDSG VPDRFSGSGSGTDFTLKISRVEAEDVGVYYC VQGTHPQTFGGGTKVEIKR |
| zu Putlitz, J., et al. Gene 221(1), 143-149 (1998) | HBxAg | 49 | EVKLHESGAGLVKPGASVNLSCTASGF NIKDTYMHWVKQRPDQGLEWIGRIDPA NGNTKSDPKFQGKATITADTSSNTAYL QLSSLITSEDTAVYYCASYSWGQGTTVT VSS | 50 | DIELTQSPVSLGQRATISCKASQSVDYDGDS YMNWYQQKPGQPPKLLIYAASNLESGIPAR FSGSGSGTDFTLNIHPVEEEDAATYCQQSN EDPLITFGGGTKLELK |

TABLE 2-continued

VH and VL Amino Acid Sequences for Monoclonal Antibodies Specific for HBV

| Source | Target | VH SEQ ID NO | VH | VL SEQ ID NO | VL |
|---|---|---|---|---|---|
| Park,O.Y., et al. Hybridoma 19(1), 73-80 (2000) | HBxAg | 51 | QVQLQQPGAELVKPGASVKLSCKASGY TFTSYWIHWVKQRPGQGLEWIGEIDPS DSHANYNQKFKGKATLTVDKSSSTVY MQLSSLTSEDSAVYFCTNGYWGQGTTL TVSSA | 52 | DVVMTQTPLTLSVTIGQPASISCKSSQSLLDS DGETYLNWLLQRPGQSPKRLIYMVSKLDSG VPDRFTGSGSGTDFTLKISRVEAEDLGVYYC WQGTHPFTFGSGTKLEIKR |
| Cerino et al. (2015) PLOS one 10(4):e0125704. doi: 10.1371 | HBsAg | 73 | EVQVLESGGGLVQPGGSLRLSCAASGF RFSSYAMSWVRQAPGKGLEWVSGISGT GENTYYADSVKGRFTISRDNSKNTLYV QMNSLRAEDTAVYYCAKDAILGSGHP WYFHVWGRGTLVTVSS | 74 | SYVLTQPPSVSVAPGQTARMTCGGNNIGSE SVHWFQQKPGQAPVLVVYDDSDRPSGIPER FSGSNSGNTATLTISRVEAGDEADYYCQVW DSSSDHAVFGGGTQLTVL |
| Pizarro, et al., FEBS Letters 509:463-468 (2001) | Pre-S1 or ay serotype | 75 | EVQLEESGGGLVKPGGSLKLSCAASGF TFSSYAMSWVRQSPEKRLEWVAEVSSD GSYAYYPDTLTGRFTISRDNAKNTLYLE MTSLRSEDTAMYCASFNWDVAYWG QGTLVTVSAA | 76 | ELVMTQSPSSLAVSVGEKVTMSCRSSQSLL NTRTRKSYLAWFQQKPGQSPKMLIYWAST RESGVPDRFTGSGSGTDFTLTISSVQAEDLA VYYCKQSYSLYTFGGGTKLEIKR |

In certain aspects the HBV antigen binding domain of a dimeric, hexameric, or pentameric binding molecule as provided herein comprises an antibody heavy chain variable region (VH) and an antibody light chain variable region (VL), wherein the VH region, the VL region, or both the VH and VL regions are related to the corresponding VH and VL of HBV monoclonal antibodies disclosed in the references set forth in Table 2, above. In certain aspects, the binding molecules provided herein exhibit greater potency than an IgG antibody comprising the VH and VL of antibodies listed in Table 2. The increased avidity of IgA or IgM forms of anti-HBV can result in a more potent therapeutic antibody that can bind those infected cells with very low density of HBV surface proteins, allowing more efficient clearance of HBV from infected patients. In certain aspects the VH can comprise an amino acid sequence at least 60%, at least 65%, at least 70%, at least 75%, at least 80%, at least 85%, at least 90%, at least 95% or 100% identical to any one or more of SEQ ID NO: 1, SEQ ID NO: 2, SEQ ID NO: 4, SEQ ID NO: 5, SEQ ID NO: 7, SEQ ID NO: 7, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 26, SEQ ID NO: 26, SEQ ID NO: 26, SEQ ID NO: 30, SEQ ID NO: 32, SEQ ID NO: 34, SEQ ID NO: 34, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 62, SEQ ID NO: 73, or SEQ ID NO: 75. In certain aspects the VL can comprise an amino acid sequence at least at least 60%, at least 65%, at least 70%, at least 75%, at least 80%, at least 85%, at least 90%, at least 95% or 100% identical to any one or more of SEQ ID NO: 3, SEQ ID NO: 6, SEQ ID NO: 8, SEQ ID NO: 9, SEQ ID NO: 11, SEQ ID NO: 15, SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 74, or SEQ ID NO: 76. In certain aspects the VH/VL sequences comprise any one or more of the following pairs of sequences, respectively, SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76.

While a variety of different dimeric, hexameric, and pentameric binding molecules can be contemplated by a person of ordinary skill in the art based on this disclosure, and as such are included in this disclosure, in certain aspects, a binding molecule as described above is provided in which each binding unit comprises two IgM heavy chains each comprising a VH situated amino terminal to the IgM constant region or fragment thereof, and two immunoglobulin light chains each comprising a VL situated amino terminal to an immunoglobulin light chain constant region. In certain aspects, a binding molecule as described above is provided in which each binding unit comprises two IgA heavy chains each comprising a VH situated amino terminal to the IgA constant region or fragment thereof, and two immunoglobulin light chains each comprising a VL situated amino terminal to an immunoglobulin light chain constant region.

Moreover in certain aspects, at least one binding unit of the binding molecule, or two, three, four, five, or six binding units of the binding molecule, comprises or comprise two of the HBV antigen binding domains as described above. In certain aspects the two HBV antigen binding domains in the one binding unit of the binding molecule, or two, three, four, five, or six binding units of the binding molecule, can be different from each other, or they can be identical.

In certain aspects, the two IgA heavy chains within the one binding unit of the binding molecule, or two binding units of the binding molecule, are identical. In certain aspects, the two IgM heavy chains within the one binding unit of the binding molecule, or two, three, four, five, or six binding units of the binding molecule, are identical.

In certain aspects, the two light chains within the one binding unit of the binding molecule, or two, three, four, five, or six binding units of the binding molecule, are identical. In certain aspects, two identical light chains within at least one binding unit, or within at least two, at least three, at least four, at least five, or at least six binding units of the binding molecule are kappa light chains, e.g., human kappa light chains, or lambda light chains, e.g., human lambda light chains.

In certain aspects at least one, two, three, four, five, or six binding units of a dimeric, pentameric, or hexameric binding molecule provided by this disclosure comprises or each comprise two identical IgA or IgM heavy chains, and two identical light chains. According to this aspect, the HBV antigen binding domains in the one binding unit of the binding molecule, or two, three, four, five, or six binding units of the binding molecule, can be identical. Further according to this aspect, a dimeric, pentameric, or hexameric binding molecule as provided herein can comprise at least one, two, three, four, five, six, seven, eight, nine, ten, eleven, or twelve copies of an HBV antigen binding domain as described above. In certain aspects at least two, at least three, at least four, at least five, or at least six of the binding units can be identical and, in certain aspects the binding units can comprise identical antigen binding domains, e.g., at least two, at least three, at least four, at least five, at least six, at least seven, at least eight, at least nine, at least ten, at least eleven, or at least twelve HBV antigen binding domains can be identical.

In certain aspects, a dimeric, hexameric, or pentameric binding molecule includes at least one HBV antigen binding domain comprising a VH and a VL, where the VH region, the VL region, or both the VH and the VL regions are related to corresponding VH and VL regions comprising the amino acid sequences SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively. In certain aspects, a dimeric, hexameric, or pentameric binding molecule includes at least one HBV antigen binding domain comprising a VH, where the VH region is related to corresponding VH regions comprising the amino acid sequence SEQ ID NO: 12 or SEQ ID NO: 13.

In certain aspects, a dimeric, hexameric, or pentameric binding molecule includes at least one HBV antigen binding domain comprising a VH comprising the HCDR1, HCDR2, and HCDR3 regions, or HCDR1, HCDR2, and HCDR3 regions containing one or two single amino acid substitutions, and comprising the LCDR1, LCDR2, and LCDR3 regions, or LCDR1, LCDR2, and LCDR3 containing one or two single amino acid substitutions, of the VH and VL amino acid sequences SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively. In certain aspects, a dimeric, hexameric, or pentameric binding molecule includes at least one HBV antigen binding domain comprising a VH comprising the HCDR1, HCDR2, and HCDR3 regions, or HCDR1, HCDR2, and HCDR3 regions containing one or two single amino acid substitutions, of the VH amino acid sequence SEQ ID NO: 12 or SEQ ID NO: 13.

In certain aspects, a dimeric, hexameric, or pentameric binding molecule includes at least one HBV antigen binding domain comprising a VH and a VL, where the VH region, the VL region, or both the VH and the VL regions comprise amino acid sequences at least 60%, at least 65%, at least 70%, at least 75%, at least 80%, at least 85%, at least 90%, at least 95% or 100% identical to SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively. In certain aspects, a dimeric, hexameric, or pentameric binding molecule includes at least one HBV antigen binding domain comprising a VH, where the VH region comprises an amino acid sequence at least 60%, at least 65%, at least 70%, at least 75%, at least 80%, at least 85%, at least 90%, at least 95% or 100% identical to SEQ ID NO: 12 or SEQ ID NO: 13.

In certain aspects the VH and VL can be derived from the HBV pre-S1 mAb described in U.S. Pat. No. 7,115,723. For example, the HBV antigen binding domain can comprise a VH amino acid sequence at least 60%, at least 65%, at least 70%, at least 75%, at least 80%, at least 85%, at least 90%, at least 95% or 100% identical to SEQ ID NO: 1 or SEQ ID NO: 2, and a VL amino acid sequence at least 60%, at least 65%, at least 70%, at least 75%, at least 80%, at least 85%, at least 90%, at least 95% or 100% identical to SEQ ID NO: 3.

In certain aspects the VH and VL can be derived from the HBV pre-S1 mAb described in Hong et al., Viral., 318:131-141, 2004. For example, the HBV antigen binding domain can comprise a VH amino acid sequence at least 60%, at least 65%, at least 70%, at least 75%, at least 80%, at least 85%, at least 90%, at least 95% or 100% identical to SEQ ID NO: 4 and a VL amino acid sequence at least 60%, at least 65%, at least 70%, at least 75%, at least 80%, at least 85%, at least 90%, at least 95% or 100% identical to SEQ ID NO: 3.

In certain aspects the VH and VL can be derived from the HBV mAb described in U.S. Pat. No. 8,420,353. For example, the HBV antigen binding domain can comprise a VH amino acid sequence at least 60%, at least 65%, at least 70%, at least 75%, at least 80%, at least 85%, at least 90%, at least 95% or 100% identical to SEQ ID NO: 5 and a VL amino acid sequence at least 60%, at least 65%, at least 70%, at least 75%, at least 80%, at least 85%, at least 90%, at least 95% or 100% identical to SEQ ID NO: 6.

In certain aspects the HBV antigen binding domain can comprise VH and VL amino acid sequences comprising SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively. In certain aspects the HBV antigen binding domain can comprise a VH amino acid sequence comprising SEQ ID NO: 12 or SEQ ID NO: 13.

In certain aspects a hexameric or pentameric antibody designated herein as HBV24M is provided comprising an IgM heavy chain comprising the amino acid sequence SEQ ID NO: 58 and a kappa light chain comprising the amino acid sequence SEQ ID NO: 59. SEQ ID NOs 58 and 59 are provided here:

>HBV24 IgM Heavy chain
(SEQ ID NO: 58)
QVQLVQSGAEVKAPGASVKVSCKASGYTFTSAWMNWVRQAPGQGLEWMG

RIYPSGGSTSYAQKFQGRVTMTADKSTSTVYMELSSLRSEDTAVYYCAR

EYRVARWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSL

SPGK

>HBV24 Kappa Light chain
(SEQ ID NO: 59)
DIVMTQTPLSLSVTPGQPASISCKSSQSLLYSNGKTYLNWLLQKPGQPP

QRLIYLVSNRDSGVPDRFSGSGSGTDFTLKISRVEAEDVGVYYCVQGTH

FPQTFGGGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

In certain aspects, a humanized heavy chain variable region (VH) comprising the amino acid sequence SEQ ID NO: 62 is provided.

>HBV24M2 IgM Heavy chain
(SEQ ID NO: 62)
QVQLVQSGAEVKAPGASVKVSCKASGYTFTSAWMNWVRQAPG
QGLEWMGRIYPSGGSTSYAQKFQGRVTMTADKSTSTVYMELSSL
RSEDTAVYYCAREYDEAYWGQGTLVTVSS In certain aspects a hexameric or pentameric antibody designated herein as HBV24M2 is provided comprising an IgM heavy chain comprising the amino acid sequence SEQ ID NO: 63 and a kappa light chain comprising the amino acid sequence SEQ ID NO: 59. SEQ ID NO: 63 and 59 are provided here:

>HBV24M2 IgM Heavy chain
(SEQ ID NO: 63)
QVQLVQSGAEVKAPGASVKVSCKASGYTFTSAWMNWVRQAPGQGLEWMG

RIYPSGGSTSYAQKFQGRVTMTADKSTSTVYMELSSLRSEDTAVYYCAR

EYDEAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSL

SPGK

>HBV24 Kappa Light chain
(SEQ ID NO: 59)
DIVMTQTPLSLSVTPGQPASISCKSSQSLLYSNGKTYLNWLLQKPGQPP

QRLIYLVSNRDSGVPDRFSGSGSGTDFTLKISRVEAEDVGVYYCVQGTH

FPQTFGGGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

In certain aspects, a dimeric, pentameric, or hexameric HBV binding molecule as provided herein can possess advantageous structural and/or functional properties, or "improved binding characteristics," as compared to other binding molecules, such as a reference single binding unit comprising the same antigen binding domains. For example, the dimeric, pentameric, or hexameric HBV binding molecule can possess improved activity or potency in a biological assay, either in vitro or in vivo, relative to a corresponding reference single binding unit, e.g., an IgG1 binding molecule comprising the same VH and VL region sequences as are present in the multimeric binding molecule, as described above. Biological assays include, but are not limited to virus neutralization assays, assays, cell attachment assays, viral egress assays, immunohistochemical assays, direct cytotoxicity assays, complement-mediated cytotoxicity (CDC) assays, T-cell mediated killing (TDCC) assays, NK-cell mediated killing assays, etc. In certain aspects a dimeric, pentameric, or hexameric binding molecule, e.g., an IgM antibody as provided herein can direct HBV neutralization, or killing of an HBV infected cell, at higher potency than an equivalent amount of a monospecific, single binding unit IgG1 antibody or fragment thereof that specifically binds to the same HBV epitope as the HBV antigen binding domain.

By "potency" or "improved binding characteristics" is meant the least amount of a given binding molecule necessary to achieve a given biological result, e.g., neutralization of 20%, 50%, or 90% of a virus inoculum in a given assay ($EC_{20}$, $EC_{50}$, or $EC_{90}$). Potency can be expressed as a curve in which, for example, % virus neutralization, % killing of infected cells, or other measurable parameter is on the Y axis, and binding molecule concentration (in, e.g., µg/ml or nM) is on the X axis.

In certain aspects, TDCC can be measured in vitro through T-cell activation assays, e.g., by co-culturing HBsAg-expressing cells and engineered CD3-expressing T-cells in the presence of a bispecific anti-HBsAg×anti-CD3 IgM binding molecule as provided herein, and measuring T-cell activation through cytokine release, target cell lysis, or other detection method. In certain aspects TDCC can be measured through T-cell directed target cell killing.

In certain aspects the HBsAg-expressing cell can be an immortalized cell line, e.g., a hepatocellular carcinoma (HCC) cell line, e.g., PLC/PRF/5 cells, or a cell line, e.g., HEK293, CHO, HepG2, or HepaRG cells, transfected with and expressing an HBV antigen, e.g., HBsAg or HBsAg-L, or HBV-infected cells, e.g., HBV-infected HepaRG cells, or cells producing HBV, e.g., HepG2.2.15 cells. Similar cell lines are known and are easily obtained by a person of ordinary skill in the art. In certain aspects the HBV antigen-expressing cell line can be derived from a patient suffering from HBV infection, HCC, or a related cancer.

In certain aspects, the totality of killing of HBV antigen-expressing cells, e.g., by CDC, TDCC, ADCC, and other modes of killing, e.g., apoptosis, can be tested in vitro in an assay using isolated T-cells and/or complement or whole blood that includes both T-cells and complement.

In certain aspects, e.g., where the binding molecule is a pentameric binding molecule comprising five identical binding units each comprising two identical anti-HBsAg binding domains as provided herein, tested in a CDC assay using, e.g., the HBsAg-expressing PLC/PRF/5 cell line or HepG2.2.15 cells, the binding molecule can direct complement mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of an anti-HBsAg monospecific IgG1 antibody with identical anti-HBsAg binding domains (equivalent by weight or by molar concentration) as measured, e.g., in µg/ml or in nM. In certain aspects, where the HBsAg-expressing cell is a PLC/PRF/5 cell line or an HBsAg-transfected cell, the binding molecule can direct complement-mediated killing with an $IC_{50}$ at least one-fold, at least two-fold, at least three-fold, at least four-fold, at least five-fold, at least ten-fold, at least 20-fold, at least 30-fold, at least 40-fold, at least 50-fold, at least 60-fold, at least 70-fold, at least 80-fold, at least 90-fold, or at least 100-fold lower than the $IC_{50}$ of an equivalent amount of an anti-HBsAg monospecific IgG1 antibody with identical anti-HBsAg binding domains, as measured, e.g., in molar or molecular weight equivalents.

In certain aspects, a pentameric binding molecule comprising five identical binding units each comprising two identical anti-HBsAg binding domains as provided herein, plus a wild-type or modified J-chain as provided herein can exhibit increased potency in a CDC assay performed in cells exhibiting lower HBV antigen expression levels. For example, a pentameric anti-HBsAg binding molecule with a wild-type or modified J-chain as provided herein, tested in a CDC assay using the HBV-expressing PLC/PRF/5 cells or HepG2.2.15 cells, can direct complement-mediated killing with an $IC_{50}$ at least one-fold, at least two-fold, at least three-fold, at least four-fold, at least five-fold, at least ten-fold, at least twenty-fold, at least thirty-fold, at least forty-fold, at least 50-fold, at least 100-fold, at least 150-fold, at least 200-fold or more lower than the $IC_{50}$ of an equivalent amount of an anti-HBsAg monospecific IgG1 antibody with identical anti-HBsAg binding domains, as measured, e.g., in molar or molecular weight equivalents.

In certain aspects, a bispecific pentameric binding molecule comprising five identical binding units each comprising two identical anti-HBV binding domains as provided herein, plus a modified J-chain capable of binding to human CD3, e.g., V15J or J15V as provided herein, can exhibit increased potency in a TDCC assay. For example, a pentameric anti-HBsAg binding molecule with a modified J-chain capable of binding to human CD3, e.g., V15J or J15V as provided herein, tested in a T-cell activation assay, e.g., using the HBsAg-expressing PLC/PRF/5 cells or HepG2.2.15 cells co-cultured with engineered Jurkat T-cells, can facilitate T-cell mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of a bispecific anti-HBsAg IgG1 antibody with identical anti-HBsAg binding domain(s) that binds HBV antigen-expressing cells and T-cells, e.g., a single binding unit bispecific anti-HBsAg× anti-CD3 molecule as measured, e.g., in molar or molecular weight equivalents.

In certain aspects, a monospecific or bispecific pentameric binding molecule comprising five identical binding units each comprising two identical anti-HBsAg binding domains as provided herein, plus a wild-type J-chain or a modified J-chain capable of binding to human CD3, e.g., V15J or J15V as provided herein, can exhibit increased potency in a whole-blood in vitro cytotoxicity assay. For example, a pentameric anti-HBV binding molecule plus a wild-type or modified J-chain capable of binding to human CD3, e.g., V15J or J15V as provided herein, tested in an appropriate in vitro cytotoxicity assay using the HBsAg-expressing PLC/PRF/5 cell line co-cultured with Hirudin anti-coagulated human blood can achieve killing of the PLC/PRF/5 cells or HepG2.2.15 cells with an $IC_{50}$ at least one-fold, at least two-fold, at least three-fold, at least four-fold, at least five-fold, at least ten-fold, at least twenty-fold, at least thirty-fold, at least forty-fold, at least 50-fold, at least 100-fold, at least 150-fold, at least 200-fold or more lower than the $IC_{50}$ of an equivalent amount of an anti-HBsAg monospecific IgG1 antibody with identical anti-HBsAg binding domains, as measured, e.g., in molar or molecular weight equivalents, or of a bispecific anti-HBsAg IgG1 antibody with identical anti-HBsAg binding domain(s) that binds HBV antigen-expressing cells and T-cells, e.g., a bispecific single binding unit anti-HBsAg×anti-CD3 molecule, as measured, e.g., in molar or molecular weight equivalents.

In certain aspects, a monospecific or bispecific pentameric binding molecule comprising five identical binding units each comprising two identical anti-HBsAg binding domains as provided herein, plus a wild-type J-chain or a modified J-chain capable of binding to human CD3, e.g., V15J or J15V as provided herein, can exhibit increased HBsAg-expressing or HBV-infected cell killing in vivo, for example in a humanized mouse model as described elsewhere herein.

Polynucleotides, Vectors, and Host Cells

The disclosure further provides a polynucleotide, e.g., an isolated, recombinant, and/or non-naturally-occurring polynucleotide, comprising a nucleic acid sequence that encodes a polypeptide subunit of the dimeric, hexameric, or pentameric binding molecule as described above. By "polypeptide subunit" is meant a portion of a binding molecule, binding unit, or antigen binding domain that can be independently translated. Examples include, without limitation, an antibody variable domain, e.g., a VH or a VL, a single chain Fv, an antibody heavy chain, an antibody light chain, an antibody heavy chain constant region, an antibody light chain constant region, and/or any fragment thereof.

In certain aspects, the polypeptide subunit can comprise an IgM or an IgA heavy chain constant region or fragment thereof, and VH portion of an HBV antigen binding domain. In certain aspects the polynucleotide can encode a polypeptide subunit comprising a human IgM or IgA constant region or fragment thereof fused to the C-terminal end of a VH, where the VH comprises the HCDR1, HCDR2, and HCDR3 regions, or the HCDR1, HCDR2, and HCDR3 regions containing one or two single amino acid substitutions of a VH comprising the amino acid sequence SEQ ID NO: 1, SEQ ID NO: 2, SEQ ID NO: 4, SEQ ID NO: 5, SEQ ID NO: 7, SEQ ID NO: 7, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 26, SEQ ID NO: 26, SEQ ID NO: 26, SEQ ID NO: 30, SEQ ID NO: 32, SEQ ID NO: 34, SEQ ID NO: 34, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 62, SEQ ID NO: 73, or SEQ ID NO: 75.

In certain aspects, the polypeptide subunit can comprise an antibody VL portion of an HBV antigen binding domain as described above. In certain aspects the polypeptide subunit can comprise a human antibody light chain constant region or fragment thereof fused to the C-terminal end of a VL, where the VL comprises LCDR1, LCDR2, and LCDR3 regions, or the LCDR1, LCDR2, and LCDR3 regions containing one or two single amino acid substitutions of a VL comprising the amino acid sequence SEQ ID NO: 3, SEQ ID NO: 6, SEQ ID NO: 8, SEQ ID NO: 9, SEQ ID NO: 11, SEQ ID NO: 15, SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 74, or SEQ ID NO: 76.

In certain aspects the polynucleotide can encode a polypeptide subunit comprising a human IgM or IgA constant region or fragment thereof fused to the C-terminal end of a VH, where the VH comprises an amino acid sequence at least 60%, at least 65%, at least 70%, at least 75%, at least 80%, at least 85%, at least 90%, at least 95% or 100% identical to any one or more of the amino acid sequences of SEQ ID NO: 1, SEQ ID NO: 2, SEQ ID NO: 4, SEQ ID NO: 5, SEQ ID NO: 7, SEQ ID NO: 7, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 26, SEQ ID NO: 26, SEQ ID NO: 26, SEQ ID NO: 30, SEQ ID NO: 32, SEQ ID NO: 34, SEQ ID NO: 34, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 62, SEQ ID NO: 73, or SEQ ID NO: 75

In certain aspects the polynucleotide can encode a polypeptide subunit comprising a human light chain constant region or fragment thereof fused to the C-terminal end of a VL, where the VL comprises an amino acid sequence at least at least 60%, at least 65%, at least 70%, at least 75%, at least 80%, at least 85%, at least 90%, at least 95% or 100% identical to any one or more of SEQ ID NO: 3, SEQ ID NO: 6, SEQ ID NO: 8, SEQ ID NO: 9, SEQ ID NO: 11, SEQ ID NO: 15, SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 74, or SEQ ID NO: 76.

Thus, to form the antigen binding domains, the variable regions of antibodies that specifically bind to a hepatitis B antigen can be inserted into expression vector templates for IgM and/or IgA structures, thereby creating multimeric binding molecules having at least two bivalent binding units. In brief, nucleic acid sequences encoding the heavy and light chain variable domain sequences can be synthesized or amplified from existing molecules, and inserted into vectors in the proper orientation and in frame such that upon expression, the vector will yield a full length heavy or light chain. Vectors useful for these purposes are known in the art. Such vectors can also comprise enhancer and other sequences needed to achieve expression of the desired chains. Multiple vectors or single vectors can be used. These vectors are transfected into host cells and then the chains are expressed and purified. Upon expression the chains form fully functional multimeric binding molecules, as has been reported in the literature. The fully assembled multimeric binding molecules can then be purified by standard methods. The expression and purification processes can be performed at commercial scale, if needed.

The disclosure further provides a composition comprising two or more polynucleotides, where the two or more polynucleotides collectively can encode a dimeric, hexameric, or pentameric binding molecule as described above. In certain aspects the composition can include a polynucleotide encoding an IgM and/or IgA heavy chain or fragment thereof, e.g., a human IgM and/or IgA heavy chain as described above where the IgM and/or IgA heavy chain comprises at least the VH of an HBV antigen binding domain, and a polynucleotide encoding a light chain or fragment thereof, e.g., a human kappa or lambda light chain that comprises at least the VL of an HBV antigen binding domain. A polynucleotide composition as provided can further include a polynucleotide encoding a J-chain, e.g., a human J-chain, or a fragment thereof or a variant thereof. In certain aspects the polynucleotides making up a composition as provided herein can be situated on two or three separate vectors, e.g., expression vectors. Such vectors are provided by the disclosure. In certain aspects two or more of the polynucleotides making up a composition as provided herein can be situated on a single vector, e.g., an expression vector. Such a vector is provided by the disclosure.

The disclosure further provides a host cell, e.g., a prokaryotic or eukaryotic host cell, comprising a polynucleotide or two or more polynucleotides encoding a dimeric, pentameric, or hexameric HBV binding molecule as provided herein, or any subunit thereof, a polynucleotide composition as provided herein, or a vector or two, three, or more vectors that collectively encode a dimeric, pentameric, or hexameric HBV binding molecule as provided herein, or any subunit thereof. In certain aspects a host cell provided by the disclosure can express a dimeric, pentameric, or hexameric HBV binding molecule as provided by this disclosure, or a subunit thereof.

In a related aspect, the disclosure provides a method of producing a dimeric, pentameric, or hexameric HBV binding molecule as provided by this disclosure, where the method comprises culturing a host cell as described above, and recovering the binding molecule.

Methods of Use

This disclosure provides improved methods for controlling hepatitis B virus (HBV) proliferation, latency, or maintenance in chronically-infected cells, e.g., controlling viral attachment, infectivity, replication, latency, egress, etc., e.g., across two or more subtypes, using a dimeric IgA-based HBV binding molecule, or pentameric or hexameric IgM-based HBV binding molecule. The methods described below can utilize multimeric binding molecules comprising HBV antigen binding domains derived from any new or existing HBV antibodies, including without limitation, the antibodies and corresponding VH and VL sequences disclosed in the references set forth in Table 2, or variants, derivatives, or analogs thereof, where the dimeric, pentameric, or hexameric binding molecule, e.g., an IgM antibody can provide improved potency as compared to a corresponding single binding unit antibody, fragment, variant, derivative, or analog, as disclosed and explained above. Based on this disclosure, construction of a dimeric IgA binding molecule, or pentameric or hexameric IgM binding molecule comprising any HBV-specific antigen binding domain of interest is well within the capabilities of a person of ordinary skill in the art. The increased avidity of IgA or IgM forms of anti-HBV antibodies can result in a more potent therapeutic antibody that can bind HBV infected cells with very low density of HBV surface proteins, allowing for improved virus neutralization, improved HBV-infected cell killing, e.g., through complement or T-cell mediated cytotoxicity, prevention diseases or conditions caused by, or exacerbated by infection with HBV, including, but not limited to acute hepatitis, chronic hepatitis, liver inflammation, cirrhosis of the liver, liver failure, hepatocellular carcinoma (HCC), or any combination thereof, and more efficient clearance of HBV from infected patients. The improved binding characteristics of such compositions can, for example, allow a reduced dose to be used, or can result in more effective neutralization and/or clearance of viruses or virus-infected cells resistant to a corresponding single binding unit antibody. By "resistant" is meant any degree of reduced activity of an HBV antibody, on neutralizing HBV, clearing HBV or HBV-infected cells, controlling infectivity, replication, release, etc.

In certain aspects, this disclosure provides a method of treating a disease or condition caused by or exacerbated by hepatitis B virus (HBV) infection in a patient, comprising administering to a patient infected with HBV or susceptible to HBV infection a dimeric, pentameric, or hexameric binding molecule, e.g., an IgM antibody as provided herein. As described elsewhere herein, the provided binding molecules can exhibit increased potency relative to a reference single binding unit antibody comprising equivalent or identical antigen binding domain(s) e.g., a monospecific, single binding unit IgG antibody or fragment thereof that specifically binds to the same HBV epitope, e.g., an epitope on the pre-S1 region of the HBV surface antigen, as the antigen binding domain that comprises a VH with the amino acid sequence SEQ ID NO: 62 and a VL with the amino acid sequence SEQ ID NO: 6, for example. In certain aspects, the disease or condition is acute hepatitis, chronic hepatitis, liver inflammation, cirrhosis of the liver, liver failure, hepatocellular carcinoma (HCC), or any combination thereof. In certain aspects a patient to be treated with a binding molecule, e.g., an IgM antibody as provided herein can exhibit certain diseases symptoms such as, but not limited to: increased viral load, virus shedding, abdominal pain, dark urine, fever, joint pain, loss of appetite, nausea and vomiting, weakness and fatigue, jaundice, or a combination thereof. In certain aspects, the disease symptoms can be alleviated or reduced to a greater extent by a binding molecule provided herein than by an equivalent single binding unit antibody.

In certain aspects, this disclosure provides a method for directing improved neutralization of HBV, where the method includes contacting an HBV, or an HBV-infected cell with a dimeric, pentameric, or hexameric binding molecule, e.g., an IgM antibody as described herein, where the binding molecule can direct virus neutralization at higher potency than an equivalent amount of a reference single binding unit binding molecule, e.g., a monospecific, single binding unit IgG antibody or fragment thereof that specifically binds to the same HBV epitope, e.g., an epitope on the pre-S1 region of the HBV surface antigen, as the antigen binding domain that comprises a VH with the amino acid sequence SEQ ID NO: 62 and a VL with the amino acid sequence SEQ ID NO: 6, for example. For instance, the antigen binding domain can comprise a VH amino acid sequence at least 60%, at least 65%, at least 70%, at least 75%, at least 80%, at least 85%, at least 90%, at least 95% or 100% identical to SEQ ID NO: 1 or SEQ ID NO: 2, and a VL amino acid sequence at least 60%, at least 65%, at least 70%, at least 75%, at least 80%, at least 85%, at least 90%, at least 95% or 100% identical to SEQ ID NO: 3. In another aspect, the antigen binding domain can comprise a VH amino acid sequence at least 60%, at least 65%, at least 70%, at least 75%, at least 80%, at least 85%, at least 90%, at least 95% or 100% identical to SEQ ID NO: 5 or SEQ ID NO: 62, and a VL amino acid sequence at least 60%, at least 65%, at least 70%, at least 75%, at least 80%, at least 85%, at least 90%, at least 95% or 100% identical to SEQ ID NO: 6. In certain aspects a dimeric, pentameric, or hexameric binding molecule, e.g., an IgM antibody as provided herein can direct virus neutralization of two or more HBV subtypes at higher potency than an equivalent amount of a monospecific, single binding unit HBV monoclonal antibody, e.g., the corresponding IgG antibody or fragment thereof, where the antibody is, or comprises the same VH and VL regions as, e.g., the VH and VL sequences set forth in Table 2. In certain aspects, the hexameric or pentameric binding molecule, e.g., an IgM antibody or fragment thereof, comprises a heavy chain comprising the amino acid sequence SEQ ID NO: 58, and a light chain comprising the amino acid sequence SEQ ID NO: 59. In certain aspects, the hexameric or pentameric binding molecule, e.g., an IgM antibody or fragment thereof, comprises a heavy chain comprising the amino acid sequence SEQ ID NO: 63, and a light chain comprising the amino acid sequence SEQ ID NO: 59.

For instance, methods include screening of various binding molecules whose affinities and/or avidities for infectious HBV viral particles, or other infectious viral particles, have not been determined. The methods provided herein can be employed to identify binding molecules that bind to the surface of infectious hepatitis B virus (HBV) viral particles, on the surface if HBV infected cells, or a combination thereof, with greater affinity, greater avidity, or a combination thereof, than binding to HBV subviral particles. The increased avidity of IgA or IgM forms of anti-HBV can result in a more potent therapeutic antibody that can bind those infected cells with very low density of HBV surface proteins, allowing more efficient clearance of HBV from infected patients. Similarly the methods provided herein can be employed to identify binding molecules that bind to the surface of other infectious viral particles or virus-infected cells with great affinity, greater avidity, or both, than binding to non-infectious versions of the same virus. Thus, a binding molecule as provided herein that possesses the advantageous properties discussed above can be used in a method for binding to infectious HBV or other viral particles. Due to the advantageous properties of a multimeric binding molecule as provided herein, binding molecules can be identified that bind infectious HBV particles or other infectious viral particles with a higher avidity or affinity, or combination thereof, than binding to subviral (non-infectious) HBV viral particles or other non-infectious viral particles. Thus, methods are disclosed wherein such binding molecules with such properties can be identified by detecting binding to infectious and non-infectious viral particles and comparing the binding affinities and/or avidities to identify additional binding molecules possessing advantageous properties. Binding molecules that bind to infectious particles with a higher avidity or affinity, or combination thereof, than binding to subviral (non-infectious) viral particles can be selected by this method.

Such methods can generally be performed by contacting a test binding molecule with an infectious viral particle and measuring the affinity and/or avidity of the test binding molecule for binding to an infectious viral particle. The same test binding molecule is also contacted with a non-infectious HBV subviral particle or other non-infectious viral particle, and the affinity and/or avidity of the test binding molecule for binding to an HBV subviral particle or other non-infectious particle can be detected. The results of these two tests are compared thereby identifying test compounds (binding molecules) in which the affinity and/or avidity measured for binding to infectious HBV particles or other infectious viral particles is higher than the affinity and/or for binding to non-infectious HBV sub-viral particles or other non-infectious particles.

In this manner, additional binding molecules useful in the methods provided herein can be identified and utilized.

Similarly, methods are disclosed wherein various test compounds (binding molecules) whose affinities and/or avidities for HBV-infected cells or other viral infected cells have not been determined. The methods provided herein can be employed to identify binding molecules that bind to the surface of HBV-infected cells or other viral infected cells with greater affinity, greater avidity, or a combination thereof, than binding to identical cells which are not infected with the virus, or binding to non-infectious viral particles. Thus, a binding molecule possessing the advantageous properties discussed above can be used in a method for preferential binding to HBV-infected cells or other viral infected cells. Due to the advantageous properties of a multimeric binding molecule as provided herein, the binding molecule can bind HBV-infected cells or other viral infected cells with a higher avidity and/or affinity, than binding to similar non-infected cells, or to non-infectious viral particles. Thus, methods are disclosed where virus-infected and non-infected cells, as well as non-infectious viral particles, and comparing the binding affinities and/or avidities to identify a difference in binding. Binding molecules which bind to HBV-infected cells or other viral-infected cells with a higher avidity and/or affinity, than binding to similar cells which are not infected with HBV or other virus, or to non-infectious viral particles can be selected by this method.

This screening method can be accomplished by contacting a test binding molecule with an HBV-infected cell (or other viral infected cell) and measuring the affinity and/or avidity of the test binding molecule for binding to the HBV- or virus-infected cell, and contacting the same test same binding molecule with a cell not infected with HBV or other virus, or to non-infectious viral particles, and measuring the affinity and/or avidity of the test binding molecule for binding to a cell not infected with HBV or other virus, or to non-infectious viral particles, wherein the non-infected cell is identical to the HBV-infected cell except that it is not infected. The binding results for this test compound, or any number of test compounds, can then be compared, thereby identifying a test compound in which the affinity and/or avidity is higher for infected cells than non-infected cells or non-infectious viral particles.

The cells in such methods can be any cell capable of being infected by HBV or other virus, such as a human cell.

In certain aspects the HBV antigen binding domain of the dimeric, pentameric, or hexameric binding molecule, e.g., an IgM antibody comprises six immunoglobulin complementarity determining regions HCDR1, HCDR2, HCDR3, LCDR1, LCDR2, and LCDR3, wherein at least one, at least two, at least three, at least four, at least five, or at least six CDRs are related to the corresponding CDRs of any one of the HBV antibodies set forth in Table 2, e.g., those that possess affinity for the hepatitis B epitope HBsAg, e.g., the pre-S1 region.

A dimeric, hexameric or pentameric binding molecule for use in the methods provided herein, is a binding molecule with two, five or six "binding units" as defined herein, that can specifically bind to two or more HBV subtypes, e.g., A, B, C, D, E, F, G and/or H. In certain aspects, a dimeric, pentameric or hexameric binding molecule for use in the methods provided herein comprises two, five or six bivalent binding units, respectively, where each binding unit includes two IgA heavy chain constant regions or fragments thereof (for IgA-based binding molecules), or two IgM heavy chain constant regions or fragments thereof (for IgM-based molecules). In certain aspects, the two IgA or IgM heavy chain constant regions are human heavy chain constant regions.

Dimeric, pentameric, or hexameric HBV binding molecules for use in the methods provided herein can possess advantageous structural or functional properties compared to other binding molecules. For example, a dimeric, pentameric, or hexameric binding molecule for use in the methods provided herein can possess improved binding characteristics in a biological assay, as described above, either in vitro or in vivo, than a corresponding reference single binding unit, e.g., IgG or a variant, analog, or derivative thereof, as also described above. Biological assays include, but are not limited to in vitro neutralization assays, hemagglutination inhibition assays, cell attachment assays, viral egress assays, immunohistochemical assays, direct cytotoxicity assays, complement-mediated cytotoxicity assays, etc. In vivo efficacy models include, but are not limited to immune-compromised murine models with diminished endogenous liver capacity and re-constituted with human hepatocytes. Alternatively, dimeric, pentameric, or hexameric binding molecules can be tested in vivo using non-human primate models of HBV infection to evaluate HBV clearance (see Example 7, below).

Pharmaceutical Compositions and Administration Methods

Methods of preparing and administering a multimeric, e.g., a dimeric, pentameric, or hexameric binding molecule, e.g., an IgM antibody as provided herein to a subject in need thereof are well known to or are readily determined by those skilled in the art in view of this disclosure. The route of administration of a multimeric binding molecule can be, for example, oral, parenteral, by inhalation or topical. The term parenteral as used herein includes, e.g., intravenous, intraarterial, intraperitoneal, intramuscular, subcutaneous, rectal, or vaginal administration. While these forms of administration are contemplated as suitable forms, another example of a form for administration would be a solution for injection, in particular for intravenous or intra-arterial injection or drip. A suitable pharmaceutical composition can comprise a buffer (e.g. acetate, phosphate or citrate buffer), a surfactant (e.g. polysorbate), and in some embodiments a stabilizer agent (e.g. human albumin), etc.

As discussed herein, a dimeric, pentameric, or hexameric HBV binding molecule as provided herein can be administered in a pharmaceutically effective amount for the in vivo treatment of diseases or disorders in which it is desirable to deplete B cells. In this regard, it will be appreciated that the disclosed multimeric binding molecules can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a dimeric, pentameric, or hexameric HBV binding molecule as provided herein means an amount sufficient to achieve effective binding to a target and to achieve a therapeutic benefit. Suitable formulations are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a dimeric, pentameric, or hexameric HBV binding molecule that can be combined with carrier materials to produce a single dosage form will vary depending, e.g., upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the disclosure, a dimeric, pentameric, or hexameric HBV binding molecule as provided herein can be administered to a subject in need of therapy in an amount sufficient to produce a therapeutic effect. A multimeric binding molecule as provided herein can be administered to the subject in a conventional dosage form prepared by combining the antibody or antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of a dimeric, pentameric, or hexameric HBV binding molecule, that when administered brings about a positive therapeutic response with respect to treatment of a patient with a disease or condition to be treated.

Therapeutically effective doses of the compositions disclosed herein, for the treatment of a disease or condition caused by, or exacerbated by infection with hepatitis B virus, can vary depending upon many different factors, including means of administration, target site, physiological state of the patient, whether the patient is human or an animal, other medications administered, and whether treatment is prophylactic or therapeutic. In certain aspects, the subject or patient is a human, but non-human mammals including transgenic mammals can also be treated. Treatment dosages can be titrated using routine methods known to those of skill in the art to optimize safety and efficacy.

The amount of a dimeric, pentameric, or hexameric binding molecule, e.g., an IgM antibody to be administered is readily determined by one of ordinary skill in the art without undue experimentation given this disclosure. Factors influencing the mode of administration and the respective amount of a multimeric binding molecule include, but are not limited to, the severity of the disease, the history of the disease, and the age, height, weight, health, and physical condition of the individual undergoing therapy. Similarly, the amount of a dimeric, pentameric, or hexameric HBV binding molecule to be administered will be dependent upon the mode of administration and whether the subject will undergo a single dose or multiple doses of this agent.

This disclosure also provides for the use of a dimeric, pentameric, or hexameric HBV binding molecule in the manufacture of a medicament for treating, preventing, or managing a disease or condition caused by, or exacerbated by infection with hepatitis B virus.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; W.H. Freeman & Co.); Roitt et al.

(2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Surface Antigen Preparation

Surface antigens can be prepared as previously reported. (See, for instance, Short et al., *J. Mol. Biol.* (2009) 390, 135-141). In one method, HBsAg is isolated from the blood of HBV carriers. Frozen serum containing HBV can be obtained, e.g., from the Diagnostics, Development and Research Division, National Blood Service, Colindale Centre, London, UK. Individual packs are then thawed and centrifuged (3700×g for 20 min) and the supernatant layered over 0.5 ml of 20% sucrose in TBS (in 5.1-ml tubes) and centrifuged (266,000×g for 30 min). The pellets are resuspended in 20 mM Tris chloride (pH 7.4) and 140 mM NaCl (Tris-buffered saline, TBS) (after leaving wetted overnight at 4° C. to soften), pooled and subjected to equilibrium centrifugation with CsCl (0.22 g/ml initial concentration) (266,000×g for 72 h). Fractions (250 µl) are taken from the gradient and monitored by electron microscopy and by DNA extraction and analysis for hepatitis B DNA. The fractions containing the most suitable HBsAg particles, which are also free of hepatitis B DNA (and thus, virus), are taken and dialyzed against TBS for use. Multiple forms of the surface antigen HBsAg (Long, PreS1-PreS2-S; Medium, PreS2-S; Short, S), both native and recombinant as well as peptide fragments, were from commercial sources, as were forms of other HBV proteins.

Example 2: HBV Capsid and Virion Isolation

Capsid and virion isolation methods are well known in the art and can be conducted by any number of known means. (See, for instance, Dryden, *Molecular Cell*, 22:843-850, Jun. 23, 2006, suppl.). In one method of capsid isolation, freshly dissected whole livers are perfused with saline solution. The livers are then homogenized in lysis buffer (for instance, 0.25 M sucrose, 1 mM $MgCl_2$, 5 mM Tris (pH 7.4)) and supplemented with complete protease inhibitor (Roche Applied Science, Indianapolis, Ind.). The supernatant of each homogenate is obtained by centrifugation for 15 min at 4° C. and 11,000 rpm in an SW40 rotor. An aliquot of the supernatant is removed for the purpose of performing an HBV-specific Southern blot analysis. The remainder is then layered onto a 30% sucrose cushion (0.73 M sucrose in phosphate buffered saline (PBS)), and viral particles are pelleted by centrifugation for 5 hrs at 4° C. and 40,000 rpm in an SW40 rotor. The pellets are then resuspended in 1 ml of CsCl-solution [3.3 g CsCl dissolved in 10 ml PBS-solution (1×PBS, 20 mM EDTA, and 1× complete protease inhibitor cocktail)]. The resuspended material is then transferred into quick seal tubes (Beckman Instruments, Palo Alto, Calif.). The tubes are filled with CsCl solution, sealed, and HBV particles banded by centrifugation for 18 hrs at 11° C. and 60,000 rpm in a TI80 rotor.

The tubes are bottom-punctured, and fractions are collected. Fractions containing capsid are pooled, diluted in PBS and then concentrated. The filtrates are combined, and pelleted an additional 30 min. The sample is then divided and loaded on preformed CsCl gradients (ρ 1.2-1.4). After centrifugation for 3 hrs at 4° C. and 38,000 rpm, fractions (200 µl each) are collected by pipette, their refractive index is measured, and equivalent fractions are pooled.

To remove the CsCl and concentrate the pooled fractions, samples are pelleted and resuspended three times in PBS, twice using, e.g., a TLA100.4 rotor and finally using, e.g., a TLA100.2 rotor, each for 1 hr at 45,000 rpm and 4° C.

In one method of virion isolation, multiple plasmapheresis units obtained from one or more HBV positive individuals are pooled, filtered through sterile cheesecloth, and virions are purified as described (Kaplan 1973; *J. Virol.* 12, 995-1005). Briefly, polycarbonate tubes are loaded with 65 ml of the plasma pool, which is subjected to centrifugation for 3 hrs at 21,000 rpm at 5° C. in an SW30 rotor. The supernatants are decanted, and the tubes are reloaded with another 65 ml of the plasma pool, and the centrifugation is repeated. Two pellets, each from 130 ml of starting material, are resuspended in ~7 ml of PBS each, pooled and subjected to centrifugation for 4 hrs in an SW30 rotor through a 7 ml cushion of 20% (w/w) sucrose in PBS at 30,000 rpm and at 5° C. The pellet is resuspended in PBS to a final concentration of 50× compared with the original starting material, divided into 50 µl aliquots and frozen at −80° C.

Alternatively, HBV virions can be produced following methods outlined by Kim (FEBS Letters 2015; 589, 193-200). Briefly, viral particles are produced by transient transfection of HepG2 cells (ATCC HB-8065) with a vector containing a full-length HBV genome (e.g., pHBVEcoR1-; Gripon 1995; Virol. 213(2), 292-299). The viral particles are then concentrated 50-fold by PEG precipitation (Le Seyed 1999; *J. Virol.* 73(3), 2052-2057). The genotype of the HBV virus will be dependent upon the vector used.

Example 3: Engineered IgM Binding Molecules Specific for HBV

VH and VL regions of various HBV antibodies provided herein can be cloned into IgG and IgM backgrounds by standard methods, or by commercial contractors.

HBV24: The VH and VL of a humanized antibody specific for pre-S1 antigen provided in U.S. Pat. No. 8,420,353, presented herein as SEQ ID NO: 5 and SEQ ID NO: 6, respectively, were cloned into appropriate vectors to encode the human IgG and IgM heavy chains comprising the amino acid sequences SEQ ID NO: 84 and SEQ ID NO: 58, respectively, and the kappa light chain comprising SEQ ID NO: 59. SEQ ID NOs 58 and 58 are listed above. The vectors were transfected in to HEK293 cells (with, where appropriate, a vector encoding a human wild-type or modified J-chain as described below) and expression was permitted, producing the IgG molecule HBV24G and the IgM molecule HBV24M.

HBV24G Heavy Chain

SEQ ID NO: 84

QVQLVQSGAEVKAPGASVKVSCKASGYTFTSAWMNWVRQAPG

QGLEWMGRIYPSGGSTSYAQKFQGRVTMTADKSTSTVYMELSSL

RSEDTAVYYCAREYRVARWGQGTLVTVSSASTKGPSVFPLAPSS

KSTSGGTAALGCLVKDYFPEPVTVSWNSGALTSGVHTFPAVLQSS

```
GLYSLSSVVTVPSSSLGTQTYICNVNHKPSNTKVDKKVEPKSCDK

THTCPPCPAPELLGGPSVFLEPPKPKDTLMISRTPEVTCVVVDVSH

EDPEVKFNWYVDGVEVHNAKTKPREEQYNSTYRVVSVLTVLHQ

DWLNGKEYKCKVSNKALPAPIEKTISKAKGQPREPQVYTLPPSRD

ELTKNQVSLTCLVKGFYPSDIAVEWESNGQPENNYKTTPPVLDSD

GSFFLYSKLTVDKSRWQQGNVFSCSVMHEALHNHYTQKSLSLSP

GK
```

HBV23: The VH and VL of the human antibody specific for the S region of HBsAg provided in Cerino, et al., (2015) *PLOS one* 10(4):e0125704. doi: 10.1371, presented herein as SEQ ID NO: 73 and SEQ ID NO: 74, respectively, were cloned into appropriate vectors to encode the human IgG and IgM heavy chains comprising the amino acid sequences SEQ ID NO: 85 and SEQ ID NO: 80, respectively, and the lambda light chain comprising SEQ ID NO: 81. The vectors were transfected in to HEK293 cells (with, where appropriate, a vector encoding a human wild-type or modified J-chain as described below) and expression was permitted, producing the IgG molecule HBV23G and the IgM molecule HBV23M.

```
HBV23G Heavy Chain
                                            SEQ ID NO: 85
MDPKGSLSWRILLFLSLAFELSYGEVQVLESGGGLVQPGGSLRLS

CAASGFRESSYAMSWVRQAPGKGLEWVSGISGTGENTYYADSVK

GRFTISRDNSKNTLYVQMNSLRAEDTAVYYCAKDAILGSGHPWY

FHVWGRGTLVTVSSASTKGPSVFPLAPSSKSTSGGTAALGCLVKD

YFPEPVTVSWNSGALTSGVHTFPAVLQSSGLYSLSSVVTVPSSSLG

TQTYICNVNHKPSNTKVDKKVEPKSCDKTHTCPPCPAPELLGGPS

VFLEPPKPKDTLMISRTPEVTCVVVDVSHEDPEVKFNWYVDGVE

VHNAKTKPREEQYNSTYRVVSVLTVLHQDWLNGKEYKCKVSNK

ALPAPIEKTISKAKGQPREPQVYTLPPSRDELTKNQVSLTCLVKGF

YPSDIAVEWESNGQPENNYKTTPPVLDSDGSFFLYSKLTVDKSRW

QQGNVFSCSVMHEALHNHYTQKSLSLSPG

HBV23M Heavy Chain
                                            SEQ ID 80
MDPKGSLSWRILLFLSLAFELSYGEVQVLESGGGLVQPGGSLRLS

CAASGFRFSSYAMSWVRQAPGKGLEWVSGISGTGENTYYADSVK

GRFTISRDNSKNTLYVQMNSLRAEDTAVYYCAKDAILGSGHPWY

FHVWGRGTLVTVSSGSASAPTLFPLVSCENSPSDTSSVAVGCLAQ

DFLPDSITFSWKYKNNSDISSTRGFPSVLRGGKYAATSQVLLPSKD

VMQGTDEHVVCKVQHPNGNKEKNVPLPVIAELPPKVSVFVPPRD

GFFGNPRKSKLICQATGFSPRQIQVSWLREGKQVGSGVTTDQVQA

EAKESGPTTYKVTSTLTIKESDWLSQSNIFTCRVDHRGLTFQQNAS

SMCVPDQDTAIRVFAIPPSFASIFLTKSTKLTCLVTDLTTYDSVTIS

WTRQNGEAVKTHTNISESHPNATFSAVGEASICEDDWNSGERFTC

TVTHTDLPSPLKQTISRPKGVALHRPDVYLLPPAREQLNLRESATI

TCLVTGFSPADVFVQWMQRGQPLSPEKYVTSAPMPEPQAPGRYF

AHSILTVSEEEWNTGETYTCVVAHEALPNRVTERTVDKSTGKPTL

YNVSLVMSDTAGTCY

HBV23M Light Chain
                                            SEQ ID 81
MSVPTQVLGLLLLWLTDARCSYVLTQPPSVSVAPGQTARMTCGG

NNIGSESVHWFQQKPGQAPVLVVYDDSDRPSGIPERFSGSNSGNT

ATLTISRVEAGDEADYYCQVWDSSSDHAVFGGGTQLTVLGQPKA

APSVTLFPPSSEELQANKATLVCLISDFYPGAVTVAWKADSSPVK

AGVETTTPSKQSNNKYAASSYLSLTPEQWKSHRSYSCQVTHEGST

VEKTVAPTECS*
```

HBV19: The VH and VL of a human antibody specific for the PreS1 region of HBsAg serotype ay provided in Pizarro, et al., *FEBS Letters* 509:463-468 (2001), presented herein as SEQ ID NO: 75, and SEQ ID NO: 76, respectively, were cloned into appropriate vectors to encode the human IgG and IgM heavy chains comprising the amino acid sequences SEQ ID NO: 86 and SEQ ID NO: 82, respectively, and the kappa light chain comprising SEQ ID NO: 83. The vectors were transfected in to HEK293 cells (with, where appropriate, a vector encoding a human wild-type or modified J-chain as described below) and expression was permitted, producing the IgG molecule HBV19G and the IgM molecule HBV19M.

```
HBV19G Heavy Chain
                                            SEQ ID NO: 86
MDPKGSLSWRILLFLSLAFELSYGEVQLEESGGGLVKPGGSLKLS

CAASGFTFSSYAMSWVRQSPEKRLEWVAEVSSDGSYAYYPDTLT

GRFTISRDNAKNTLYLEMTSLRSEDTAMYYCASFNWDVAYWGQ

GTLVTVSAASTKGPSVFPLAPSSKSTSGGTAALGCLVKDYFPEPVT

VSWNSGALTSGVHTFPAVLQSSGLYSLSSVVTVPSSSLGTQTYICN

VNHKPSNTKVDKKVEPKSCDKTHTCPPCPAPELLGGPSVFLFPPKP

KDTLMISRTPEVTCVVVDVSHEDPEVKFNWYVDGVEVHNAKTKP

REEQYNSTYRVVSVLTVLHQDWLNGKEYKCKVSNKALPAPIEKT

ISKAKGQPREPQVYTLPPSRDELTKNQVSLTCLVKGFYPSDIAVE

WESNGQPENNYKTTPPVLDSDGSFFLYSKLTVDKSRWQQGNVFS

CSVMHEALHNHYTQKSLSLSPG

HBV19M Heavy Chain
                                            SEQ ID 82
MDPKGSLSWRILLFLSLAFELSYGEVQLEESGGGLVKPGGSLKLS

CAASGFTFSSYAMSWVRQSPEKRLEWVAEVSSDGSYAYYPDTLT

GRFTISRDNAKNTLYLEMTSLRSEDTAMYYCASFNWDVAYWGQ

GTLVTVSAGSASAPTLFPLVSCENSPSDTSSVAVGCLAQDFLPDSI

TFSWKYKNNSDISSTRGFPSVLRGGKYAATSQVLLPSKDVMQGT

DEHVVCKVQHPNGNKEKNVPLPVIAELPPKVSVFVPPRDGFFGNP

RKSKLICQATGFSPRQIQVSWLREGKQVGSGVTTDQVQAEAKESG

PTTYKVTSTLTIKESDWLSQSMFTCRVDHRGLTFQQNASSMCVPD
```

```
QDTAIRVFAIPPSFASIFLTKSTKLTCLVTDLTTYDSVTISWTRQNG

EAVKTHTNISESHPNATFSAVGEASICEDDWNSGERFTCTVTHTD

LPSPLKQTISRPKGVALHRPDVYLLPPAREQLNLRESATITCLVTGF

SPADVFVQWMQRGQPLSPEKYVTSAPMPEPQAPGRYFAHSILTVS

EEEWNTGETYTCVVAHEALPNRVTERTVDKSTGKPTLYNVSLVM

SDTAGTCY

HBV19M Light Chain
                                        SEQ ID 83
METDTLLLWVLLLWVPGSTGELVMTQSPSSLAVSVGEKVTMSCR

SSQSLLNTRTRKSYLAWFQQKPGQSPKMLIYWASTRESGVPDRFT

GSGSGTDFTLTISSVQAEDLAVYYCKQSYSLYTFGGGTKLEIKRTV

AAPSVFIFPPSDEQLKSGTASVVCLLNNFYPREAKVQWKVDNALQ

SGNSQESVTEQDSKDSTYSLSSTLTLSKADYEKHKVYACEVTHQG

LSSPVTKSFNRGEC
```

Two different J-chain variants were constructed with distinct fusion sites incorporating variable regions from the anti-CD3 antibody visilizumab (Nuvion). Shown below are the sequences for two J-chains with the scFv corresponding to visilizumab (V) (VH-$(GGGGS)_3$-VL, double-underlined) fused to the J-chain (italics) through a $(GGGGS)_3$ linker (SEQ ID NO: 72, underlined) containing 15 amino acids in two different orientations—V15J and J15V. Each sequence contains an N-terminal signal peptide that is shown without underlining or italics. In certain aspects, other signal peptide sequences can be substituted for the signal peptides shown here.

SEQ ID NO: 67: precursor modified J-chain sequence for V15J (DNA Sequence: SEQ ID NO: 66):
MGWSYIILFLVATATGVHSQVQLVQSGAEVKKPGASVKVSCKAS

GYTFISYTMHWVRQAPGQGLEWMGYINPRSGYTHYNQKLKDKA

TLTADKSASTAYMELSSLRSEDTAVYYCARSAYYDYDGFAYWG

QGTLVTVSSGGGGSGGGGSGGGGSDIQMTQSPSSLSASVGDRVTI

TCSASSSVSYMNWYQQKPGKAPKRLIYDTSKLASGVPSRFSGSGS

GTDFTLTISSLQPEDFATYYCQQWSSNPPTFGGGTKLEIKGGGGSG

GGGSGGGGS*QEDERIVLVDNKCKCARITSRIIRSSEDPNEDIVERNIR*

*IIVPLNNRENISDPTSPLRTRFVYHTSDLCKKCDPTEVELDNQIVTAT*

*QSNICDEDSATETCYTYDRNKCYTAVVPLVYGGETKNIVETATTPDAC*

*YPD*

SEQ ID NO: 68: mature modified J-chain sequence for V15J:
QVQLVQSGAEVKKPGASVKVSCKASGYTFISYTMHWVRQAPGQ

GLEWMGYINPRSGYTHYNQKLKDKATLTADKSASTAYMELSSLR

SEDTAVYYCARSAYYDYDGFAYWGQGTLVTVSSGGGGSGGGGS

GGGGSDIQMTQSPSSLSASVGDRVTITCSASSSVSYMNWYQQKPG

KAPKRLIYDTSKLASGVPSRFSGSGSGTDFTLTISSLQPEDFATYYC

QQWSSNPPTFGGGTKLEIKGGGGSGGGGSGGGGS*QEDERIVLVDN*

*KCKCARITSRIIRSSEDPNEDIVERNIRIIVPLNNRENISDPTSPLRT*

-continued

*RFVYHLSDLCKKCDPTEVELDNQIVTATQSNICDEDSATETCYTYDRN*

*KCYTAVVPLVYGGETKNIVETALTPDACYPD*

SEQ ID NO: 66:
ATGGGCTGGTCCTACATCATCCTCTTCCTCGTGGCCACAGCCAC

AGGCGTCCATAGCCAGGTGCAGCTGGTGCAGTCCGGCGCCGAA

GTGAAGAAGCCTGGCGCCAGCGTGAAGGTGAGCTGCAAGGCT

TCCGGCTACACCTTCATCTCCTACACCATGCACTGGGTGAGGC

AAGCTCCTGGCCAGGGCCTGGAGTGGATGGGATACATCAACCC

TCGGTCCGGCTATACCCACTACAATCAGAAGCTGAAGGACAAG

GCCACCCTGACCGCTGACAAGTCCGCCTCCACCGCTTACATGG

AGCTGTCCTCCCTGAGGTCCGAGGACACCGCCGTGTACTACTG

TGCCAGGTCCGCCTACTACGACTACGACGGATTCGCTTACTGG

GGCCAGGGCACCCTGGTGACAGTGAGCTCCGGAGGAGGAGGC

AGCGGCGGCGGCGGCAGCGGCGGCGGCGGCAGCGATATCCAG

ATGACCCAGAGCCCTTCCAGCCTGTCCGCTTCCGTGGGCGACA

GGGTGACCATCACCTGCAGCGCTTCCTCCTCCGTGTCCTACATG

AACTGGTACCAGCAGAAGCCTGGCAAGGCCCCCAAGAGGCTG

ATCTACGACACCTCCAAGCTGGCCTCCGGAGTGCCTTCCAGGT

TCAGCGGCTCCGGCTCCGGAACCGACTTCACCCTGACCATTAG

CTCCCTGCAGCCCGAGGACTTCGCCACCTACTACTGCCAGCAG

TGGTCCAGCAACCCTCCCACCTTCGGCGGCGGCACAAAGCTGG

AGATCAAGGGAGGAGGAGGATCCGGTGGTGGTGGTTCTGGCG

GAGGTGGATCCCAAGAAGATGAAAGGATTGTTCTTGTTGACAA

CAAATGTAAGTGTGCCCGGATTACTTCCAGGATCATCCGTTCTT

CCGAAGATCCTAATGAGGACATTGTGGAGAGAAACATCCGAA

TTATTGTTCCTCTGAACAACAGGGAGAATATCTCTGATCCCACC

TCACCATTGAGAACCAGATTTGTGTACCATTTGTCTGACCTCTG

TAAAAAATGTGATCCTACAGAAGTGGAGCTGGATAATCAGATA

GTTACTGCTACCCAGAGCAATATCTGTGATGAAGACAGTGCTA

CAGAGACCTGCTACACTTATGACAGAAACAAGTGCTACACAGC

TGTGGTCCCACTCGTATATGGTGGTGAGACCAAAATGGTGGAA

ACAGCCTTAACCCCAGATGCCTGCTATCCTGACTGA

SEQ ID NO: 70: precursor modified J-chain sequence for J15V (DNA sequence: SEQ ID NO: 69):
MKNHLLFWGVLAVFIKAVHVKA*QEDERIVLVDNKCKCARITSRIIRS*

*SEDPNEDIVERNIRIIVPLNNRENISDPTSPLRTREVYTILSDLCKKCD*

*PTEVELDNQIVTATQSNICDEDSATETCYTYDRNKCYTAVVPLVYGGE*

*TKMVETALTPDACYPD*GGGGSGGGGSGGGGSQVQLVQSGAEVKKPG

ASVKVSCKASGYTFISYTMHWVRQAPGQGLEWMGYINPRSGYT

HYNQKLKDKATLTADKSASTAYMELSSLRSEDTAVYYCARSAYY

DYDGFAYWGQGTLVTVSSGGGGSGGGGSGGGGSDIQMTQSPSSL

SASVGDRVTITCSASSSVSYMNWYQQKPGKAPKRLIYDTSKLASG

-continued
VPSRFSGSGSGTDFTLTISSLQPEDFATYYCQQWSSNPPTFGGGTK
LEIK SEQ ID NO: 71: mature modified J-chain sequence
for J15V:
QEDERIVLVDNKCKCARITSRIIRSSEDPNEDIVERNIRIIVPLNNRE

NISDPTSPLRTREVYTILSDLCKKCDPTEVELDNQIVTATQSNICDED

SATETCYTYDRNKCYTAVVPLVYGGETKAIVETALTPDACYPDGGGS

GGGGSGGGGSQVQLVQSGAEVKKPGASVKVSCKASGYTFISYTMHWV

RQAPGQGLEWMGYINPRSGYTHYNQKLKDKATLTADKSASTAY

MELSSLRSEDTAVYYCARSAYYDYDGFAYWGQGTLVTVSSGGG

GSGGGGSGGGGSDIQMTQSPSSLSASVGDRVTITCSASSSVSYMN

WYQQKPGKAPKRLIYDTSKLASGVPSRFSGSGSGTDFTLTISSLQP

EDFATYYCQQWSSNPPTFGGGTKLEIK

SEQ ID NO: 69:
ATGAAGAACCATTTGCTTTTCTGGGGAGTCCTGGCGGTTTTTAT

TAAGGCTGTTCATGTGAAAGCCCAAGAAGATGAAAGGATTGTT

CTTGTTGACAACAAATGTAAGTGTGCCCGGATTACTTCCAGGA

TCATCCGTTCTTCCGAAGATCCTAATGAGGACATTGTGGAGAG

AAACATCCGAATTATTGTTCCTCTGAACAACAGGGAGAATATC

TCTGATCCCACCTCACCATTGAGAACCAGATTTGTGTACCATTT

GTCTGACCTCTGTAAAAAATGTGATCCTACAGAAGTGGAGCTG

GATAATCAGATAGTTACTGCTACCCAGAGCAATATCTGTGATG

AAGACAGTGCTACAGAGACCTGCTACACTTATGACAGAAACA

AGTGCTACACAGCTGTGGTCCCACTCGTATATGGTGGTGAGAC

CAAAATGGTGGAAACAGCCTTAACCCCAGATGCCTGCTATCCT

GACGGAGGAGGAGGATCCGGTGGTGGTGGTTCTGGCGGAGGT

GGATCCCAGGTGCAGCTGGTGCAGTCCGGCGCCGAAGTGAAG

AAGCCTGGCGCCAGCGTGAAGGTGAGCTGCAAGGCTTCCGGCT

ACACCTTCATCTCCTACACCATGCACTGGGTGAGGCAAGCTCC

TGGCCAGGGCCTGGAGTGGATGGGATACATCAACCCTCGGTCC

GGCTATACCCACTACAATCAGAAGCTGAAGGACAAGGCCACC

CTGACCGCTGACAAGTCCGCCTCCACCGCTTACATGGAGCTGT

CCTCCCTGAGGTCCGAGGACACCGCCGTGTACTACTGTGCCAG

GTCCGCCTACTACGACTACGACGGATTCGCTTACTGGGGCCAG

GGCACCCTGGTGACAGTGAGCTCCGGAGGAGGAGGCAGCGGT

GGTGGCGGAAGCGGTGGAGGTGGCAGCGATATCCAGATGACC

CAGAGCCCTTCCAGCCTGTCCGCTTCCGTGGGCGACAGGGTGA

CCATCACCTGCAGCGCTTCCTCCTCCGTGTCCTACATGAACTGG

TACCAGCAGAAGCCTGGCAAGGCCCCAAGAGGCTGATCTAC

GACACCTCCAAGCTGGCCTCCGGAGTGCCTTCCAGGTTCAGCG

GCTCCGGCTCCGGAACCGACTTCACCCTGACCATTAGCTCCCT

GCAGCCCGAGGACTTCGCCACCTACTACTGCCAGCAGTGGTCC

-continued
AGCAACCCTCCCACCTTCGGAGGCGGCACAAAGCTGGAGATCA

AGTGA

The mature constructs each have a molecular weight of about 45 kD and can bind to soluble epsilon chain of CD3 (Sino Biological), or T-cells (data not shown).

The DNA constructs corresponding to the various anti-HBsAg heavy and light chains as well as those corresponding to either the wild-type (wt) J-chain, V15J or J15V J-chain sequences were co-transfected into HEK293 cells, and proteins were expressed and purified according to standard methods. See, e.g., PCT Publication No. WO 2015/153912, which is incorporated herein by reference in its entirety. HEK293 cells transfected with IgG or IgM+J versions of HBV19, HBV23, and HBV24 antibodies produced sufficient protein to allow purification by standard methods.

Agarose-Acrylamide Hybrid Gel. IgM Constructs were separated by non-reducing SDS-PAGE adapted from a previously described method (Chugai Seiyaki Kabushiki Kaisha, 2010, Pub. No.: US 2010/0172899 A1). Briefly, the hybrid gel was mixed with 40% Acrylamide/Bis-Acrylamide, 37.5:1 (Sigma-Aldrich) and Ultrapure Agarose (Invitrogen) to final concentrations of 3.6% and 0.5%, respectively, in 0.375 M Tris Buffer, pH 8.8 and 15% glycerol. The resulting mixture was heated to 50° C. and polymerization was initiated with the addition of 0.08% TEMED and 0.08% of ammonium persulfate. The resulting solution was poured between two plates and the acrylamide was allowed to polymerize at 37° C. for 1 hour and then left at room temperature for 30 min to ensure complete polymerization. Protein samples were loaded into the resulting hybrid gel and the gel was run in Tris-Acetate SDS Running Buffer (Novex) for 800 Vh. The gel was then fixed in 40% methanol, 10% acetic for 10 minutes, stained using a Colloidal Blue Staining Kit (Novex) for at least 3 hours and subsequently de-stained in water.

Non-Reducing SDS-Native-PAGE. Protein samples were loaded into a NativePAGE 3-12% Bis-Tris gel (Novex). Tris-Acetate SDS Running Buffer (Novex) was added and the gel was run at 40V for 15 min and then at 90V for 2 hours. The gel was then fixed in 40% methanol, 10% acetic acid for 10 minutes, stained using a Colloidal Blue Staining Kit (Novex) for at least 3 hours and subsequently de-stained in water.

Figure 2A:
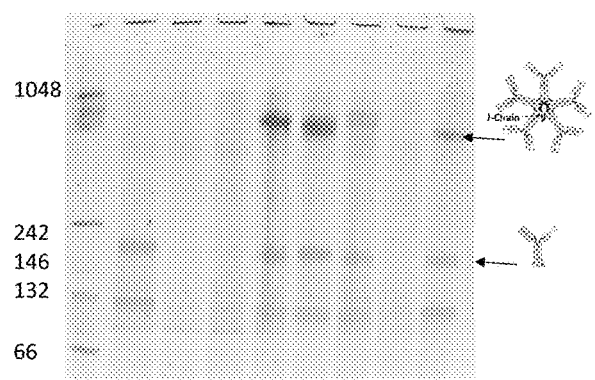
FIG. 2A: SDS polyacrylamide gel showing expression products from various HBV24 IgM constructs.
Figure 2B:
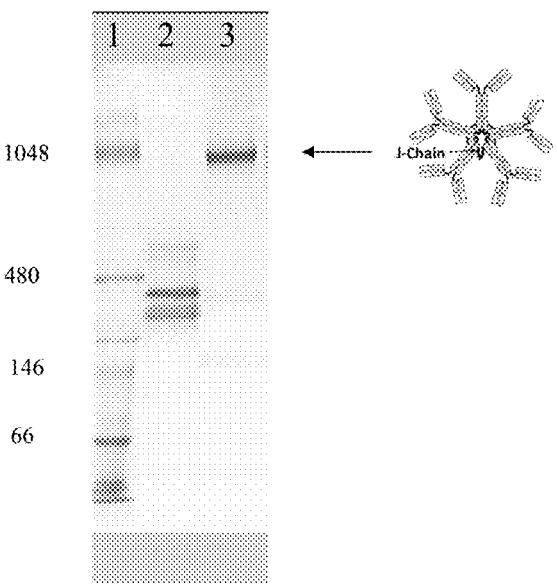
FIG. 2B: SDS polyacrylamide gel showing expression products from HBV23 IgG and IgM constructs.

Expression and assembly of HBV24, as measured by non-reducing SDS native-PAGE is shown in FIG. 2A. Expression and assembly of HBV23 is shown in FIG. 2B. Expression and assembly of HBV19 is shown in FIG. 2C. The heavy and light chains of each IgG expressed well and assembled into IgG antibodies (HBV24, not shown; HBV23, FIG. 2B, Lane 2; HBV19, FIG. 2C, Lane 2).

The heavy and light chains of HBV24M expressed well, but when co-expressed with a human J chain, did not properly assemble into IgM pentamers (FIG. 2A, "Hu/Hu"). On the other hand, the light chain comprising SEQ ID NO: 59, when combined with a chimeric HBV24 with a murine IgM heavy chain constant region, did assemble properly (FIG. 2A, "Ch/Hu").

An IgM heavy chain variable region related to SEQ ID NO: 5 was constructed via site-directed mutagenesis of certain amino acids, resulting in a heavy chain variable region comprising the amino acid sequence SEQ ID NO: 62. SEQ ID 62 was cloned into the appropriate vector according the method described above to encode the IgM heavy chain comprising the amino acid sequence SEQ ID NO: 63. This vector was co-transfected in to HEK293 cells a vector comprising the kappa light chain comprising the amino acid sequence SEQ ID NO: 59 and a vector encoding the human J-chain (SEQ ID NO: 54) or a vector encoding the modified J-chain V15J (SEQ ID NO: 68), and expression was permitted, producing the IgM molecules HBV24M2J and HBV24M2V15J. Both expression products properly assembled into a pentameric IgM molecules. The bispecific binding molecule HBV24M2V15J is shown in FIG. 2A ("M2/Hu").

Example 4: Binding Assays

HBV24M2V15J and HBV23MJ were evaluated for binding to the full-length HBsAg-L (preS1, preS2, and S) by an ELISA assay. For HBV24M2V15J, binding was compared with the humanized IgG antibody specific for pre-S1 antigen provided in U.S. Pat. No. 8,420,353, and for HBV23MJ binding was compared with the human IgG antibody provided in Cerino et al. (2015) PLOS one 10(4):e0125704. doi: 10.1371.

The assays were carried out by the following method. For HBV24, 96-well polystyrene MaxiSorp ELISA plates (Nunc) were coated with 1 µg/mL HBsAg-L antigen (Beacle, BCL-AG-001) in 100 µL coating buffer (100 mM bicarbonate, pH 9.5) overnight at 4° C. For HBV23, plates were coated with HBsAg (Prospec HBS-872). Plates were then washed with 0.05% PBS-Tween and blocked with 2% BSA-PBS. After blocking, 100 µL of the serial diluted samples (purified protein or cell culture supernatant) were added to the wells and incubated at room temperature for 1 hour. The plates were then washed and incubated with HRP conjugated mouse anti-human kappa antibody (Southern Biotech, 9230-05. 1:6000 diluted in 2% BSA-PBS) for the HBV24 antibodies, and with HRP conjugated mouse anti-human Lambda (Southern Biotech, Cat 9180-05. 1:6000 diluted in 2% BSA-PBS) for the HBV23 antibodies, for 1 hour. After 5 final washes using 0.05% PBS-Tween, 100 µL TMB substrate (BD Biosciences, 555214) was added to each well and incubated in dark for 15 min. The reaction was then stopped by adding 50 µL of 2N HCl per well. A450 data was then collected and analyzed with GraphPad Prism using a 4-parameter logistic model.

Figure 3A:
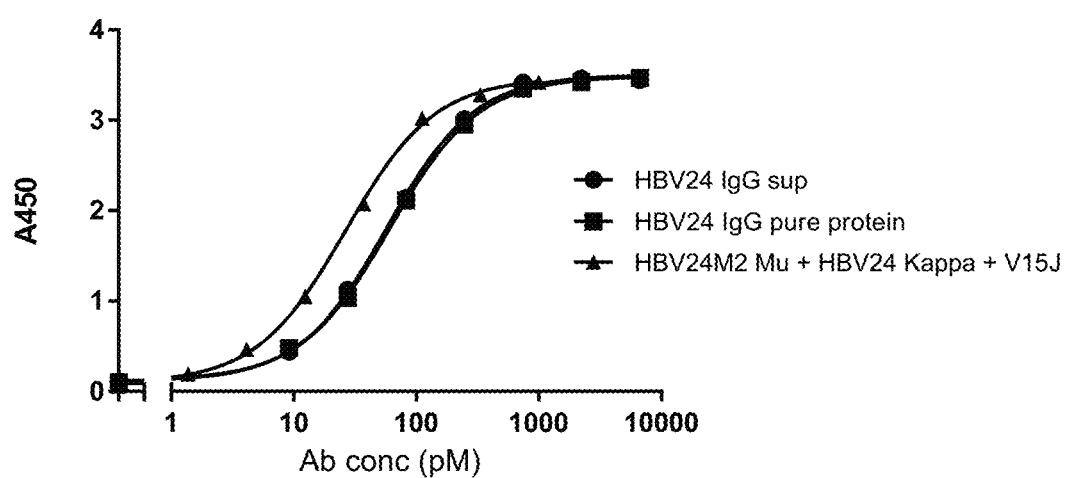
FIG. 3A: ELISA results showing binding of purified HBV24M2V15J (triangles), purified HBV24G (squares), and HBV24G supernatant (circles) to HBsAg-L.

The results for HBV24 are shown in FIG. 3A, comparing IgM vs. IgG by molar concentrations. HBV24M2V15J exhibited more effective binding than the IgG counterpart (HBV24G), exhibiting an EC50 of 26 pM vs 57 pM for the IgG supernatant and 61 pM for the purified IgG.

Figure 3B:
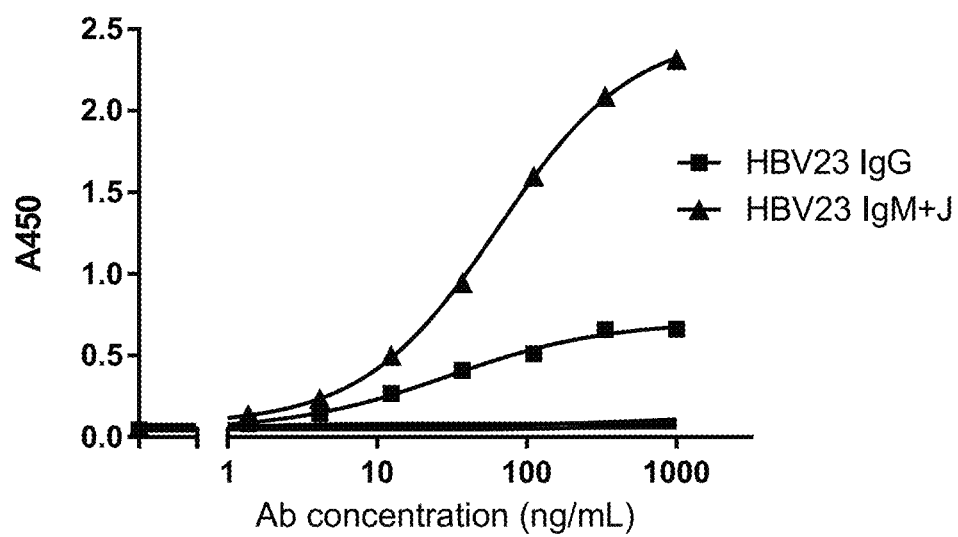
FIG. 3B: ELISA results showing binding of purified HBV23MJ (triangles), purified HBV24G (squares) to HBsAg-L.

The results for HBV23 are shown in FIG. 3B, comparing IgM vs. IgG by weight concentrations. HBV23MJ exhibited more effective binding than the IgG counterpart (HBV23G), exhibiting an EC50 of 64 ng/ml vs 30 ng/ml for the IgG. The capacity of HBV23 MJ binding, as measured by maximum A450, was also much higher than for HBV23G.

HBV24M2V15J, HBV24G, HBV23MJ, and HBV23G were further evaluated for binding to PLC cells, a hepatocellular carcinoma cell line that expresses HBsAg on the cell surface, by the following method.

Alexander hepatoma cells (PLC/PRF/5; ATCC CRL-8024) were cultured in DMEM (Gibco, cat #11965-084) with 10% HI FBS (Gibco, cat #10082-147), and cells were replenished with fresh media the day before staining. On the day of staining, the cells were dislodged using Cell Dissociation Buffer (Gibco, cat #131510-14). After aspirating off all the media, the cells were rinsed with 10 mL of PBS without calcium or magnesium. After aspirating off the PBS, the cells were incubated with 10 ml of Cell Dissociation Buffer for 20~30 min at 37° C. The cells were then dislodged by tapping the flask to create a single cell suspension. Cell Dissociation Buffer was neutralized by adding an equal amount of media, and live cell counts were determined using Trypan Blue exclusion on a cell counter (BioRad TC20). The density of the cells was adjusted to 1.5×10e4 cells per 60 µL of FACS 2% FBS buffer (BD Pharmingen, cat #554656), and 60 were added to "v" bottom 96 well plates. All antibodies were tested at final concentrations of 30 µg/mL, 10 µg/mL, 3 µg/mL, and 1 µg/mL; and 50 µL of the each antibody was added to the respective wells. The plates were then incubated for 30 min at 4° C. After washing the cells with 150 µL of FACS 2% FBS buffer, the plates were centrifuged (Sorvall Legend XIR centrifuge) at 1200 rpm for 5 min. and supernatants were gently aspirated without disturbing the cell pellets. Antibody binding was detected by incubating the cells with the appropriate AlexaFluor-647-labeled secondary antibody, anti-human kappa light chain (BioLegend, cat #316514) or AF647 anti-human lambda light chain (BioLegend, cat #316614), at 4° C. for 30 min. The wash step was repeated as above and the cells were resuspended in 60 µL of FACS 2% FBS with 1:100 7_AAD (BD Pharm, cat #51-68981E). One thousand events were acquired for each sample on a FACSCalibur™ (Becton Dickinson) and the data analysis was done in FlowJo, from FlowJo LLC. For each study, antibody binding was compered to unstained cells and cells stained with the appropriate human isotype control antibody.

Figure 4:
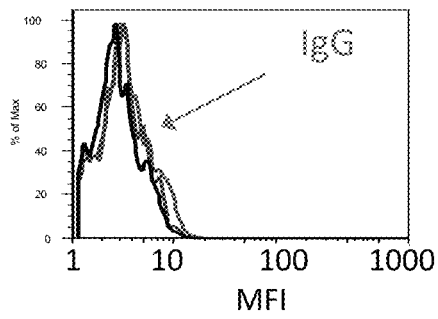
FIG. 4: FACS analysis of HBV antibody binding to PLC hepatocarcinoma cells. Top Row: Anti-S antibody (HBV23 anti-HBsAg), IgG and IgM+human J-chain; bottom row: Anti preS1 antibody (HBV24G and HBV24M2V15J), IgG and IgM+V15J. The unlabeled histograms in each panel represent unstained PLC cells and PLC cells stained with the appropriate human antibody isotype controls (IgG or IgM).
Figure 4:
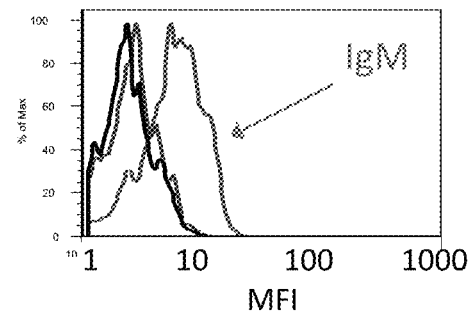
Figure 4:
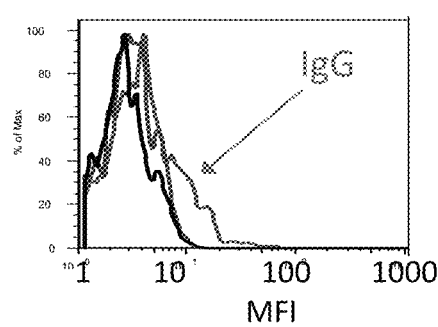
Figure 4:
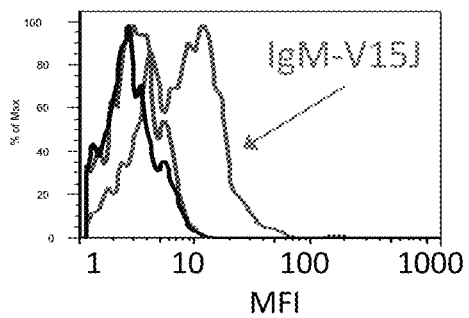

Binding of HBV24G and HBV23G could not be detected by FACS analysis. On the other hand, HBV23MJ and the bispecific HBV24M2V15J showed detectable binding (FIG. 4).

Example 5: Screening for Antibodies that Bind Preferentially to Infectious Virions and/or HBV-Infected Cells In this example, a library is screened for binding molecules that bind to cells infected by a virus of interest, or infectious versions of that virus to a greater extent, e.g., affinity, avidity, or other characteristics. A binding molecule library, e.g., an antibody library (phage/hybridoma/etc) is created, e.g., a library of VH and VL regions derived from B cells of a virus-infected mammal, e.g., an HBV-infected mammal. The library is then contacted with virus-infected cells, e.g., HBV-infected cells, e.g., a Hepatocellular carcinoma (HCC) cell line, or infectious viral particles, e.g., HBV particles, on a solid support, e.g., adherent to 96-well plate or beads to enrich those antibodies that bind to infected cells (will include all such antibodies, whether or not they also bind to non-infectious particles). Antibodies that bind to the infected cells are harvested and amplified. The recovered antibodies are then put in contact with non-infectious viral particles, e.g., HBV subviral particles, and/or to non-infected cells of the same type as the earlier-used virus-infected cells, where the non-infectious particles and/or cells are attached to a solid support such as a plate, beads, column, etc. Antibodies that do not bind to the non-infectious viral particles or non-infected cells are recovered and amplified. This step is repeated one or more times to enrich for those antibodies that preferentially bind to virus-infected cells or infectious virus particles. The enriched/selectively depleted library is again recovered and amplified. Finally, antibodies of interest are recovered, clone purified, and further characterized.

Example 6: Virus Neutralization Assays

In vitro HBV virus neutralization assays can be conducted using a variety of standard techniques, such as those described by Maeng et al., *Virology* 270:9-16, 2000. Briefly, human hepatocytes (prepared by enzymatic dissociation of non-cancerous liver fragments) are seeded at a density of $10^6$ cells per well containing 2 ml of normal growth medium and are infected 3 days later with HBV particles (about $3\times10^7$ viral genomic equivalents).

For the neutralization assay, the virus particles are pre-incubated with various concentrations of the antibody (as well as appropriate controls) at room temperature for 1 h and inoculated onto the cultured hepatocytes. The hepatocytes are covered with 1 ml of the serum-free culture medium containing 4% polyethylene glycol (PEG). The infected cells are washed with the growth medium and further incubated for 17 days, with the medium renewed every 2 days.

On Day 17 post-infection, an aliquot of the culture medium is removed and diluted 10-fold, and the concentration of an HBV antigen (e.g., HBsAg) is determined using an appropriate assay kit, e.g., for HBsAg, a radioimmunoassay kit (Abbott Laboratories, Chicago, Ill.).

Alternatively, HBV virus neutralization studies can be conducted as described by Kim (FEBS Letters 2015; 589, 193-200). Briefly, HepaRG cells (e.g., ThermoFisher HPRGC10) are seeded at a density of $6\times10^4$ cells per well (containing 100 µL of culture medium) and are cultured for 6 days. Viral particles (5 µL) are then preincubated with 5 µL of antibody at various concentrations at room temperature for 30 min and then incubated with the cultured HepaRG cells for 24 h in the absence or presence of 4% PEG 8000. The infected cells are washed with the medium and further incubated for 10 days, with the medium changed every 2 days. On day 10 post infection, the culture supernatant are diluted in order to remain in the quantitative range of the assay and the HBsAg concentration is determined with an ELISA kit (Bio-Rad).

Example 7: In Vivo Models

Dimeric, pentameric, or hexameric binding molecules provided herein can be tested in vivo in mouse models including, without limitation, uPA/RAG-2 mouse (Dandri Hepatology 2001; 33 (4): 981-988), immunodeficient urokinase-type plasminogen activator (uPA)/recombinant activation gene-2 (RAG-2) mice. The mice can be repopulated with human hepatocytes and infected with HBV, to test the binding molecules for efficacy in vivo. The trimera mouse model (Ilan Hepatology 1999; 29: 553-562) involves lethally irradiated mice, radioprotected with SCID mouse bone marrow cells. The Fah−/−Rag2−/−Il2rg−/− model (Grompe Nat Biotech 2007; 25 (8): 903-910; Verma PNAS 2007; 104 (51):20507-20511) involves immunodeficient, fumaryl acetoacetate hydrolase-deficient (fah(−/−)) mice with a regulatable system for repopulating the liver with human hepatocytes. The TK-NOG based humanized mouse model (Kosaka Biochem Biophys Res Commun. 2013 Nov. 8; 441(1):230-5) involves super immunodeficient NOG mouse with transgenic expression of thymidine kinase under control of liver-restricted albumin promoter. The MUP-uPA/SCID/Bg model (Tesfave PLoS ONE 2013; 8(10):e77298) involves mice carrying the uPA gene driven by the major urinary protein promoter on a SCID/Beige background. Dimeric, pentameric, or hexameric binding molecules can be tested in vivo in non-human primates. The As/HSG-hu HSC/Hep mouse model (Bility PLoS ONE 2014; 10(3): e1004032) involves mice repopulated with both human immune and liver cells and supports persistent HBV infection.

Example 8: Complement Dependent Cytotoxicity of HBV Antibodies

Antibodies of the IgM phenotype are particularly well-suited to use the efficient engagement of complement protein C1q to affect complement dependent cytotoxicity (CDC) activity on target cells. To measure CDC, hepatocellular carcinoma cells expressing HBsAg (e.g. Alexander hepatoma cells (PLC/PRF/5; ATCC CRL-8024)) or recombinant cells expressing HBsAg-L are used. The target cells are washed and resuspended in CDC assay medium (RPMI 1640, 10% heat-inactivated FBS) at a density of $1.0\times10^6$ cells/mL and 10 µL/well is added to a Nunc 384-well tissue culture-treated white polystyrene plate. Serial 3-fold dilutions of test antibodies are prepared in assay medium, 10 µL/well is added to the assay plate, and the plate is incubated for 2 hr at 37° C. in a 5% $CO_2$ incubator to allow opsonization to occur. Normal human serum complement (Quidel) is diluted to 30% in assay medium, and 10 µL/well is added to the assay plate. The plate is incubated for 4 hr at 37° C. in a 5% $CO_2$ incubator. Cell Titer-Glo reagent (Promega) is thawed for use and 15 µL/well is added to the assay plate. The plate is gently mixed for 2 min on a plate shaker to lyse the cells and then for another 10 min at room temperature before measuring luminescence on an EnVision plate reader (Perkin-Elmer). After subtracting background signal, percent viability is plotted against antibody concentration and EC50 values are determined using GraphPad Prism.

Example 9: T-Cell Activation by HBVXCD3 Bispecific Antibodies

To demonstrate whether a bispecific anti-HBsAg/anti-CD3 antibody can activate T cells upon binding to the HBsAg target the following assay is performed. Engineered Jurkat T cells (Promega CS176403) and either hepatocellular carcinoma cells expressing HBsAg (e.g., Alexander hepatoma cells (PLC/PRF/5; ATCC CRL-8024)) or recombinant cells expressing HBsAg-L are cultured in RPMI (Invitrogen) supplemented with 10% Fetal Bovine Serum (Invitrogen). Serial dilutions of purified bispecific and monospecific anti-HBV antibodies are incubated with HBsAg-expressing cells in 20 µL in a white 384 well assay plate for 2 h at 37° C. with 5% $CO_2$. The engineered Jurkat cells (25000) are added to the mixture to a final volume of 40 µL. The mixture is incubated for 5 h at 37° C. with 5% $CO_2$. The cell mixtures are then mixed with 20 µL lysis buffer containing luciferin (Promega, Cell Titer Glo) to measure luciferase reporter activity. Light output is measured by EnVision plate reader. EC50 is determined by 4 parameter curve fit using Prism software.

Example 10: T-Cell Directed B-Cell Killing—LDH Release Assay

In order to demonstrate whether bispecific HBV×CD3 IgM binding molecules can kill target cells in the presence of CD8+ T-cell acute lymphoblastic leukemia (TALL) cells, co-culture experiments can be performed. HBsAg-expressing cells (about $6\times10^3$ cells), e.g., hepatocellular carcinoma cells such as Alexander hepatoma cells (PLC/PRF/5; ATCC CRL-8024) or recombinant cells expressing HBsAg-L, are co-cultured with 3×10⁴ TALL cells (ATCC CRL-11386) in the presence of different concentrations of test compounds in 45 μL total volume of RPMI 1640 media supplemented with 10% heat-inactivated FBS per well on a 384-well black tissue culture plate. After 24 hours of incubation at 37° C. in a 5% $CO_2$ incubator, 15 μL of CytoTox-ONE substrate reagent (Promega, G7891) is added to each well to measure the level of LDH released from dead cells. The plates are shaken briefly to mix the reagents, and then incubated at room temperature for 90 min before measuring fluorescence signal (485 nm for excitation and 615 nm for emission) on an EnVision plate reader (Perkin-Elmer). The data is then analyzed with GraphPad Prism to determine the $EC_{50}$.

The breadth and scope of the disclosure should not be limited by any of the above-described exemplary embodiments, but should be defined in accordance with the following claims and their equivalents.

What is claimed is:

1. A multimeric binding molecule comprising at least two IgA bivalent binding units, or variants or fragments thereof and a J-chain or fragment or variant thereof;
   wherein the J-chain or fragment or variant thereof is modified to comprise a heterologous polypeptide directly or indirectly fused to the J-chain or fragment or variant thereof,
   wherein each IgA binding unit comprises at least two IgA antibody heavy chain constant regions or fragments thereof, each associated with an antigen binding domain;
   wherein the antigen binding domains specifically bind to a hepatitis B virus (HBV) antigen expressed on the surface of infectious viral particles, on the surface of HBV infected cells, or a combination thereof, and
   wherein the binding molecule is more potent than a reference IgG antibody comprising the antigen binding domain that specifically binds to the HBV antigen.

2. The binding molecule of claim 1, further comprising a secretory component, or fragment or variant thereof.

3. The binding molecule of claim 1, wherein the IgA heavy chain constant regions or fragments thereof each comprise a Cα3-tp domain, and further comprise a Cα1 domain, Cα2 domain, or Cα1 domain and a Cα2 domain.

4. The binding molecule of claim 1, wherein the IgA heavy chain constant regions are human IgA constant regions.

5. The binding molecule of claim 1, wherein each binding unit comprises two IgA heavy chains each comprising a heavy chain variable region (VH) situated amino terminal to the IgA constant region or fragment thereof, and two immunoglobulin light chains each comprising a light chain variable region (VL) situated amino terminal to an immunoglobulin light chain constant region, and wherein each VH comprises an HCDR1, an HCDR2, and an HCDR3 region and each VL comprises an LCDR1, an LCDR2, and an LCDR3 region.

6. The binding molecule of claim 1, wherein J-chain or fragment or variant thereof comprises the amino acid sequence SEQ ID NO: 54 or a functional fragment or variant thereof.

7. The binding molecule of claim 1, wherein the heterologous polypeptide is fused to the N-terminus of the J-chain or fragment or variant thereof, the C-terminus of the J-chain or fragment or variant thereof, or to both the N-terminus and C-terminus of the J-chain or fragment or variant thereof.

8. The binding molecule of claim 7, wherein the heterologous polypeptide is fused to the J-chain or fragment or variant thereof via a peptide linker that comprises at least 5 amino acids, but no more than 25 amino acids.

9. The binding molecule of claim 7, wherein the heterologous polypeptide comprises a binding domain.

10. The binding molecule of claim 9, wherein the binding domain of the heterologous polypeptide is an antibody or antigen-binding fragment thereof.

11. The binding molecule of claim 10, wherein the antigen-binding fragment comprises an Fab fragment, an Fab' fragment, an F(ab')$_2$ fragment, an Fd fragment, an Fv fragment, a single-chain Fv (scFv) fragment, a disulfide-linked Fv (sdFv) fragment, or any combination thereof.

12. The binding molecule of claim 11, wherein the antigen-binding fragment is a scFv fragment that specifically binds to $CD3_\varepsilon$.

13. The binding molecule of claim 1, wherein the HBV antigen is a hepatitis B surface antigen (HBsAg), a precore antigen, a core antigen, an X-antigen, or any combination thereof.

14. The binding molecule of claim 13, wherein the HBV antigen is HBsAg, and wherein HBsAg is comprised of: the S region (S); the pre-S2 region and the S region; the pre-S1 region, the pre-S2 region, and the S region; or fragments thereof.

15. The binding molecule of claim 5, comprising the HCDR1, HCDR2, and HCDR3 regions, or the HCDR1, HCDR2, and HCDR3 regions containing one or two single amino acid substitutions, and the LCDR1, LCDR2, and LCDR3 regions, or the LCDR1, LCDR2, and LCDR3 regions containing one or two single amino acid substitutions, of the VH and VL amino acid sequences SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76, respectively.

16. The binding molecule of claim 1, wherein the antigen binding domains comprise an antibody heavy chain variable region (VH) and an antibody light chain variable region (VL), wherein the VH and VL comprise, respectively, amino acid sequences that are at least 80%, at least 85%, at least 90%, at least 95% or 100% identical to SEQ ID NO: 1 and SEQ ID NO: 3, SEQ ID NO: 2 and SEQ ID NO: 3, SEQ ID NO: 4 and SEQ ID NO: 3, SEQ ID NO: 5 and SEQ ID NO: 6, SEQ ID NO: 7 and SEQ ID NO: 8, SEQ ID NO: 7 and SEQ ID NO: 9, SEQ ID NO: 10 and SEQ ID NO: 11, SEQ ID NO: 14 and SEQ ID NO: 15, SEQ ID NO: 16 and SEQ ID NO: 21, SEQ ID NO: 17 and SEQ ID NO: 22, SEQ ID NO: 18 and SEQ ID NO: 23, SEQ ID NO: 19 and SEQ ID NO: 24, SEQ ID NO: 20 and SEQ ID NO: 25, SEQ ID NO: 26 and SEQ ID NO: 27, SEQ ID NO: 26 and SEQ ID NO: 28, SEQ ID NO: 26 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 34 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 62 and SEQ ID NO: 6, SEQ ID NO: 73 and SEQ ID NO: 74, or SEQ ID NO: 75 and SEQ ID NO: 76.

17. A composition comprising the binding molecule of claim 1.

18. A polynucleotide comprising a nucleic acid sequence that encodes a polypeptide subunit of the binding molecule of claim 1.

19. A method of treating a disease or condition caused by or exacerbated by hepatitis B virus (HBV) infection in a patient, comprising administering to a patient infected with HBV or susceptible to HBV infection the binding molecule of claim 1 wherein the binding molecule is more potent than a reference IgG antibody comprising the antigen binding domain that specifically binds to the HBV antigen.

* * * * *

SEQUENCE LISTING

```
<160> NUMBER OF SEQ ID NOS: 86

<210> SEQ ID NO 1
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Ile
            35                  40                  45

Gly Arg Ile Tyr Pro Gly Asp Gly Asp Thr Asn Tyr Ala Gln Lys Phe
        50                  55                  60

Gln Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Tyr Asp Glu Ala Tyr Trp Gly Gln Gly Thr Leu Val Thr
                100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Tyr Ala Gln Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Glu Tyr Asp Glu Ala Tyr Trp Gly Gln Gly Thr Leu Val Thr
                100                 105                 110

Val Ser Ser
        115

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Lys Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

Arg

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Pro Glu Leu Ala Lys Val Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Ala Gln Lys Phe
50                  55                  60

Gln Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Tyr Asp Glu Ala Tyr Trp Gly Gln Gly Thr Leu Val Thr
                100                 105                 110

Val Ser Ser
        115
```

```
<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Ala Pro Gly Ala
1               5                   10                  15

Ser Val Lys Val Ser Cys Lys Ala Ser Gly Tyr Thr Phe Thr Ser Ala
            20                  25                  30

Trp Met Asn Trp Val Arg Gln Ala Pro Gly Gln Gly Leu Glu Trp Met
        35                  40                  45

Gly Arg Ile Tyr Pro Ser Gly Gly Ser Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Arg Val Ala Arg Trp Gly Gln Gly Thr Leu Val Thr
            100                 105                 110

Val Ser Ala
        115

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Pro
        35                  40                  45

Pro Gln Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

Glu Val Gln Leu Val Glu Ser Gly Gly Asp Leu Val Lys Pro Gly Gly
1               5                   10                  15

Ser Leu Arg Leu Ser Cys Ala Ala Ser Gly Leu Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ser Asp Gly Gly Thr Thr Asp Tyr Ala Ala
    50                  55                  60

Pro Val Glu Gly Arg Phe Ser Ile Ser Arg Asp Asp Ser Lys Asp Thr
65                  70                  75                  80

Leu Tyr Leu Gln Met Asn Ser Leu Lys Thr Glu Asp Thr Ala Val Tyr
                85                  90                  95

Tyr Cys Ala Ser Arg Leu Val Ala Glu Gly Gly Phe Asp Ser Trp Gly
            100                 105                 110

Gln Gly Thr Leu Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Tyr Ser Phe Gly Gln Gly Thr Lys Leu Glu Ile
            100                 105                 110

Lys

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro Tyr Ser Phe Gly Gln Gly Thr Lys Leu Glu Ile
            100                 105                 110
Lys
```

<210> SEQ ID NO 10
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Val Glu Ser Gly Gly Gly Val Val Arg Pro Gly Arg
1               5                   10                  15
Ser Leu Arg Leu Ser Cys Ala Ala Ser Gly Phe Ala Phe Ser Asp Tyr
            20                  25                  30
Ser Ile Asn Trp Val Arg Gln Ala Pro Gly Lys Gly Leu Glu Trp Val
        35                  40                  45
Ala Ile Ile Ser Tyr Asp Gly Arg Ile Thr Tyr Tyr Arg Asp Ser Val
    50                  55                  60
Lys Gly Arg Phe Thr Ile Ser Arg Asp Asp Ser Lys Asn Thr Leu Tyr
65                  70                  75                  80
Leu Gln Met Asn Ser Leu Arg Thr Glu Asp Thr Ala Val Tyr Tyr Cys
                85                  90                  95
Ala Arg Gln Tyr Tyr Asp Phe Trp Ser Gly Ser Ser Val Gly Arg Asn
            100                 105                 110
Tyr Asp Gly Met Asp Val Trp Gly Leu Gly Thr Thr Val Thr Val Ser
        115                 120                 125
Ser
```

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Asp Ile Val Met Thr Gln Ser Pro Leu Ser Leu Ser Val Thr Pro Gly
1               5                   10                  15
Glu Pro Ala Ser Ile Ser Cys Arg Ser Ser Gln Ser Leu Leu His Arg
            20                  25                  30
Ser Gly Asn Asn Tyr Leu Asp Trp Tyr Leu Gln Lys Pro Gly His Ser
        35                  40                  45
Pro Gln Leu Leu Ile Tyr Val Gly Ser Asn Arg Ala Ser Gly Val Pro
    50                  55                  60
Asp Arg Phe Ser Gly Ser Gly Ser Gly Thr Glu Tyr Thr Leu Lys Ile
65                  70                  75                  80
```

Ser Arg Val Glu Ala Glu Asp Val Gly Val Tyr Tyr Cys Met Gln Ala
            85                  90                  95

Leu Gln Thr Pro Arg Thr Phe Gly Gln Gly Thr Lys Leu Glu Ile Lys
            100                 105                 110

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Trp Val Asp Gln Thr Pro Arg Thr Ala Thr Lys Glu Thr Gly Glu
1               5                   10                  15

Ser Leu Thr Ile Asn Cys Val Leu Arg Asp Thr Ser Cys Ala Phe Ser
            20                  25                  30

Ser Thr Gly Trp Tyr Arg Thr Lys Leu Gly Ser Thr Asn Glu Gln Ser
        35                  40                  45

Ile Ser Thr Gly Gly Arg Tyr Val Glu Thr Val Asn Lys Thr Ser Lys
    50                  55                  60

Ser Ile Ser Leu Arg Ile Ser Asp Leu Arg Val Glu Asp Ser Gly Thr
65                  70                  75                  80

Tyr Lys Cys Gln Val Tyr Phe Thr Pro Val Trp Asp Gly Ser Cys Phe
                85                  90                  95

Gly Ile Leu Gly Arg Thr Lys Lys Gly Ala Gly Thr Ala Leu Thr Val
            100                 105                 110

Lys

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Trp Val Asp Gln Thr Pro Arg Thr Ala Thr Lys Glu Thr Gly Glu
1               5                   10                  15

Ser Leu Thr Ile Asn Cys Val Leu Arg Asp Thr Ser Cys Ala Phe Ser
            20                  25                  30

Gly Thr Gly Trp Tyr Arg Thr Lys Leu Gly Ser Thr Asn Glu Gln Ser
        35                  40                  45

Ile Ser Ile Gly Gly Arg Tyr Val Glu Thr Val Ser Lys Gly Ser Lys
    50                  55                  60

Ser Ile Ser Leu Arg Ile Ser Asp Leu Arg Val Glu Asp Ser Gly Thr
65                  70                  75                  80

Tyr Lys Cys Gln Val Tyr Phe Thr Pro Val Trp Asp Gly Ser Cys Phe
                85                  90                  95

Gly Ile Leu Gly Arg Thr Lys Lys Gly Ala Gly Thr Ala Leu Thr Val
            100                 105                 110

Lys

<210> SEQ ID NO 14
<211> LENGTH: 122
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Arg Val Ser Cys Glu Val Ser Gly Phe Thr Phe Ser Asn Asn
            20                  25                  30

Trp Met His Trp Val Arg Gln Ala Pro Gly Lys Gly Pro Val Trp Val
        35                  40                  45

Ser Arg Ile Ser Thr Asp Gly Met Ser Thr Ser Tyr Ala Glu Phe Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Arg Asp Glu Asp Thr Ala Val Tyr Tyr Cys
                85                  90                  95

Val Arg Gly Ser Thr Tyr Tyr Phe Gly Ser Gly Ser Leu Asn Phe Trp
            100                 105                 110

Gly Gln Gly Thr Thr Val Ile Val Ser Ser
        115                 120

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Ala Leu Thr Gln Pro Arg Ser Val Ser Gly Ser Pro Gly Gln
1               5                   10                  15

Ser Val Thr Ile Ser Cys Thr Gly Thr Asn Ser Asp Ile Gly Asn Tyr
            20                  25                  30

Asp Tyr Val Ser Trp Tyr Gln Gln His Pro Gly Lys Ala Pro Arg Leu
        35                  40                  45

Ile Ile Tyr Asp Val Ser Glu Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Phe Cys Ser Ser Tyr Ala Gly Thr
                85                  90                  95

Phe Thr Tyr Val Val Phe Gly Gly Gly Thr Lys Leu Thr Val Leu
            100                 105                 110

<210> SEQ ID NO 16
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Lys Leu Leu Glu Ser Gly Gly Gly Leu Val Lys Pro Gly Gly
1               5                   10                  15

Ser Leu Arg Leu Ser Cys Ser Ala Ser Gly Phe Ser Leu Thr Lys Tyr
            20                  25                  30
```

```
Lys Met Thr Trp Val Arg Gln Ala Pro Gly Lys Gly Leu Glu Trp Val
            35                  40                  45

Ser Ser Ile Ser Ser Thr Ser Arg Asp Ile Asp Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Ser Ser Leu Arg Val Asp Asp Thr Ala Val Tyr Tyr Cys
                 85                  90                  95

Thr Arg Asp Gly Trp Leu Trp Gly Trp Asp Val Arg Ser Asn Tyr Tyr
             100                 105                 110

Tyr Asn Ala Leu Asp Val Trp Gly Gln Gly Thr Thr Val Thr Val Ser
         115                 120                 125

Ser
```

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Glu Val Gln Leu Val Glu Ser Gly Gly Gly Leu Val Lys Pro Gly Gly
 1               5                  10                  15

Ser Leu Arg Leu Ser Cys Ser Ala Ser Gly Phe Ser Leu Thr Lys Tyr
             20                  25                  30

Lys Met Thr Trp Val Arg Gln Ala Pro Gly Lys Gly Leu Glu Trp Val
            35                  40                  45

Ser Ser Ile Ser Ser Thr Ser Arg Asp Ile Asp Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Ser Ser Leu Arg Val Asp Asp Thr Ala Val Tyr Tyr Cys
                 85                  90                  95

Thr Arg Asp Gly Trp Leu Trp Gly Trp Asp Val Arg Ser Asn Tyr Tyr
             100                 105                 110

Tyr Asn Ala Leu Asp Val Trp Gly Gln Gly Thr Thr Val Thr Val Ser
         115                 120                 125

Ser
```

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Val Gln Ser Gly Gly Glu Val Lys Lys Pro Gly Ala
 1               5                  10                  15

Leu Met Lys Val Ser Cys Lys Ala Ser Gly Tyr Ile Phe Thr Ser Tyr
             20                  25                  30

Gly Ile Ser Trp Val Arg Gln Ala Pro Gly Gln Gly Leu Glu Trp Ile
            35                  40                  45

Gly Trp Ile Asn Thr Tyr Ser Gly His Thr Asn Tyr Ala Arg Lys Phe
 50                  55                  60
```

```
Arg Gly Arg Val Thr Met Thr Trp Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Val Pro Thr Trp Gly Ile Asp Tyr Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Gly Glu Val Lys Lys Pro Gly Ala
1               5                   10                  15

Leu Met Lys Val Ser Cys Lys Ala Ser Gly Tyr Ile Phe Thr Ser Tyr
            20                  25                  30

Gly Ile Ser Trp Val Arg Gln Ala Pro Gly Gln Gly Leu Glu Trp Ile
        35                  40                  45

Gly Trp Ile Asn Thr Tyr Ser Gly His Thr Asn Tyr Ala Arg Lys Phe
    50                  55                  60

Arg Gly Arg Val Thr Met Thr Trp Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Val Pro Thr Trp Gly Ile Asp Tyr Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Gly Glu Val Lys Lys Pro Gly Ala
1               5                   10                  15

Leu Met Lys Val Ser Cys Lys Ala Ser Gly Tyr Ile Phe Thr Ser Tyr
            20                  25                  30

Gly Ile Ser Trp Val Arg Gln Ala Pro Gly Gln Gly Leu Glu Trp Ile
        35                  40                  45

Gly Trp Ile Asn Thr Tyr Ser Gly His Thr Asn Tyr Ala Arg Lys Phe
    50                  55                  60

Arg Gly Arg Val Thr Met Thr Trp Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95
```

```
Ala Arg Val Pro Thr Trp Gly Ile Asp Tyr Trp Gly Gln Gly Thr Leu
            100                 105                 110

Val Thr Val Ser Ser
        115
```

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Ser
            20                  25                  30

Ile Ala Trp Tyr Gln Gln Lys Pro Gly Lys Ala Pro Lys Leu Leu Leu
        35                  40                  45

Tyr Ser Thr Ser Thr Leu Leu Ser Gly Val Pro Ser Arg Phe Ser Gly
    50                  55                  60

Ser Gly Ser Gly Thr Asp Tyr Thr Leu Thr Ile Thr Asn Leu Gln Pro
65                  70                  75                  80

Glu Asp Phe Ala Thr Tyr Tyr Cys Gln Gln Tyr Phe Val Thr Pro Glu
                85                  90                  95

Thr Phe Gly Gln Gly Thr Lys Val Glu Ile Lys Arg
            100                 105
```

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Ile Val Val Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Ser
            20                  25                  30

Ile Ala Trp Tyr Gln Gln Lys Pro Gly Lys Ala Pro Lys Leu Leu Leu
        35                  40                  45

Tyr Ser Thr Ser Thr Leu Leu Ser Gly Val Pro Ser Arg Phe Ser Gly
    50                  55                  60

Ser Gly Ser Gly Thr Asp Tyr Thr Leu Thr Ile Thr Asn Leu Gln Pro
65                  70                  75                  80

Glu Asp Phe Ala Thr Tyr Tyr Cys Gln Gln Tyr Phe Val Thr Pro Glu
                85                  90                  95

Thr Phe Gly Gln Gly Thr Lys Leu Glu Ile Lys Arg
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ala Gly Leu Thr Gln Pro Pro Ser Val Ser Val Ala Pro Gly Lys
1               5                   10                  15

Thr Ala Arg Ile Thr Cys Gly Gly Asp Asn Ile Gly Arg Lys Ser Val
            20                  25                  30

His Trp Tyr Gln Gln Lys Thr Gly Gln Ala Pro Val Leu Val Val Tyr
        35                  40                  45

Glu Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly
            100                 105

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Leu Thr Gln Ser Pro Pro Ser Leu Ser Ala Ser Val Gly
1               5                   10                  15

Asp Arg Val Thr Ile Thr Cys Gln Ala Ser Gln Asp Ile Asn Asn Asn
            20                  25                  30

Val Asn Trp Phe Gln Gln Glu Pro Gly Lys Ala Pro Arg Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Ser Val Tyr Pro Leu
                85                  90                  95

Thr Phe Gly Gly Gly Thr Lys Val Asp Ile Lys Arg
            100                 105

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Lys Arg Ala Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Ser
            85                  90                  95

Thr Gln Phe Pro Pro Tyr Thr Phe Gly Gln Gly Thr Lys Leu Glu Ile
            100                 105                 110

Lys Arg

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Gly Glu Val Lys Lys Pro Gly Ala
1               5                   10                  15

Leu Met Lys Val Ser Cys Lys Ala Ser Gly Tyr Ile Phe Thr Ser Tyr
            20                  25                  30

Gly Ile Ser Trp Val Arg Gln Ala Pro Gly Gln Gly Leu Glu Trp Ile
        35                  40                  45

Gly Trp Ile Asn Thr Tyr Ser Gly His Thr Asn Tyr Ala Arg Lys Phe
    50                  55                  60

Arg Gly Arg Val Thr Met Thr Trp Asp Thr Ser Thr Ser Thr Ala Tyr
65                  70                  75                  80

Met Glu Leu Ser Ser Leu Arg Ser Asp Asp Thr Ala Val Tyr Tyr Cys
            85                  90                  95

Ala Arg Val Pro Thr Trp Gly Ile Asp Tyr Trp Gly Gln Gly Thr Leu
            100                 105                 110

Val Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Ala Gly Leu Thr Gln Pro Pro Ser Val Ser Val Ala Pro Gly Lys
1               5                   10                  15

Thr Ala Arg Ile Thr Cys Gly Gly Asp Asn Ile Gly Arg Lys Ser Val
            20                  25                  30

His Trp Tyr Gln Gln Lys Thr Gly Gln Ala Pro Val Leu Val Val Tyr
            35                  40                  45

Glu Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
            85                  90                  95

Phe Gly Gly Gly Thr Lys Leu Thr Val Leu Gly
            100                 105

```
<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Leu Thr Gln Ser Pro Pro Ser Leu Ser Ala Ser Val Gly
1               5                   10                  15

Asp Arg Val Thr Ile Thr Cys Gln Ala Ser Gln Asp Ile Asn Asn Asn
            20                  25                  30

Val Asn Trp Phe Gln Gln Glu Pro Gly Lys Ala Pro Arg Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Ser Val Tyr Pro Leu
                85                  90                  95

Thr Phe Gly Gly Gly Thr Lys Val Asp Ile Lys Arg
            100                 105

<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Lys Arg Ala Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Ser
                85                  90                  95

Thr Gln Phe Pro Pro Tyr Thr Phe Gly Gln Gly Thr Lys Leu Glu Ile
            100                 105                 110

Lys Arg

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 30

Gln Val Gln Leu Val Glu Ser Gly Gly Gly Val Val Gln Pro Gly Gly
1               5                   10                  15

Ser Leu Arg Leu Ser Cys Ala Pro Ser Gly Phe Val Phe Arg Ser Tyr
            20                  25                  30

Gly Met His Trp Val Arg Gln Thr Pro Gly Lys Gly Leu Glu Trp Val
        35                  40                  45

Ser Leu Ile Trp His Asp Gly Ser Asn Arg Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Ala Arg Glu Arg Leu Ile Ala Ala Pro Ala Ala Phe Asp Leu Trp Gly
            100                 105                 110

Gln Gly Thr Leu Val Thr Val Ser Ser
        115                 120

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Tyr Val Leu Thr Gln Pro Pro Ser Val Ser Val Ala Pro Gly Lys
1               5                   10                  15

Thr Ala Arg Ile Ser Cys Gly Gly Asn Asn Ile Gly Thr Lys Asn Val
            20                  25                  30

His Trp Tyr Gln Gln Lys Pro Gly Gln Ala Pro Val Leu Val Val Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Tyr Cys Gln Val Trp Asp Ser Val Ser Tyr His
                85                  90                  95

Val Val Phe Gly Gly Gly Thr Thr Leu Thr Val Leu Gly
            100                 105

<210> SEQ ID NO 32
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Gly Gly Gly Val Val Arg Pro Gly Arg
1               5                   10                  15

Ser Leu Arg Leu Ser Cys Ala Ala Ser Gly Phe Ala Phe Ser Asp Tyr
            20                  25                  30

Ser Ile Asn Trp Val Arg Gln Ala Pro Gly Lys Gly Leu Glu Trp Val
        35                  40                  45
```

```
Ala Ile Ile Ser Tyr Asp Gly Arg Ile Thr Tyr Tyr Arg Asp Ser Val
    50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Gln Tyr Tyr Asp Phe Trp Ser Gly Ser Val Gly Arg Asn
            100                 105                 110

Tyr Asp Gly Met Asp Val Trp Gly Leu Gly Thr Thr Val Thr Val Ser
            115                 120                 125

Ser
```

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Ile Val Met Thr Gln Ser Pro Leu Ser Leu Ser Val Thr Pro Gly
 1               5                  10                  15

Glu Pro Ala Ser Ile Ser Cys Arg Ser Ser Gln Ser Leu Leu His Arg
                20                  25                  30

Ser Gly Asn Asn Tyr Leu Asp Trp Tyr Leu Gln Lys Pro Gly His Ser
            35                  40                  45

Pro Gln Leu Leu Ile Tyr Val Gly Ser Asn Arg Ala Ser Gly Val Pro
        50                  55                  60

Asp Arg Phe Ser Gly Ser Gly Ser Gly Thr Glu Tyr Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110
```

<210> SEQ ID NO 34
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Lys Gln Ser Gly Pro Gly Leu Val Lys Pro Ser Gln
 1               5                  10                  15

Thr Leu Ser Leu Thr Cys Thr Val Ser Gly Phe Ser Leu Ser Thr Tyr
                20                  25                  30

Gly Val Gln Trp Val Arg Gln Pro Pro Gly Lys Gly Leu Glu Trp Leu
            35                  40                  45

Gly Val Ile Trp Ser Gly Gly Asn Thr Asp Tyr Asn Ala Ala Phe Ile
        50                  55                  60

Ser Arg Val Thr Ile Ser Lys Asp Thr Ser Asn Gln Val Ser Leu
 65                 70                  75                  80

Lys Leu Ser Ser Val Thr Ala Ala Asp Thr Ala Val Tyr Tyr Cys Ala
                85                  90                  95
```

-continued

Arg Ala Arg Tyr Phe Asp Val Trp Gly Ala Gly Thr Thr Val Thr Val
            100                 105                 110
Ser Ser

<210> SEQ ID NO 35
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Ile Thr Thr Asn
            20                  25                  30

Asn Phe Ala Asn Trp Phe Gln Gln Lys Pro Gly Gln Ala Phe Arg Gly
        35                  40                  45

Leu Ile Gly Asp Thr Asn Asn Arg Val Pro Gly Val Pro Ala Arg Phe
    50                  55                  60

Ser Gly Ser Leu Leu Gly Asn Lys Ala Ala Leu Thr Ile Thr Gly Ala
65                  70                  75                  80

Gln Pro Glu Asp Glu Ala Glu Tyr Tyr Cys Ala Leu Trp Tyr Asn Asn
                85                  90                  95

Trp Val Phe Gly Gly Gly Thr Lys Leu Thr Val Leu Gly
            100                 105

<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Ile Thr Thr Asn
            20                  25                  30

Asn Phe Ala Asn Trp Phe Gln Gln Lys Pro Gly Gln Ala Phe Arg Gly
        35                  40                  45

Leu Ile Gly Asp Thr Asn Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Pro Glu Asp Glu Ala Glu Tyr Tyr Cys Ala Leu Trp Tyr Asn Asn
                85                  90                  95

Trp Val Phe Gly Gly Gly Thr Lys Leu Thr Val Leu Gly
            100                 105

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 37

```
Gln Val Gln Leu Val Glu Ser Gly Gly Gly Val Val Gln Pro Gly Gly
1               5                   10                  15

Ser Leu Arg Leu Ser Cys Ala Pro Ser Gly Phe Val Phe Arg Ser Tyr
            20                  25                  30

Gly Met His Trp Val Arg Gln Thr Pro Gly Lys Gly Leu Glu Trp Val
        35                  40                  45

Ser Leu Ile Trp His Asp Gly Ser Asn Arg Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Ala Arg Glu Arg Leu Ile Ala Ala Pro Ala Ala Phe Asp Leu Trp Gly
            100                 105                 110

Gln Gly Thr Leu Val Thr Val Ser Ser
        115                 120
```

<210> SEQ ID NO 38
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Ser Tyr Val Leu Thr Gln Pro Pro Ser Val Ser Val Ala Pro Gly Lys
1               5                   10                  15

Thr Ala Arg Ile Ser Cys Gly Gly Asn Asn Ile Gly Thr Lys Asn Val
            20                  25                  30

His Trp Tyr Gln Gln Lys Pro Gly Gln Ala Pro Val Leu Val Val Tyr
        35                  40                  45

Ala Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Tyr Cys Gln Val Trp Asp Ser Val Ser Tyr His
                85                  90                  95

Val Val Phe Gly Gly Gly Thr Thr Leu Thr Val Leu Gly
            100                 105
```

<210> SEQ ID NO 39
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45
```

Ser Arg Tyr Gly Met His Trp Val Arg Gln Ala Pro Gly Lys Gly Leu
    50                  55                  60

Glu Trp Val Ala Val Ile Ser Tyr Asp Gly Ser Asn Lys Trp Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met His Ser Leu Arg Ala Ala Asp Thr Gly Val
            100                 105                 110

Tyr Tyr Cys Ala Lys Asp Gln Leu Tyr Phe Gly Ser Gln Ser Pro Gly
        115                 120                 125

His Tyr Trp Val Gln Gly Thr Leu Val Thr Val Ser Ser
    130                 135                 140

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ser Gln Leu Thr Gln Pro Pro Ser Val Ser Val Ala Pro Gly Gln
1               5                   10                  15

Thr Ala Arg Ile Thr Cys Gly Gly Asp Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Asn Glu Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 41
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Asp Met Tyr Trp Val Arg Gln Ala Thr Gly Lys Gly Leu
    50                  55                  60

Glu Trp Val Ser Ala Ile Gly Pro Thr Gly Asp Thr Tyr Tyr Ala Asp
65                  70                  75                  80

Ser Val Lys Gly Arg Phe Thr Ile Ser Arg Glu Asn Ala Lys Asn Ser
                85                  90                  95

```
Leu Tyr Leu Thr Met Asn Gly Leu Arg Ala Gly Asp Thr Ala Val Tyr
            100                 105                 110

Tyr Cys Ala Arg Asp Leu Glu Leu Trp Gly Gln Gly Thr Leu Val Thr
        115                 120                 125

Val Ser Ser
    130

<210> SEQ ID NO 42
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Thr Arg Val Pro Ala Gln Leu Leu Gly Leu Leu Met Leu Trp
1               5                   10                  15

Val Pro Gly Ser Ser Gly Asp Val Val Thr Gln Ser Pro Leu Ser
            20                  25                  30

Leu Pro Val Thr Leu Gly Gln Pro Ala Ser Ile Ser Cys Arg Ser Ser
            35                  40                  45

Leu Ser Leu Val Asp Ser Asp Gly Asn Thr Tyr Leu Asn Trp Phe Leu
50                  55                  60

Gln Arg Pro Gly Gln Ser Pro Arg Arg Leu Ile Tyr Gln Leu Ser Ser
65                  70                  75                  80

Arg Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Ile Thr Phe Gly Gln Gly
        115                 120                 125

Thr Arg Leu Glu Ile Lys Arg
    130                 135

<210> SEQ ID NO 43
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Lys His Leu Trp Phe Phe Leu Leu Leu Val Ala Val Pro Arg Trp
1               5                   10                  15

Val Val Ser Gln Val Gln Leu Gln Glu Ser Gly Pro Gly Leu Val Lys
            20                  25                  30

Ala Ala Glu Thr Leu Ser Leu Thr Cys Thr Val Ser Arg Gly Ser Phe
            35                  40                  45

Ser Asp Tyr Phe Trp Asn Trp Phe Arg Gln Pro Ala Gly Lys Arg Leu
50                  55                  60

Glu Trp Leu Gly Arg Val Tyr Thr Ser Gly Ser Val Asp Tyr Asn Pro
65                  70                  75                  80

Ser Leu Lys Ser Arg Val Thr Val Ser Val Asp Thr Ser Lys Lys Gln
                85                  90                  95

Phe Ser Leu Arg Leu Ser Ser Val Thr Val Ala Asp Thr Ala Val Tyr
            100                 105                 110
```

```
Tyr Cys Ala Arg Gly Leu Ser Gly Phe Asp Tyr Trp Gly Gln Gly Ala
        115                 120                 125

Leu Val Thr Val Ser Pro
    130

<210> SEQ ID NO 44
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Arg Pro Val Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Val Thr Cys Arg Ala Ser Gln Gly
        35                  40                  45

Ile Ser Ser Trp Leu Ala Trp Tyr Gln Gln Lys Pro Gly Lys Ala Pro
    50                  55                  60

Lys Leu Leu Ile His Ala Ala Ser Ser Leu Gln Ser Gly Val Pro Ser
65                  70                  75                  80

Arg Phe Ile Gly Ser Gly Ser Gly Thr Asp Phe Thr Leu Thr Ile Thr
                85                  90                  95

Ser Leu Gln Ala Glu Asp Phe Ala Thr Tyr Tyr Cys Gln Gln Ala Asp
            100                 105                 110

Ser Leu Pro Phe Thr Phe Gly Gly Gly Thr Lys Val Asp Phe Lys Arg
        115                 120                 125

<210> SEQ ID NO 45
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Ser Thr Ala Ile Leu Gly Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ser Tyr Trp Ile Ser Trp Val Arg Gln Met Pro Gly Lys Gly Leu
    50                  55                  60

Glu Trp Met Gly Arg Leu Asp Pro Ser Ala Ser Ala Ile Phe Ser
65                  70                  75                  80

Pro Ser Leu Gln Gly His Val Thr Ile Ser Val Asp Lys Ser Met Arg
                85                  90                  95

Thr Ala Tyr Val Gln Trp Arg Ser Leu Lys Ala Ser Asp Thr Ala Met
            100                 105                 110

Tyr Tyr Cys Ala Arg His Val Arg Glu Lys Ser Met Val Gln Gly Val
        115                 120                 125
```

Ile Ile Lys Asp Ala Phe Asp Ile Trp Gly Gln Gly Thr Met Val Thr
130                 135                 140

Val Ser Ser
145

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Gln Leu Thr Gln Pro Ala Ser Val Ser Val Ser Pro Gly Gln
1               5                   10                  15

Thr Ala Ser Ile Thr Cys Ser Gly Asp Arg Leu Gly Asp Glu Phe Ala
                20                  25                  30

Ser Trp Tyr Gln Gln Lys Pro Gly Gln Ser Pro Ile Leu Val Ile Phe
        35                  40                  45

Glu Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Leu Ala Trp Ala Ser Ser Leu Trp Val
                85                  90                  95

Phe Gly Gly Gly Thr Lys Leu Thr Val Leu
            100                 105

<210> SEQ ID NO 47
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Ser Tyr Ala Gln Lys Phe
50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Ala Glu Ala Tyr Trp Gly Gln Gly Thr Leu Val Thr
            100                 105                 110

Val Ser Ser
        115

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Pro
        35                  40                  45

Pro Gln Arg Leu Ile Tyr Leu Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

Arg

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Lys Leu His Glu Ser Gly Ala Gly Leu Val Lys Pro Gly Ala
1               5                   10                  15

Ser Val Asn Leu Ser Cys Thr Ala Ser Gly Phe Asn Ile Lys Asp Thr
            20                  25                  30

Tyr Met His Trp Val Lys Gln Arg Pro Asp Gln Gly Leu Glu Trp Ile
        35                  40                  45

Gly Arg Ile Asp Pro Ala Asn Gly Asn Thr Lys Ser Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Tyr Ser Trp Gly Gln Gly Thr Thr Val Thr Val Ser Ser
            100                 105                 110

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Glu Leu Thr Gln Ser Pro Val Ser Leu Gly Gln Arg Ala Thr
1               5                   10                  15

Ile Ser Cys Lys Ala Ser Gln Ser Val Asp Tyr Asp Gly Asp Ser Tyr
            20                  25                  30

```
Met Asn Trp Tyr Gln Gln Lys Pro Gly Gln Pro Pro Lys Leu Leu Ile
            35                  40                  45

Tyr Ala Ala Ser Asn Leu Glu Ser Gly Ile Pro Ala Arg Phe Ser Gly
        50                  55                  60

Ser Gly Ser Gly Thr Asp Phe Thr Leu Asn Ile His Pro Val Glu Glu
 65                  70                  75                  80

Glu Asp Ala Ala Thr Tyr Tyr Cys Gln Gln Ser Asn Glu Asp Pro Leu
                85                  90                  95

Thr Phe Gly Gly Gly Thr Lys Leu Glu Leu Lys
                100                 105
```

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser His Ala Asn Tyr Asn Gln Lys Phe
 50                  55                  60

Lys Gly Lys Ala Thr Leu Thr Val Asp Lys Ser Ser Ser Thr Val Tyr
 65                  70                  75                  80

Met Gln Leu Ser Ser Leu Thr Ser Glu Asp Ser Ala Val Tyr Phe Cys
                85                  90                  95

Thr Asn Gly Tyr Trp Gly Gln Gly Thr Thr Leu Thr Val Ser Ser Ala
                100                 105                 110
```

<210> SEQ ID NO 52
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Met Val Ser Lys Leu Asp Ser Gly Val Pro
        50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                85                  90                  95
```

Thr His Phe Pro Phe Thr Phe Gly Ser Gly Thr Lys Leu Glu Ile Lys
            100                 105                 110

Arg

<210> SEQ ID NO 53
<211> LENGTH: 452
<212> TYPE: PRT
<213> ORGANISM: Homo sapiens

<400> SEQUENCE: 53

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

```
Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Thr Tyr Thr Cys Val Ala His
                405                 410                 415

Glu Ala Leu Pro Asn Arg Val Thr Glu Arg Thr Val Asp Lys Ser Thr
                420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 54
<211> LENGTH: 159
<212> TYPE: PRT
<213> ORGANISM: Homo sapiens

<400> SEQUENCE: 54

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
                100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
        130                 135                 140

Lys Met Val Glu Thr Ala Leu Thr Pro Asp Ala Cys Tyr Pro Asp
145                 150                 155

<210> SEQ ID NO 55
<211> LENGTH: 353
<212> TYPE: PRT
<213> ORGANISM: Homo sapiens

<400> SEQUENCE: 55

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60
```

```
Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 56
<211> LENGTH: 340
<212> TYPE: PRT
<213> ORGANISM: Homo sapiens

<400> SEQUENCE: 56

Ala Ser Pro Thr Ser Pro Lys Val Phe Pro Leu Ser Leu Asp Ser Thr
 1               5                  10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
 65                  70                  75                  80
```

```
Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
            210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 57
<211> LENGTH: 585
<212> TYPE: PRT
<213> ORGANISM: Homo sapiens

<400> SEQUENCE: 57

Lys Ser Pro Ile Phe Gly Pro Glu Glu Val Asn Ser Val Glu Gly Asn
1               5                   10                  15

Ser Val Ser Ile Thr Cys Tyr Tyr Pro Pro Thr Ser Val Asn Arg His
            20                  25                  30

Thr Arg Lys Tyr Trp Cys Arg Gln Gly Ala Arg Gly Gly Cys Ile Thr
            35                  40                  45

Leu Ile Ser Ser Glu Gly Tyr Val Ser Ser Lys Tyr Ala Gly Arg Ala
50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
                85                  90                  95

Asn Ser Arg Gly Leu Ser Phe Asp Val Ser Leu Glu Val Ser Gln Gly
            100                 105                 110
```

```
Pro Gly Leu Leu Asn Asp Thr Lys Val Tyr Thr Val Asp Leu Gly Arg
            115                 120                 125

Thr Val Thr Ile Asn Cys Pro Phe Lys Thr Glu Asn Ala Gln Lys Arg
130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
    210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
    290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Ser Thr Ile Pro Arg
                325                 330                 335

Ser Pro Thr Val Val Lys Gly Val Ala Gly Gly Ser Val Ala Val Leu
            340                 345                 350

Cys Pro Tyr Asn Arg Lys Glu Ser Lys Ser Ile Lys Tyr Trp Cys Leu
        355                 360                 365

Trp Glu Gly Ala Gln Asn Gly Arg Cys Pro Leu Leu Val Asp Ser Glu
    370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
                405                 410                 415

Asp Ala Gly Phe Tyr Trp Cys Leu Thr Asn Gly Asp Thr Leu Trp Arg
            420                 425                 430

Thr Thr Val Glu Ile Lys Ile Ile Glu Gly Glu Pro Asn Leu Lys Val
        435                 440                 445

Pro Gly Asn Val Thr Ala Val Leu Gly Glu Thr Leu Lys Val Pro Cys
    450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
                485                 490                 495

Lys Ala Phe Val Asn Cys Asp Glu Asn Ser Arg Leu Val Ser Leu Thr
            500                 505                 510

Leu Asn Leu Val Thr Arg Ala Asp Glu Gly Trp Tyr Trp Cys Gly Val
        515                 520                 525
```

```
Lys Gln Gly His Phe Tyr Gly Glu Thr Ala Ala Val Tyr Val Ala Val
    530                 535                 540

Glu Glu Arg Lys Ala Ala Gly Ser Arg Asp Val Ser Leu Ala Lys Ala
545                 550                 555                 560

Asp Ala Ala Pro Asp Glu Lys Val Leu Asp Ser Gly Phe Arg Glu Ile
                565                 570                 575

Glu Asn Lys Ala Ile Gln Asp Pro Arg
            580                 585

<210> SEQ ID NO 58
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Ala Pro Gly Ala
1               5                   10                  15

Ser Val Lys Val Ser Cys Lys Ala Ser Gly Tyr Thr Phe Thr Ser Ala
            20                  25                  30

Trp Met Asn Trp Val Arg Gln Ala Pro Gly Gln Gly Leu Glu Trp Met
        35                  40                  45

Gly Arg Ile Tyr Pro Ser Gly Gly Ser Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Arg Val Ala Arg Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 59
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Pro
        35                  40                  45

Pro Gln Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 60
<211> LENGTH: 119
<212> TYPE: PRT
<213> ORGANISM: Hepatitis B virus

<400> SEQUENCE: 60

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp Gln Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala
        115

<210> SEQ ID NO 61
<211> LENGTH: 154
<212> TYPE: PRT
<213> ORGANISM: Hepatitis B virus

<400> SEQUENCE: 61

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Pro Phe Gly Thr Leu Pro Ser Pro Ser Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Val Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 62
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 62

Gln Val Gln Leu Val Gln Ser Gly Ala Glu Val Lys Ala Pro Gly Ala
1               5                   10                  15

Ser Val Lys Val Ser Cys Lys Ala Ser Gly Tyr Thr Phe Thr Ser Ala
            20                  25                  30

Trp Met Asn Trp Val Arg Gln Ala Pro Gly Gln Gly Leu Glu Trp Met
        35                  40                  45

Gly Arg Ile Tyr Pro Ser Gly Gly Ser Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Asp Glu Ala Tyr Trp Gly Gln Gly Thr Leu Val Thr
            100                 105                 110

Val Ser Ser
        115

<210> SEQ ID NO 63
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Gln Ser Gly Ala Glu Val Lys Ala Pro Gly Ala
1               5                   10                  15

Ser Val Lys Val Ser Cys Lys Ala Ser Gly Tyr Thr Phe Thr Ser Ala
            20                  25                  30

Trp Met Asn Trp Val Arg Gln Ala Pro Gly Gln Gly Leu Glu Trp Met
        35                  40                  45

Gly Arg Ile Tyr Pro Ser Gly Gly Ser Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Asp Glu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 64

<400> SEQUENCE: 64

000

<210> SEQ ID NO 65

<400> SEQUENCE: 65

000

<210> SEQ ID NO 66
<211> LENGTH: 1239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atgggctggt cctacatcat cctcttcctc gtggccacag ccacaggcgt ccatagccag      60
gtgcagctgg tgcagtccgg cgccgaagtg aagaagcctg gcgccagcgt gaaggtgagc     120
tgcaaggctt ccggctacac cttcatctcc tacaccatgc actgggtgag gcaagctcct     180
ggccagggcc tggagtggat gggatacatc aaccctcggt ccggctatac ccactacaat     240
cagaagctga aggacaaggc cacsctgacc gctgacaagt ccgcctccac cgcttacatg     300
gagctgtcct ccctgaggtc cgaggacacc gccgtgtact actgtgccag gtccgcctac     360

```
tacgactacg acggattcgc ttactggggc cagggcaccc tggtgacagt gagctccgga     420
ggaggaggca gcggcggcgg cggcagcggc ggcggcggca gcgatatcca gatgacccag     480
agcccttcca gcctgtccgc ttccgtgggc gacagggtga ccatcacctg cagcgcttcc     540
tcctccgtgt cctacatgaa ctggtaccag cagaagcctg gcaaggcccc caagaggctg     600
atctacgaca cctccaagct ggcctccgga gtgccttcca ggttcagcgg ctccggctcc     660
ggaaccgact tcaccctgac cattagctcc ctgcagcccg aggacttcgc cacctactac     720
tgccagcagt ggtccagcaa ccctcccacc ttcggcggcg gcacaaagct ggagatcaag     780
ggaggaggag gatccggtgg tggtggttct ggcggaggtg gatcccaaga agatgaaagg     840
attgttcttg ttgacaacaa atgtaagtgt gcccggatta cttccaggat catccgttct     900
tccgaagatc ctaatgagga cattgtggag agaaacatcc gaattattgt tcctctgaac     960
aacagggaga atatctctga tcccacctca ccattgagaa ccagatttgt gtaccatttg    1020
tctgacctct gtaaaaaatg tgatcctaca gaagtggagc tggataatca gatagttact    1080
gctacccaga gcaatatctg tgatgaagac agtgctacag agacctgcta cacttatgac    1140
agaaacaagt gctacacagc tgtggtccca ctcgtatatg gtggtgagac caaaatggtg    1200
gaaacagcct aaccccaga tgcctgctat cctgactga                           1239
```

<210> SEQ ID NO 67
<211> LENGTH: 412
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 67

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Ser Tyr Thr Met His Trp Val Arg Gln Ala Pro Gly Gln Gly Leu
    50                  55                  60

Glu Trp Met Gly Tyr Ile Asn Pro Arg Ser Gly Tyr Thr His Tyr Asn
65                  70                  75                  80

Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
        195                 200                 205

```
Ser Gly Val Pro Ser Arg Phe Ser Gly Ser Gly Thr Asp Phe
    210             215             220

Thr Leu Thr Ile Ser Ser Leu Gln Pro Glu Asp Phe Ala Thr Tyr Tyr
225             230             235             240

Cys Gln Gln Trp Ser Ser Asn Pro Pro Thr Phe Gly Gly Gly Thr Lys
                245             250             255

Leu Glu Ile Lys Gly Gly Gly Ser Gly Gly Gly Ser Gly Gly
            260             265             270

Gly Gly Ser Gln Glu Asp Glu Arg Ile Val Leu Val Asp Asn Lys Cys
        275             280             285

Lys Cys Ala Arg Ile Thr Ser Arg Ile Arg Ser Ser Glu Asp Pro
290             295             300

Asn Glu Asp Ile Val Glu Arg Asn Ile Arg Ile Ile Val Pro Leu Asn
305             310             315             320

Asn Arg Glu Asn Ile Ser Asp Pro Thr Ser Pro Leu Arg Thr Arg Phe
                325             330             335

Val Tyr His Leu Ser Asp Leu Cys Lys Lys Cys Asp Pro Thr Glu Val
            340             345             350

Glu Leu Asp Asn Gln Ile Val Thr Ala Thr Gln Ser Asn Ile Cys Asp
        355             360             365

Glu Asp Ser Ala Thr Glu Thr Cys Tyr Thr Tyr Asp Arg Asn Lys Cys
370             375             380

Tyr Thr Ala Val Val Pro Leu Val Tyr Gly Glu Thr Lys Met Val
385             390             395             400

Glu Thr Ala Leu Thr Pro Asp Ala Cys Tyr Pro Asp
            405             410

<210> SEQ ID NO 68
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160
```

```
Ser Ser Ser Val Ser Tyr Met Asn Trp Tyr Gln Gln Lys Pro Gly Lys
            165                 170                 175

Ala Pro Lys Arg Leu Ile Tyr Asp Thr Ser Lys Leu Ala Ser Gly Val
        180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
        210                 215                 220

Trp Ser Ser Asn Pro Pro Thr Phe Gly Gly Gly Thr Lys Leu Glu Ile
225                 230                 235                 240

Lys Gly Gly Gly Ser Gly Gly Gly Ser Gly Gly Gly Ser
                245                 250                 255

Gln Glu Asp Glu Arg Ile Val Leu Val Asp Asn Lys Cys Lys Cys Ala
            260                 265                 270

Arg Ile Thr Ser Arg Ile Ile Arg Ser Ser Glu Asp Pro Asn Glu Asp
            275                 280                 285

Ile Val Glu Arg Asn Ile Arg Ile Ile Val Pro Leu Asn Asn Arg Glu
        290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
            340                 345                 350

Ala Thr Glu Thr Cys Tyr Thr Tyr Asp Arg Asn Lys Cys Tyr Thr Ala
        355                 360                 365

Val Val Pro Leu Val Tyr Gly Gly Glu Thr Lys Met Val Glu Thr Ala
        370                 375                 380

Leu Thr Pro Asp Ala Cys Tyr Pro Asp
385                 390
```

<210> SEQ ID NO 69
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
atgaagaacc atttgctttt ctggggagtc ctggcggttt ttattaaggc tgttcatgtg      60
aaagcccaag aagatgaaag gattgttctt gttgacaaca atgtaagtg tgcccggatt     120
acttccagga tcatccgttc ttccgaagat cctaatgagg acattgtgga gagaaacatc    180
cgaattattg ttcctctgaa caacagggag aatatctctg atcccacctc accattgaga    240
accagatttg tgtaccattt gtctgacctc tgtaaaaaat gtgatcctac agaagtggag    300
ctggataatc agatagttac tgctacccag agcaatatct gtgatgaaga cagtgctaca    360
gagacctgct acacttatga cagaaacaag tgctacacag ctgtggtccc actcgtatat    420
ggtggtgaga ccaaaatggt ggaaacagcc ttaaccccag atgcctgcta tcctgacgga    480
ggaggaggat ccggtggtgg tggttctggc ggaggtggat cccaggtgca gctggtgcag    540
tccggcgccg aagtgaagaa gcctggcgcc agcgtgaagg tgagctgcaa ggcttccggc    600
tacaccttca tctcctacac catgcactgg gtgaggcaag ctcctggcca gggcctggag    660
tggatgggat acatcaaccc tcggtccggc tataccccact acaatcagaa gctgaaggac    720
```

```
aaggccaccc tgaccgctga caagtccgcc tccaccgctt acatggagct gtcctccctg      780
aggtccgagg acaccgccgt gtactactgt gccaggtccg cctactacga ctacgacgga      840
ttcgcttact ggggccaggg caccctggtg acagtgagct ccggaggagg aggcagcggt      900
ggtggcggaa gcgtggaggt ggcagcgat atccagatga cccagagccc ttccagcctg      960
tccgcttccg tgggcgacag ggtgaccatc acctgcagcg cttcctcctc cgtgtcctac     1020
atgaactggt accagcagaa gcctggcaag gcccccaaga ggctgatcta cgacacctcc     1080
aagctggcct ccggagtgcc ttccaggttc agcggctccg gctccggaac cgacttcacc     1140
ctgaccatta gctccctgca gcccgaggac ttcgccacct actactgcca gcagtggtcc     1200
agcaaccctc ccaccttcgg aggcggcaca aagctggaga tcaagtga               1248
```

<210> SEQ ID NO 70
<211> LENGTH: 415
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 70

```
Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Ser Gly Gly Gly Ser Gln Val
                165                 170                 175

Gln Leu Val Gln Ser Gly Ala Glu Val Lys Lys Pro Gly Ala Ser Val
            180                 185                 190

Lys Val Ser Cys Lys Ala Ser Gly Tyr Thr Phe Ile Ser Tyr Thr Met
        195                 200                 205

His Trp Val Arg Gln Ala Pro Gly Gln Gly Leu Glu Trp Met Gly Tyr
    210                 215                 220

Ile Asn Pro Arg Ser Gly Tyr Thr His Tyr Asn Gln Lys Leu Lys Asp
225                 230                 235                 240

Lys Ala Thr Leu Thr Ala Asp Lys Ser Ala Ser Thr Ala Tyr Met Glu
                245                 250                 255

Leu Ser Ser Leu Arg Ser Glu Asp Thr Ala Val Tyr Tyr Cys Ala Arg
            260                 265                 270
```

```
Ser Ala Tyr Tyr Asp Tyr Asp Gly Phe Ala Tyr Trp Gly Gln Gly Thr
            275                 280                 285

Leu Val Thr Val Ser Ser Gly Gly Gly Ser Gly Gly Gly Gly Ser
        290                 295                 300

Gly Gly Gly Gly Ser Asp Ile Gln Met Thr Gln Ser Pro Ser Ser Leu
305                 310                 315                 320

Ser Ala Ser Val Gly Asp Arg Val Thr Ile Thr Cys Ser Ala Ser Ser
                325                 330                 335

Ser Val Ser Tyr Met Asn Trp Tyr Gln Gln Lys Pro Gly Lys Ala Pro
            340                 345                 350

Lys Arg Leu Ile Tyr Asp Thr Ser Lys Leu Ala Ser Gly Val Pro Ser
        355                 360                 365

Arg Phe Ser Gly Ser Gly Ser Gly Thr Asp Phe Thr Leu Thr Ile Ser
    370                 375                 380

Ser Leu Gln Pro Glu Asp Phe Ala Thr Tyr Tyr Cys Gln Gln Trp Ser
385                 390                 395                 400

Ser Asn Pro Pro Thr Phe Gly Gly Gly Thr Lys Leu Glu Ile Lys
                405                 410                 415

<210> SEQ ID NO 71
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
    130                 135                 140

Gly Gly Ser Gly Gly Gly Ser Gln Val Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Thr Phe Ile Ser Tyr Thr Met His Trp Val Arg Gln Ala
            180                 185                 190

Pro Gly Gln Gly Leu Glu Trp Met Gly Tyr Ile Asn Pro Arg Ser Gly
        195                 200                 205

Tyr Thr His Tyr Asn Gln Lys Leu Lys Asp Lys Ala Thr Leu Thr Ala
    210                 215                 220
```

Asp Lys Ser Ala Ser Thr Ala Tyr Met Glu Leu Ser Ser Leu Arg Ser
225                 230                 235                 240

Glu Asp Thr Ala Val Tyr Tyr Cys Ala Arg Ser Ala Tyr Tyr Asp Tyr
            245                 250                 255

Asp Gly Phe Ala Tyr Trp Gly Gln Gly Thr Leu Val Thr Val Ser Ser
            260                 265                 270

Gly Gly Gly Gly Ser Gly Gly Gly Ser Gly Gly Gly Gly Ser Asp
        275                 280                 285

Ile Gln Met Thr Gln Ser Pro Ser Ser Leu Ser Ala Ser Val Gly Asp
        290                 295                 300

Arg Val Thr Ile Thr Cys Ser Ala Ser Ser Val Ser Tyr Met Asn
305                 310                 315                 320

Trp Tyr Gln Gln Lys Pro Gly Lys Ala Pro Lys Arg Leu Ile Tyr Asp
                325                 330                 335

Thr Ser Lys Leu Ala Ser Gly Val Pro Ser Arg Phe Ser Gly Ser Gly
            340                 345                 350

Ser Gly Thr Asp Phe Thr Leu Thr Ile Ser Ser Leu Gln Pro Glu Asp
            355                 360                 365

Phe Ala Thr Tyr Tyr Cys Gln Gln Trp Ser Ser Asn Pro Pro Thr Phe
370                 375                 380

Gly Gly Gly Thr Lys Leu Glu Ile Lys
385                 390

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Gly Gly Ser Gly Gly Gly Gly Ser Gly Gly Gly Gly Ser
1               5                   10                  15

<210> SEQ ID NO 73
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Val Leu Glu Ser Gly Gly Leu Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Thr Gly Glu Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Asp Ala Ile Leu Gly Ser Gly His Pro Trp Tyr Phe His Val
            100                 105                 110

Trp Gly Arg Gly Thr Leu Val Thr Val Ser Ser
        115                 120

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ser Tyr Val Leu Thr Gln Pro Pro Ser Val Ser Val Ala Pro Gly Gln
1               5                   10                  15

Thr Ala Arg Met Thr Cys Gly Gly Asn Asn Ile Gly Ser Glu Ser Val
            20                  25                  30

His Trp Phe Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Ala Val Phe Gly Gly Gly Thr Gln Leu Thr Val Leu
            100                 105

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Val Ser Ser Asp Gly Ser Tyr Ala Tyr Tyr Pro Asp Thr Leu
    50                  55                  60

Thr Gly Arg Phe Thr Ile Ser Arg Asp Asn Ala Lys Asn Thr Leu Tyr
65                  70                  75                  80

Leu Glu Met Thr Ser Leu Arg Ser Glu Asp Thr Ala Met Tyr Tyr Cys
                85                  90                  95

Ala Ser Phe Asn Trp Asp Val Ala Tyr Trp Gly Gln Gly Thr Leu Val
            100                 105                 110

Thr Val Ser Ala Ala
        115

<210> SEQ ID NO 76
<211> LENGTH: 113
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 76

Glu Leu Val Met Thr Gln Ser Pro Ser Ser Leu Ala Val Ser Val Gly
1               5                   10                  15

Glu Lys Val Thr Met Ser Cys Arg Ser Ser Gln Ser Leu Leu Asn Thr
                20                  25                  30

Arg Thr Arg Lys Ser Tyr Leu Ala Trp Phe Gln Gln Lys Pro Gly Gln
            35                  40                  45

Ser Pro Lys Met Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Ser Leu Tyr Thr Phe Gly Gly Gly Thr Lys Leu Glu Ile Lys
                100                 105                 110

Arg

<210> SEQ ID NO 77
<211> LENGTH: 7
<212> TYPE: PRT
<213> ORGANISM: Hepatitis B virus

<400> SEQUENCE: 77

Asn Thr Ala Asn Pro Asp Trp
1               5

<210> SEQ ID NO 78
<211> LENGTH: 419
<212> TYPE: PRT
<213> ORGANISM: Hepatitis B virus

<400> SEQUENCE: 78

Met Glu Trp Ser Trp Val Phe Leu Phe Leu Ser Val Thr Thr Gly
1               5                   10                  15

Val His Ser Met Gly Gly Trp Ser Ser Lys Pro Arg Lys Gly Met Gly
                20                  25                  30

Thr Asn Leu Ser Val Pro Asn Pro Leu Gly Phe Phe Pro Asp His Gln
            35                  40                  45

Leu Asp Pro Ala Phe Gly Ala Asn Ser Asn Asn Pro Asp Trp Asp Phe
50                  55                  60

Asn Pro Ile Lys Asp His Trp Pro Ala Ala Asn Gln Val Gly Val Gly
65                  70                  75                  80

Ala Phe Gly Pro Gly Leu Thr Pro Pro His Gly Gly Ile Leu Gly Trp
                85                  90                  95

Ser Pro Gln Ala Gln Gly Ile Leu Thr Thr Val Ser Thr Ile Pro Pro
                100                 105                 110

Pro Ala Ser Thr Asn Arg Gln Ser Gly Arg Gln Pro Thr Pro Ile Ser
            115                 120                 125

Pro Pro Leu Arg Asp Ser His Pro Gln Ala Met Gln Trp Asn Ser Thr
        130                 135                 140

Ala Phe His Gln Ala Leu Gln Asp Pro Arg Val Arg Gly Leu Tyr Phe
145                 150                 155                 160
```

```
Pro Ala Gly Gly Ser Ser Gly Thr Val Asn Pro Ala Pro Asn Ile
                165                 170                 175

Ala Ser His Ile Ser Ser Ile Ser Ala Arg Thr Gly Asp Pro Val Thr
            180                 185                 190

Asn Met Glu Asn Ile Thr Ser Gly Phe Leu Gly Pro Leu Leu Val Leu
            195                 200                 205

Gln Ala Gly Phe Phe Leu Leu Thr Arg Ile Leu Thr Ile Pro Gln Ser
210                 215                 220

Leu Asp Ser Trp Trp Thr Ser Leu Asn Phe Leu Gly Gly Ser Pro Val
225                 230                 235                 240

Cys Leu Gly Gln Asn Ser Gln Ser Pro Thr Ser Asn His Ser Pro Thr
                245                 250                 255

Ser Cys Pro Pro Ile Cys Pro Gly Tyr Arg Trp Met Cys Leu Arg Arg
            260                 265                 270

Phe Ile Ile Phe Leu Phe Ile Leu Leu Leu Cys Leu Ile Phe Leu Leu
            275                 280                 285

Val Leu Leu Asp Tyr Gln Gly Met Leu Pro Val Cys Pro Leu Ile Pro
    290                 295                 300

Gly Ser Thr Thr Thr Ser Thr Gly Pro Cys Lys Thr Cys Thr Thr Pro
305                 310                 315                 320

Ala Gln Gly Asn Ser Met Phe Pro Ser Cys Cys Cys Thr Lys Pro Thr
                325                 330                 335

Asp Gly Asn Cys Thr Cys Ile Pro Ile Pro Ser Ser Trp Ala Phe Ala
            340                 345                 350

Lys Tyr Leu Trp Glu Trp Ala Ser Val Arg Phe Ser Trp Leu Ser Leu
            355                 360                 365

Leu Val Pro Phe Val Gln Trp Phe Val Gly Leu Ser Pro Thr Val Trp
    370                 375                 380

Leu Ser Ala Ile Trp Met Met Trp Tyr Trp Gly Pro Ser Leu Tyr Ser
385                 390                 395                 400

Ile Val Ser Pro Phe Ile Pro Leu Leu Pro Ile Phe Phe Cys Leu Trp
                405                 410                 415

Val Tyr Ile

<210> SEQ ID NO 79
<211> LENGTH: 400
<212> TYPE: PRT
<213> ORGANISM: Hepatitis B virus

<400> SEQUENCE: 79

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Ile
            35                  40                  45

Lys Asp His Trp Pro Ala Ala Asn Gln Val Gly Val Gly Ala Phe Gly
    50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110
```

```
Arg Asp Ser His Pro Gln Ala Met Gln Trp Asn Ser Thr Ala Phe His
            115                 120                 125
Gln Ala Leu Gln Asp Pro Arg Val Arg Gly Leu Tyr Phe Pro Ala Gly
    130                 135                 140
Gly Ser Ser Ser Gly Thr Val Asn Pro Ala Pro Asn Ile Ala Ser His
145                 150                 155                 160
Ile Ser Ser Ile Ser Ala Arg Thr Gly Asp Pro Val Thr Asn Met Glu
                165                 170                 175
Asn Ile Thr Ser Gly Phe Leu Gly Pro Leu Leu Val Leu Gln Ala Gly
            180                 185                 190
Phe Phe Leu Leu Thr Arg Ile Leu Thr Ile Pro Gln Ser Leu Asp Ser
    195                 200                 205
Trp Trp Thr Ser Leu Asn Phe Leu Gly Gly Ser Pro Val Cys Leu Gly
210                 215                 220
Gln Asn Ser Gln Ser Pro Thr Ser Asn His Ser Pro Thr Ser Cys Pro
225                 230                 235                 240
Pro Ile Cys Pro Gly Tyr Arg Trp Met Cys Leu Arg Arg Phe Ile Ile
                245                 250                 255
Phe Leu Phe Ile Leu Leu Leu Cys Leu Ile Phe Leu Leu Val Leu Leu
            260                 265                 270
Asp Tyr Gln Gly Met Leu Pro Val Cys Pro Leu Ile Pro Gly Ser Thr
    275                 280                 285
Thr Thr Ser Thr Gly Pro Cys Lys Thr Cys Thr Thr Pro Ala Gln Gly
290                 295                 300
Asn Ser Met Phe Pro Ser Cys Cys Cys Thr Lys Pro Thr Asp Gly Asn
305                 310                 315                 320
Cys Thr Cys Ile Pro Ile Pro Ser Ser Trp Ala Phe Ala Lys Tyr Leu
                325                 330                 335
Trp Glu Trp Ala Ser Val Arg Phe Ser Trp Leu Ser Leu Leu Val Pro
            340                 345                 350
Phe Val Gln Trp Phe Val Gly Leu Ser Pro Thr Val Trp Leu Ser Ala
    355                 360                 365
Ile Trp Met Met Trp Tyr Trp Gly Pro Ser Leu Tyr Ser Ile Val Ser
370                 375                 380
Pro Phe Ile Pro Leu Leu Pro Ile Phe Phe Cys Leu Trp Val Tyr Ile
385                 390                 395                 400

<210> SEQ ID NO 80
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Pro Lys Gly Ser Leu Ser Trp Arg Ile Leu Leu Phe Leu Ser
1               5                   10                  15
Leu Ala Phe Glu Leu Ser Tyr Gly Glu Val Gln Val Leu Glu Ser Gly
            20                  25                  30
Gly Gly Leu Val Gln Pro Gly Gly Ser Leu Arg Leu Ser Cys Ala Ala
        35                  40                  45
Ser Gly Phe Arg Phe Ser Ser Tyr Ala Met Ser Trp Val Arg Gln Ala
    50                  55                  60
Pro Gly Lys Gly Leu Glu Trp Val Ser Gly Ile Ser Gly Thr Gly Glu
65                  70                  75                  80
```

```
Asn Thr Tyr Tyr Ala Asp Ser Val Lys Gly Arg Phe Thr Ile Ser Arg
                85                  90                  95
Asp Asn Ser Lys Asn Thr Leu Tyr Val Gln Met Asn Ser Leu Arg Ala
            100                 105                 110
Glu Asp Thr Ala Val Tyr Tyr Cys Ala Lys Asp Ala Ile Leu Gly Ser
        115                 120                 125
Gly His Pro Trp Tyr Phe His Val Trp Gly Arg Gly Thr Leu Val Thr
    130                 135                 140
Val Ser Ser Gly Ser Ala Ser Ala Pro Thr Leu Phe Pro Leu Val Ser
145                 150                 155                 160
Cys Glu Asn Ser Pro Ser Asp Thr Ser Ser Val Ala Val Gly Cys Leu
                165                 170                 175
Ala Gln Asp Phe Leu Pro Asp Ser Ile Thr Phe Ser Trp Lys Tyr Lys
            180                 185                 190
Asn Asn Ser Asp Ile Ser Ser Thr Arg Gly Phe Pro Ser Val Leu Arg
        195                 200                 205
Gly Gly Lys Tyr Ala Ala Thr Ser Gln Val Leu Leu Pro Ser Lys Asp
    210                 215                 220
Val Met Gln Gly Thr Asp Glu His Val Val Cys Lys Val Gln His Pro
225                 230                 235                 240
Asn Gly Asn Lys Glu Lys Asn Val Pro Leu Pro Val Ile Ala Glu Leu
                245                 250                 255
Pro Pro Lys Val Ser Val Phe Val Pro Pro Arg Asp Gly Phe Phe Gly
            260                 265                 270
Asn Pro Arg Lys Ser Lys Leu Ile Cys Gln Ala Thr Gly Phe Ser Pro
        275                 280                 285
Arg Gln Ile Gln Val Ser Trp Leu Arg Glu Gly Lys Gln Val Gly Ser
    290                 295                 300
Gly Val Thr Thr Asp Gln Val Gln Ala Glu Ala Lys Glu Ser Gly Pro
305                 310                 315                 320
Thr Thr Tyr Lys Val Thr Ser Thr Leu Thr Ile Lys Glu Ser Asp Trp
                325                 330                 335
Leu Ser Gln Ser Met Phe Thr Cys Arg Val Asp His Arg Gly Leu Thr
            340                 345                 350
Phe Gln Gln Asn Ala Ser Ser Met Cys Val Pro Asp Gln Asp Thr Ala
        355                 360                 365
Ile Arg Val Phe Ala Ile Pro Pro Ser Phe Ala Ser Ile Phe Leu Thr
    370                 375                 380
Lys Ser Thr Lys Leu Thr Cys Leu Val Thr Asp Leu Thr Thr Tyr Asp
385                 390                 395                 400
Ser Val Thr Ile Ser Trp Thr Arg Gln Asn Gly Glu Ala Val Lys Thr
                405                 410                 415
His Thr Asn Ile Ser Glu Ser His Pro Asn Ala Thr Phe Ser Ala Val
            420                 425                 430
Gly Glu Ala Ser Ile Cys Glu Asp Asp Trp Asn Ser Gly Glu Arg Phe
        435                 440                 445
Thr Cys Thr Val Thr His Thr Asp Leu Pro Ser Pro Leu Lys Gln Thr
    450                 455                 460
Ile Ser Arg Pro Lys Gly Val Ala Leu His Arg Pro Asp Val Tyr Leu
465                 470                 475                 480
Leu Pro Pro Ala Arg Glu Gln Leu Asn Leu Arg Glu Ser Ala Thr Ile
                485                 490                 495
```

```
Thr Cys Leu Val Thr Gly Phe Ser Pro Ala Asp Val Phe Val Gln Trp
            500                 505                 510

Met Gln Arg Gly Gln Pro Leu Ser Pro Glu Lys Tyr Val Thr Ser Ala
            515                 520                 525

Pro Met Pro Glu Pro Gln Ala Pro Gly Arg Tyr Phe Ala His Ser Ile
            530                 535                 540

Leu Thr Val Ser Glu Glu Trp Asn Thr Gly Glu Thr Tyr Thr Cys
545                 550                 555                 560

Val Val Ala His Glu Ala Leu Pro Asn Arg Val Thr Glu Arg Thr Val
            565                 570                 575

Asp Lys Ser Thr Gly Lys Pro Thr Leu Tyr Asn Val Ser Leu Val Met
            580                 585                 590

Ser Asp Thr Ala Gly Thr Cys Tyr
            595                 600

<210> SEQ ID NO 81
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ser Val Pro Thr Gln Val Leu Gly Leu Leu Leu Leu Trp Leu Thr
1               5                   10                  15

Asp Ala Arg Cys Ser Tyr Val Leu Thr Gln Pro Pro Ser Val Ser Val
            20                  25                  30

Ala Pro Gly Gln Thr Ala Arg Met Thr Cys Gly Gly Asn Asn Ile Gly
            35                  40                  45

Ser Glu Ser Val His Trp Phe Gln Gln Lys Pro Gly Gln Ala Pro Val
        50                  55                  60

Leu Val Val Tyr Asp Asp Ser Asp Arg Pro Ser Gly Ile Pro Glu Arg
65              70                  75                  80

Phe Ser Gly Ser Asn Ser Gly Asn Thr Ala Thr Leu Thr Ile Ser Arg
                85                  90                  95

Val Glu Ala Gly Asp Glu Ala Asp Tyr Tyr Cys Gln Val Trp Asp Ser
            100                 105                 110

Ser Ser Asp His Ala Val Phe Gly Gly Gly Thr Gln Leu Thr Val Leu
            115                 120                 125

Gly Gln Pro Lys Ala Ala Pro Ser Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

-continued

```
<210> SEQ ID NO 82
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Glu Glu Ser Gly
            20                  25                  30

Gly Gly Leu Val Lys Pro Gly Ser Leu Lys Leu Ser Cys Ala Ala
        35                  40                  45

Ser Gly Phe Thr Phe Ser Ser Tyr Ala Met Ser Trp Val Arg Gln Ser
    50                  55                  60

Pro Glu Lys Arg Leu Glu Trp Val Ala Val Ser Ser Asp Gly Ser
65                  70                  75                  80

Tyr Ala Tyr Tyr Pro Asp Thr Leu Thr Gly Arg Phe Thr Ile Ser Arg
                85                  90                  95

Asp Asn Ala Lys Asn Thr Leu Tyr Leu Glu Met Thr Ser Leu Arg Ser
            100                 105                 110

Glu Asp Thr Ala Met Tyr Tyr Cys Ala Ser Phe Asn Trp Asp Val Ala
        115                 120                 125

Tyr Trp Gly Gln Gly Thr Leu Val Thr Val Ser Ala Gly Ser Ala Ser
    130                 135                 140

Ala Pro Thr Leu Phe Pro Leu Val Ser Cys Glu Asn Ser Pro Ser Asp
145                 150                 155                 160

Thr Ser Ser Val Ala Val Gly Cys Leu Ala Gln Asp Phe Leu Pro Asp
                165                 170                 175

Ser Ile Thr Phe Ser Trp Lys Tyr Lys Asn Asn Ser Asp Ile Ser Ser
            180                 185                 190

Thr Arg Gly Phe Pro Ser Val Leu Arg Gly Gly Lys Tyr Ala Ala Thr
        195                 200                 205

Ser Gln Val Leu Leu Pro Ser Lys Asp Val Met Gln Gly Thr Asp Glu
    210                 215                 220

His Val Val Cys Lys Val Gln His Pro Asn Gly Asn Lys Glu Lys Asn
225                 230                 235                 240

Val Pro Leu Pro Val Ile Ala Glu Leu Pro Pro Lys Val Ser Val Phe
                245                 250                 255

Val Pro Pro Arg Asp Gly Phe Phe Gly Asn Pro Arg Lys Ser Lys Leu
            260                 265                 270

Ile Cys Gln Ala Thr Gly Phe Ser Pro Arg Gln Ile Gln Val Ser Trp
        275                 280                 285

Leu Arg Glu Gly Lys Gln Val Gly Ser Gly Val Thr Thr Asp Gln Val
    290                 295                 300

Gln Ala Glu Ala Lys Glu Ser Gly Pro Thr Thr Tyr Lys Val Thr Ser
305                 310                 315                 320

Thr Leu Thr Ile Lys Glu Ser Asp Trp Leu Ser Gln Ser Met Phe Thr
                325                 330                 335

Cys Arg Val Asp His Arg Gly Leu Thr Phe Gln Gln Asn Ala Ser Ser
            340                 345                 350

Met Cys Val Pro Asp Gln Asp Thr Ala Ile Arg Val Phe Ala Ile Pro
        355                 360                 365
```

```
Pro Ser Phe Ala Ser Ile Phe Leu Thr Lys Ser Thr Lys Leu Thr Cys
        370                 375                 380

Leu Val Thr Asp Leu Thr Thr Tyr Asp Ser Val Thr Ile Ser Trp Thr
385                 390                 395                 400

Arg Gln Asn Gly Glu Ala Val Lys Thr His Thr Asn Ile Ser Glu Ser
                405                 410                 415

His Pro Asn Ala Thr Phe Ser Ala Val Gly Glu Ala Ser Ile Cys Glu
                420                 425                 430

Asp Asp Trp Asn Ser Gly Glu Arg Phe Thr Cys Thr Val Thr His Thr
            435                 440                 445

Asp Leu Pro Ser Pro Leu Lys Gln Thr Ile Ser Arg Pro Lys Gly Val
450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
                500                 505                 510

Ser Pro Glu Lys Tyr Val Thr Ser Ala Pro Met Pro Glu Pro Gln Ala
            515                 520                 525

Pro Gly Arg Tyr Phe Ala His Ser Ile Leu Thr Val Ser Glu Glu Glu
            530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
                580                 585                 590

Tyr

<210> SEQ ID NO 83
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Glu Thr Asp Thr Leu Leu Leu Trp Val Leu Leu Leu Trp Val Pro
1               5                   10                  15

Gly Ser Thr Gly Glu Leu Val Met Thr Gln Ser Pro Ser Ser Leu Ala
                20                  25                  30

Val Ser Val Gly Glu Lys Val Thr Met Ser Cys Arg Ser Ser Gln Ser
                35                  40                  45

Leu Leu Asn Thr Arg Thr Arg Lys Ser Tyr Leu Ala Trp Phe Gln Gln
        50                  55                  60

Lys Pro Gly Gln Ser Pro Lys Met Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Lys Gln Ser Tyr Ser Leu Tyr Thr Phe Gly Gly Gly Thr Lys
            115                 120                 125
```

```
Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 84
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Ala Pro Gly Ala
1               5                   10                  15

Ser Val Lys Val Ser Cys Lys Ala Ser Gly Tyr Thr Phe Thr Ser Ala
            20                  25                  30

Trp Met Asn Trp Val Arg Gln Ala Pro Gly Gln Gly Leu Glu Trp Met
        35                  40                  45

Gly Arg Ile Tyr Pro Ser Gly Ser Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Arg Val Ala Arg Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 85
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Val Leu Glu Ser Gly
            20                  25                  30

Gly Gly Leu Val Gln Pro Gly Gly Ser Leu Arg Leu Ser Cys Ala Ala
        35                  40                  45

Ser Gly Phe Arg Phe Ser Ser Tyr Ala Met Ser Trp Val Arg Gln Ala
    50                  55                  60

Pro Gly Lys Gly Leu Glu Trp Val Ser Gly Ile Ser Gly Thr Gly Glu
65                  70                  75                  80

Asn Thr Tyr Tyr Ala Asp Ser Val Lys Gly Arg Phe Thr Ile Ser Arg
                85                  90                  95

Asp Asn Ser Lys Asn Thr Leu Tyr Val Gln Met Asn Ser Leu Arg Ala
            100                 105                 110

Glu Asp Thr Ala Val Tyr Tyr Cys Ala Lys Asp Ala Ile Leu Gly Ser
        115                 120                 125

Gly His Pro Trp Tyr Phe His Val Trp Gly Arg Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175
```

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly
465                 470                 475

<210> SEQ ID NO 86
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Glu Glu Ser Gly
            20                  25                  30

Gly Gly Leu Val Lys Pro Gly Gly Ser Leu Lys Leu Ser Cys Ala Ala
        35                  40                  45

Ser Gly Phe Thr Phe Ser Ser Tyr Ala Met Ser Trp Val Arg Gln Ser
    50                  55                  60

```
Pro Glu Lys Arg Leu Glu Trp Val Ala Glu Val Ser Ser Asp Gly Ser
 65                  70                  75                  80

Tyr Ala Tyr Tyr Pro Asp Thr Leu Thr Gly Arg Phe Thr Ile Ser Arg
             85                  90                  95

Asp Asn Ala Lys Asn Thr Leu Tyr Leu Glu Met Thr Ser Leu Arg Ser
            100                 105                 110

Glu Asp Thr Ala Met Tyr Tyr Cys Ala Ser Phe Asn Trp Asp Val Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465
```